United States Patent [19]
Bayer et al.

[11] Patent Number: 6,043,282
[45] Date of Patent: Mar. 28, 2000

[54] AZINOOXIMETHERS, PROCESSES AND INTERMEDIATE PRODUCTS FOR MANUFACTURING SAME, AND THE USES THEREOF IN COMBATING HARMFUL FUNGI AND PESTS

[75] Inventors: Herbert Bayer; Hubert Sauter, both of Mannheim; Klaus Oberdorf, Heidelberg; Wassilios Grammenos, Ludwigshafen; Thomas Grote, Schifferstadt; Reinhard Kirstgen, Neustadt; Bernd Müller, Frankenthal; Ruth Müller, Friedelsheim; Franz Röhl, Schifferstadt; Eberhard Ammermann, Heppenheim; Volker Harries, Frankenthal; Gisela Lorenz, Neustadt; Siegfried Strathmann, Limburgerhof, all of Germany

[73] Assignee: BASF Aktiengesellschaft, Ludwigshafen, Germany

[21] Appl. No.: 09/068,298

[22] PCT Filed: Oct. 30, 1996

[86] PCT No.: PCT/EP96/04712

§ 371 Date: Jul. 29, 1998

§ 102(e) Date: Jul. 29, 1998

[87] PCT Pub. No.: WO97/18187

PCT Pub. Date: May 22, 1997

[30] Foreign Application Priority Data

Nov. 15, 1995 [DE] Germany .......................... 195 42 629

[51] Int. Cl.⁷ .......................... A01N 33/24; A01N 37/34; A01N 43/40; A01N 43/10

[52] U.S. Cl. .......................... 514/615; 560/35; 564/134; 564/139; 564/142; 564/149; 564/150; 514/255; 514/274; 514/357; 514/365; 514/379; 514/438; 514/459; 514/522; 514/538; 514/539; 544/335; 544/336; 546/335; 548/204; 548/236; 549/72; 549/426; 558/391

[58] Field of Search .......................... 514/365, 374, 514/255, 357, 274, 438, 459, 522, 538, 539, 615; 544/335, 336; 546/335; 548/204, 236; 549/72, 426; 558/391; 560/35; 564/149, 150, 134, 139, 142

[56] References Cited

FOREIGN PATENT DOCUMENTS

95/18789  7/1995  WIPO .

*Primary Examiner*—Peter O'Sullivan
*Attorney, Agent, or Firm*—Keil & Weinkauf

[57] ABSTRACT

Azinooxime ethers of the formula I

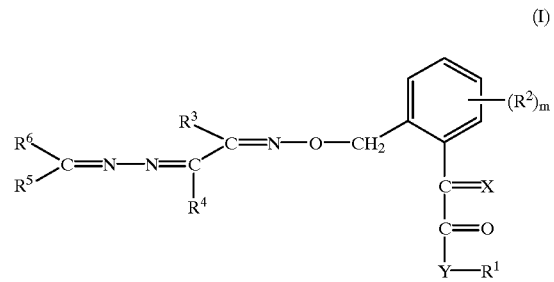

(X=NOCH₃, CHOCH₃, CHCH₃; Y=O, NZ, where Z=H, alkyl; R¹=H, alkyl; R²=cyano, nitro, trifluoromethyl, halogen, alkyl, alkoxy; m=0, 1, 2, it being possible for the radicals R² to be different if m=2; R³=H, cyano, alkyl, haloalkyl, alkoxy, cycloalkyl; R⁴, R⁵, R⁶=indepedently of one another H, unsubst. or subst. alkyl, alkenyl, alkynyl, cycloalkyl, cycloalkenyl, heterocyclyl), and their salts, processes and intermediates for their preparation and their use for controlling harmful fungi and animal pests.

8 Claims, No Drawings

AZINOOXIMETHERS, PROCESSES AND INTERMEDIATE PRODUCTS FOR MANUFACTURING SAME, AND THE USES THEREOF IN COMBATING HARMFUL FUNGI AND PESTS

This application is a 371 of PCT/EP96/04712 filed Oct. 30, 1996.

The present invention relates to azinooxime ethers of the formula I

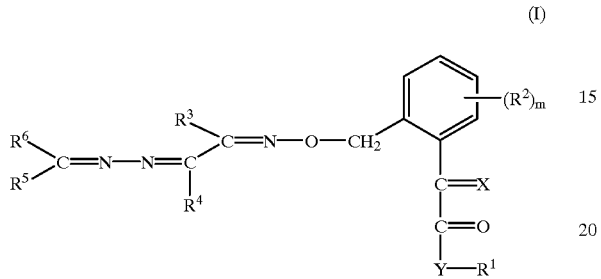

where the variables have the following meanings:

X is $NOCH_3$, $CHOCH_3$ or $CHCH_3$;
Y is O or NZ, Z being hydrogen or $C_1$–$C_4$-alkyl;
$R^1$ is hydrogen or $C_1$–$C_4$-alkyl;
$R^2$ is cyano, nitro, halogen, $C_1$–$C_4$-alkyl, trifluoromethyl or $C_1$–$C_4$-alkoxy;
m is 0, 1 or 2, it being possible for the radicals $R^2$ to be different if m is 2;
$R^3$ is hydrogen, cyano, alkyl, haloalkyl, alkoxy or cycloalkyl;
$R^4$, $R^5$, $R^6$ independently of one another are: hydrogen or unsubstituted or substituted alkyl, alkenyl, alkynyl, cycloalkyl, cycloalkenyl, heterocyclyl, aryl or heteroaryl, and their salts.

The invention additionally relates to processes and intermediates for preparing these compounds and to compositions comprising them for controlling animal pests and harmful fungi.

Phenylacetic acid derivatives of type I having fungicidal and insecticidal action are disclosed in the following publication: WO-A 95/18789. The active compounds published there, however, are unsatisfactory with respect to their action.

It is an object of the present invention to provide novel compounds of this type having improved action against harmful fungi and pests.

We have found that this object is achieved by the azinooxime ethers I defined at the outset. We have additionally found processes and intermediates for their preparation and compositions comprising them for controlling animal pests and harmful fungi and their use for this purpose.

The compounds I are obtainable in various ways by processes known per se.

In principle, it is unimportant in the synthesis of the compounds I whether the group —C(X)—CO—$YR^1$ or the group —$CH_2ON$=$C(R^3)$—$C(R^4)$=N—N=$C(R^5)R^6$ is synthesized first.

The synthesis of the group —C(X)—CO—$YR^1$ is disclosed, for example, in the following publications: EP-A 422 597, EP-A 463 488, EP-A 370 629, EP-A 460 575, EP-A 472 300, WO-A 90/07493, WO-A 92/13830, WO-A 92/18487, DE Appl. P 44 20 416.7.

1.1 In the synthesis of the group —$CH_2ON$=$C(R^3)$—$C(R^4)$=N—N=$C(R^5)R^6$ a procedure is generally used in which a benzyl derivative of the formula II is reacted with a hydroxyimine of the formula III.

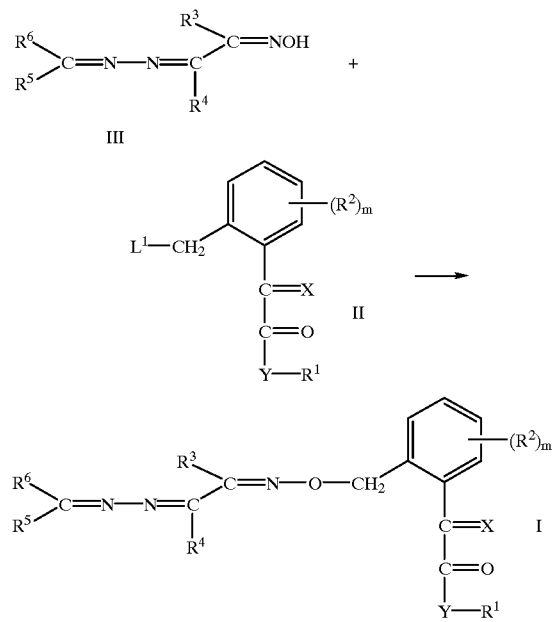

$L^1$ in the formula II is a nucleophilically replaceable leaving group, eg. halogen or a sulfonate group, preferably chlorine, bromine, iodine, mesylate, tosylate or triflate.

The reaction is carried out in a manner known per se in an inert organic solvent in the presence of a base, eg. sodium hydride, potassium hydroxide, potassium carbonate or triethylamine, according to the methods described in Houben-Weyl, 4th Edition, Vol. E 14b, p. 370 et seq. and Vol. 10/1, p. 1189 et seq.

1.2 The hydroxyimines III are obtained, for example, by reaction of a hydrazone V with a carbonyl compound of the formula VI.

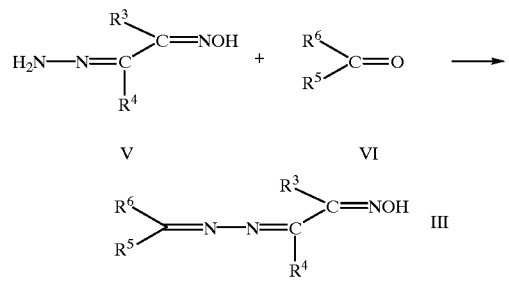

The reaction is carried out, if appropriate with acid catalysis, in a manner known per se in an inert organic solvent (cf. Bull. Soc. Chim. Fr. 713 (1968); Houben-Weyl, 4th Edition, Vol. X/2, page 104 et seq.).

The hydrazones V are known or can be prepared by methods known per se [cf. J. Med. Chem. 21 (1978), 623; J. Chem. Soc. 101 (1912), 2238; J. Org. Chem. 25 (1960), 313).

1.3 A further possibility for the preparation of the hydroxyimines III consists in reacting a carbonylhydroxyimino derivative IV with a hydrazone of the formula VII, as described in 1.2.

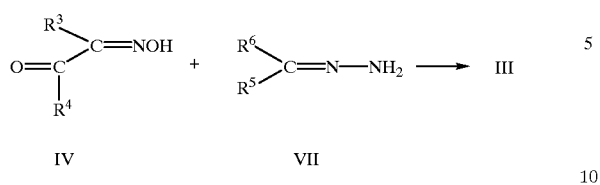

2. Alternatively, the compounds I can also be obtained by first reacting the benzyl derivative II with the carbonylhydroxyimino derivative IV to give a corresponding benzyloxime of the formula VIII, and then reacting VIII with a compound VII (see above) to give I.

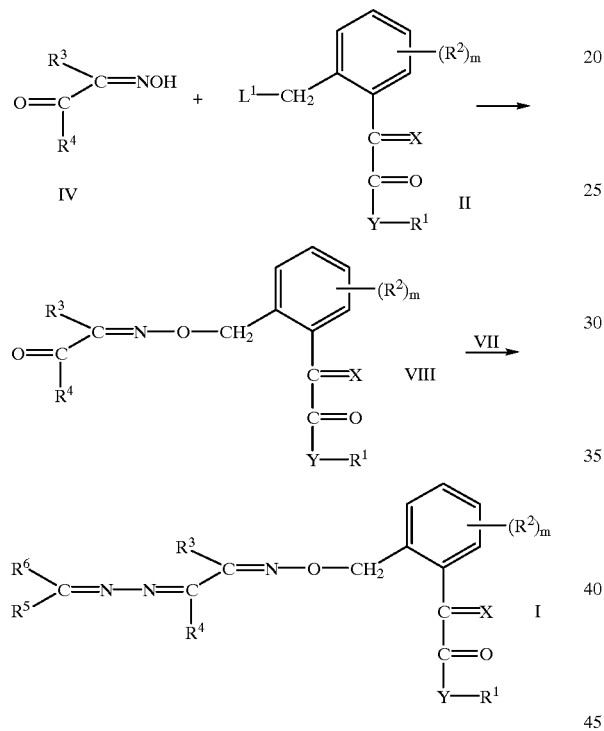

The reaction of IV with II is carried out similarly to the synthesis such as is described in 1.1. The reaction of VIII with VII is carried out similarly to the synthesis which is described in 1.2.

3.1 The synthesis of the compounds I is furthermore possible by reacting a compound of the formula VIII first with hydrazine hydrate to give the hydrazone of the formula IX and then reacting this with a carbonyl compound of the formula VI.

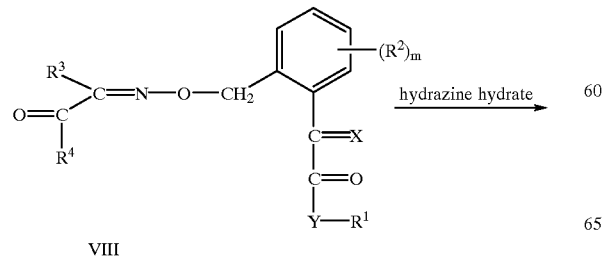

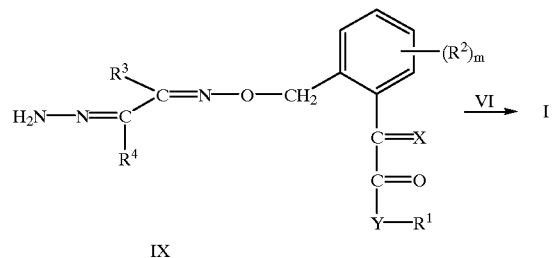

The reactions are carried out similarly to the synthesis which is described in 1.2.

3.2 The synthesis of the derivatives IX is also possible by reacting a benzyl derivative of the formula II with a hydroxyimine of the formula V.

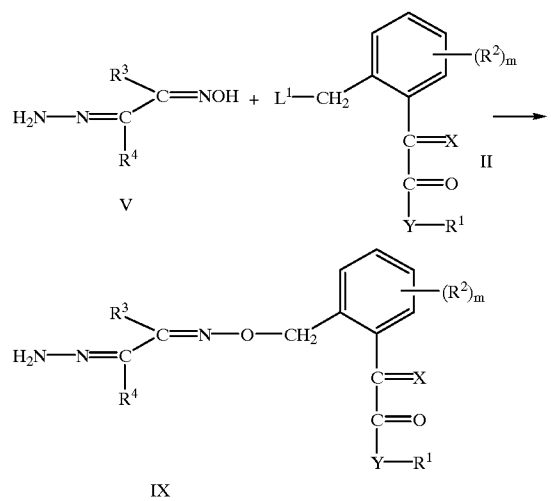

$L^1$ in the formula II is a nucleophilically replaceable leaving group, eg. halogen or a sulfonate group, preferably chlorine, bromine, iodine, mesylate, tosylate or triflate.

The reaction is carried out similarly to the synthesis which is described in 1.1.

4. In addition, the compounds I are obtained by first converting a compound III as in EP-A 493 711 using a lactone X into the corresponding benzoic acid XI and converting XI via the corresponding halides XII into the cyanocarboxylic acids XIII, which are converted by way of the Pinner reaction (Angew. Chem. 94, 1 (1982)) into the α-ketoesters XIV and, if desired, reacted further to give the α-ketoamides XV (cf. EP-A 348 766, DE-A 37 05 389, EP-A 178 826, DE-A 36 23 921, Houben-Weyl, 4th Edition, Vol. E5, pp. 941 et seq.)

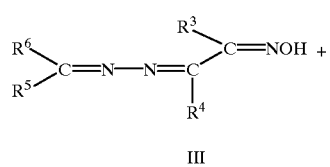

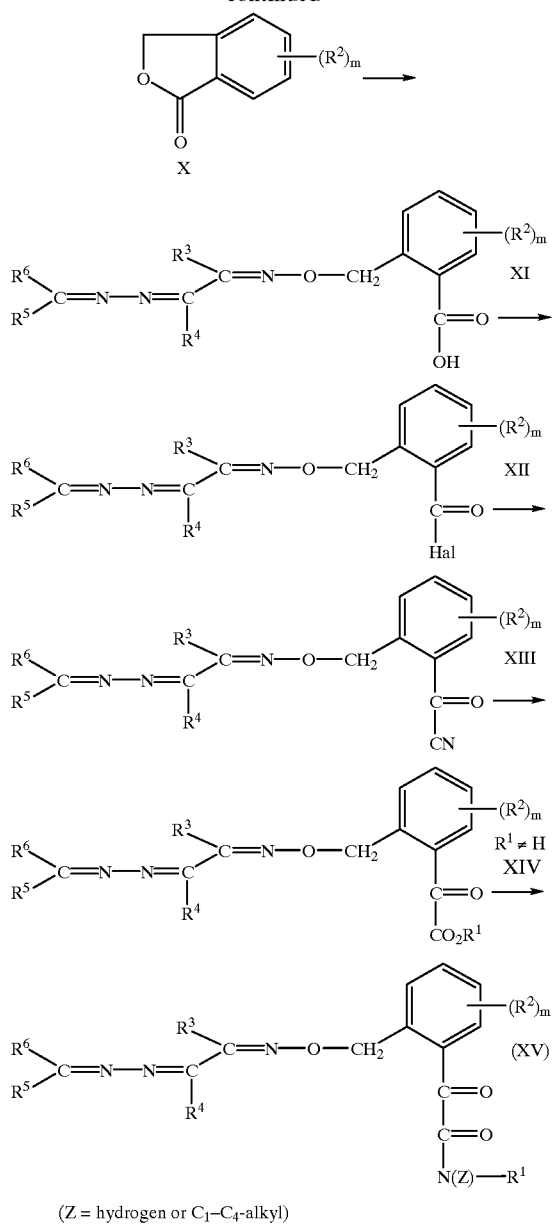

(Z = hydrogen or $C_1$–$C_4$-alkyl)

The α-ketoesters XIV and the α-ketoamides XV can be converted into the compounds I according to customary processes (cf. EP-A 178 826, EP-A 348 766, DE-A 36 23 921, DE-A 37 05 389 and the literature cited at the outset).

Compounds I in which $R^1$ is hydrogen are obtained according to this process by hydrolysis of the esters XIV and subsequent reaction to give I.

The compounds I in which Y is NZ can also be obtained from the esters (Y=O) by reaction with the appropriate amines HN(Z)$R^1$.

The compounds II are disclosed in EP-A 513 580, EP-A 477 631, EP-A 463 488, EP-A 251 082, EP-A 400 417 and/or EP-A 585 751 or can be prepared by the methods described there.

On account of their C=C and C=N double bonds, the compounds I can be obtained during the preparation as E/Z isomer mixtures, which can be separated into the individual compounds in a customary manner, eg. by crystallization or chromatography.

If isomer mixtures are obtained during synthesis, in general, however, separation of the isomers is not absolutely necessary, as the individual isomers can partially be converted into one another during preparation for application or during application (eg. under the action of light, acid or base). Corresponding conversions can also take place after application, for example during the treatment of plants, in the treated plants or in the harmful fungus or animal pest to be controlled.

With regard to the C=X double bond, the E isomers of the compounds I are preferred with respect to their activity (configuration based on the —$OCH_3$ or the —$CH_3$ group in relation to the —$COYR^1$ group).

With regard to the —$C(R^3)$=$NOCH_2$— double bond, the cis isomers of the compounds I are preferred with respect to their activity (configuration based on the radical $R^3$ in relation to the —$OCH_2$— group).

Also part of the invention are the salts of the acid-stable compounds I, which contain basic centers, especially basic nitrogen atoms, in particular with mineral acids such as sulfuric acid and phosphoric acid or Lewis acids such as zinc chloride. Customarily, the nature of the salt does not matter here. Within the meaning of the invention, those salts are preferred which do not damage the plants, surfaces, materials or spaces to be kept free from harmful fungi or animal pests and do not adversely affect the action of the compounds I. Particularly important salts are those of the type suitable for agricultural purposes.

The salts of the compounds I are accessible in a manner known per se, especially by reacting the corresponding biphenylamides I with the acids mentioned in water or an inert organic solvent at from −80 to 120° C., preferably 0 to 60° C.

In the definitions of the compounds I given at the outset, collective terms were used which are generally representative of the following groups:

halogen: fluorine, chlorine, bromine and iodine;

alkyl: straight-chain or branched alkyl groups having 1 to 4, 6 or 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkylamino: an amino group which carries a straight-chain or branched alkyl group having 1 to 6 carbon atoms as mentioned above;

dialkylamino: an amino group which carries two straight-chain or branched alkyl groups which are independent of one another and each have 1 to 6 carbon atoms as mentioned above;

alkylcarbonyl: straight-chain or branched alkyl groups having 1 to 10 carbon atoms, which are bonded to the structure via a carbonyl group (—CO—);

alkylsulfonyl: straight-chain or branched alkyl groups having 1 to 6 or 10 carbon atoms, which are bonded to the structure via a sulfonyl group (—$SO_2$—);

alkylsulfoxyl: straight-chain or branched alkyl groups having 1 to 6 carbon atoms, which are bonded to the structure via a sulfoxyl group (—S(=O)—);

alkylaminocarbonyl: alkylamino groups having 1 to 6 carbon atoms as mentioned above, which are bonded to the structure via a carbonyl group (—CO—);

dialkylaminocarbonyl: dialkylamino groups each having 1 to 6 carbon atoms per alkyl radical as mentioned above, which are bonded to the structure via a carbonyl group (—CO—);

alkylaminothiocarbonyl: alkylamino groups having 1 to 6 carbon atoms as mentioned above, which are bonded to the structure via a thiocarbonyl group (—CS—);

dialkylaminothiocarbonyl: dialkylamino groups each having 1 to 6 carbon atoms per alkyl radical as mentioned above, which are bonded to the structure via a thiocarbonyl group (—CS—);

haloalkyl: straight-chain or branched alkyl groups having 1 to 6 carbon atoms, it being possible in these groups for the hydrogen atoms to be partially or completely replaced by halogen atoms as mentioned above, eg. $C_1$–$C_2$-haloalkyl such as chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

alkoxy: straight-chain or branched alkyl groups having 1 to 4 or 6 carbon atoms as mentioned above, which are bonded to the structure via an oxygen atom (—O—), eg. $C_1$–$C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

alkoxycarbonyl: straight-chain or branched alkyl groups having 1 to 6 carbon atoms, which are bonded to the structure via an oxycarbonyl group (—OC(=O)—);

alkylenedioxy: eg. $C_1$–$C_4$-alkylenedioxy: straight-chain or branched alkylene groups having 1 to 4 carbon atoms, which are bonded into the structure in two positions, each via an oxygen atom (—O—), or are bonded to the structure, such as methylenedioxy (—O—$CH_2$—O—) or 2,2-propylenedioxy (—O—C($CH_3$)$_2$—O—);

haloalkoxy: straight-chain or branched alkyl groups having 1 to 6 carbon atoms, it being possible in these groups for the hydrogen atoms to be partially or completely replaced by halogen atoms as mentioned above, and these groups being bonded to the structure via an oxygen atom;

alkylthio: straight-chain or branched alkyl groups having 1 to 4 or 6 carbon atoms as mentioned above, which are bonded to the structure via a sulfur atom (—S—), eg. $C_1$–$C_6$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

cycloalkyl: monocyclic alkyl groups having 3 to 6 carbon ring members, eg. cyclopropyl, cyclobutyl, cyclopentyl and cyclohexyl;

alkenyl: straight-chain or branched alkenyl groups having 2 to 6 or 10 carbon atoms and a double bond in any desired position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkenyloxy: straight-chain or branched alkenyl groups having 2 to 6 carbon atoms and a double bond in any desired position, which are bonded to the structure via an oxygen atom (—O—);

alkenylthio or alkenylamino: straight-chain or branched alkenyl groups having 2 to 6 carbon atoms and a double bond in any desired position, which (alkenylthio) are bonded to the structure via a sulfur atom or (alkenylamino) a nitrogen atom;

alkenylcarbonyl: straight-chain or branched alkenyl groups having 2 to 10 carbon atoms and a double bond in any desired position, which are bonded to the structure via a carbonyl group (—CO—);

alkynyl: straight-chain or branched alkynyl groups having 2 to 10 carbon atoms and a triple bond in any desired position, eg. $C_2$–$C_6$-alkynyl such as ethynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 1-ethyl-2-butynyl, 1-ethyl-3-butynyl, 2-ethyl-3-butynyl and 1-ethyl-1-methyl-2-propynyl;

alkynyloxy or alkynylthio and alkynylamino: straight-chain or branched alkynyl groups having 2 to 6 carbon atoms and a triple bond in any desired position, which (alkynyloxy) are bonded to the structure via an oxygen atom or (alkynylthio) via a sulfur atom or (alkynylamino) via a nitrogen atom;

alkynylcarbonyl: straight-chain or branched alkynyl groups having 3 to 10 carbon atoms and a triple bond in any desired position, which are bonded to the structure via a carbonyl group (—CO—);

cycloalkenyl or cycloalkenyloxy, cycloalkenylthio and cycloalkenylamino: monocyclic alkenyl groups having 3 to 6 carbon ring members, which are bonded to the structure directly or (cycloalkenyloxy) via an oxygen atom or (cycloalkenylthio) a sulfur atom or (cycloalkenylamino) via a nitrogen atom, eg. cyclopropenyl, cyclobutenyl, cyclopentenyl or cyclohexenyl;

cycloalkoxy or cycloalkylthio and cycloalkylamino: monocyclic alkyl groups having 3 to 6 carbon ring members, which (cycloalkoxy) are bonded to the structure via an oxygen atom or (cycloalkylthio) a sulfur atom or (cycloalkylamino) via a nitrogen atom, eg. cyclopropyl, cyclobutyl, cyclopentyl or cyclohexyl;

heterocyclyl or heterocyclyloxy, heterocyclylthio and heterocyclylamino: three- to six-membered, saturated or partially unsaturated mono- or polycyclic heterocycles, which contain one to three heteroatoms selected from a group consisting of oxygen, nitrogen and sulfur, and which are bonded to the structure directly or (heterocyclyloxy) via an oxygen atom or (heterocyclylthio) via a sulfur atom or (heterocyclylamino) via a nitrogen atom, such as, for example, 2-tetrahydrofuranyl, oxiranyl, 3-tetrahydrofuranyl, 2-tetrahydrothienyl, 3-tetrahydrothienyl, 2-pyrrolidinyl, 3-pyrrolidinyl, 3-isoxazoldinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,3-dihydrofur-4-yl, 2,3-dihydrofur-5-yl, 2,5-dihydrofur-2-yl, 2,5-dihydrofur-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisothiazol-3-yl, 2,5-dihydroisothiazol-4-yl, 2,5-dihydroisothiazol-5-yl, 2,3-dihydroisopyrazol-3-yl, 2,3-dihydroisopyrazol-4-yl, 2,3-dihydroisopyrazol-5-yl, 4,5-dihydroisopyrazol-3-yl, 4,5-dihydroisopyrazol-4-yl, 4,5-dihydroisopyrazol-5-yl, 2,5-dihydroisopyrazol-3-yl, 2,5-dihydroisopyrazol-4-yl, 2,5-dihydroisopyrazol-5-yl, 2,3-dihydrooxazol-3-yl, 2,3-dihydrooxazol-4-yl, 2,3-dihydrooxazol-5-yl, 4,5-dihydrooxazol-3-yl, 4,5-dihydrooxazol-4-yl, 4,5-dihydrooxazol-5-yl, 2,5-dihydrooxazol-3-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 1,3-dioxolan-2-yl, 3,4,5,6-tetrahydropyridin-2-yl, 4H-1,3-thiazin-2-yl, 4H-3,1-benzothiazin-2-yl, 1,1-dioxo-2,3,4,5-tetrahydrothien-2-yl, 2H-1,4-benzothiazin-3-yl, 2H-1,4-benzoxazin-3-yl, 1,3-dihydrooxazin-2-yl, 1,3-dithian-2-yl;

aryl or aryloxy, arylthio, arylcarbonyl and arylsulfonyl: aromatic mono- or polycyclic hydrocarbon radicals which are bonded to the structure directly or (aryloxy) via an oxygen atom (—O—) or (arylthio) a sulfur atom (—S—), (arylcarbonyl) via a carbonyl group (—CO—) or (arylsulfonyl) via a sulfonyl group (—SO$_2$—), eg. phenyl, naphthyl and phenanthrenyl or phenoxy, naphthyloxy and phenanthrenyloxy and the corresponding carbonyl and sulfonyl radicals;

arylamino: aromatic mono- or polycyclic hydrocarbon radicals, which are bonded to the structure via a nitrogen atom;

heteroaryl or heteroaryloxy, heteroarylthio, heteroarylcarbonyl and hetarylsulfonyl: aromatic mono- or polycyclic radicals which, beside carbon ring members, can additionally contain one to four nitrogen atoms or one to three nitrogen atoms and an oxygen atom or a sulfur atom and which are bonded to the structure directly or (hetaryloxy) via an oxygen atom (—O—) or (hetarylthio) a sulfur atom (—S—), (hetarylcarbonyl) via a carbonyl group (—CO—) or (hetarylsulfonyl) via a sulfonyl group (—SO$_2$—), eg.

5-membered heteroaryl, containing one to three nitrogen atoms: 5-membered ring heteroaryl groups, which beside carbon atoms can contain one to three nitrogen atoms as ring members, eg. 2-pyrrolyl, 3-pyrrolyl, 3-pyrazolyl, 4-pyrazolyl, 5-pyrazolyl, 2-imidazolyl, 4-imidazolyl, 1,2,4-triazol-3-yl and 1,3,4-triazol-2-yl;

5-membered heteroaryl, containing one to four nitrogen atoms or one to three nitrogen atoms and a sulfur or oxygen atom or an oxygen or a sulfur atom: 5-membered ring heteroaryl groups, which beside carbon atoms can contain one to four nitrogen atoms or one to three nitrogen atoms and a sulfur or oxygen atom or an oxygen or sulfur atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl;

benzo-fused 5-membered heteroaryl, containing one to three nitrogen atoms or a nitrogen atom and/or an oxygen or sulfur atom: 5-membered ring heteroaryl groups, which beside carbon atoms can contain one to four nitrogen atoms or one to three nitrogen atoms and a sulfur or oxygen atom or an oxygen or a sulfur atom as ring members, and in which two adjacent carbon ring members or a nitrogen and an adjacent carbon ring member can be bridged by a buta-1,3-diene-1,4-diyl group;

5-membered heteroaryl bonded via nitrogen, containing one to four nitrogen atoms, or benzo-fused 5-membered heteroaryl bonded via nitrogen, containing one to three sulfur atoms: 5-membered ring heteroaryl groups, which beside carbon atoms can contain one to four nitrogen atoms or one to three nitrogen atoms as ring members, and in which two adjacent carbon ring members or a nitrogen and an adjacent carbon ring member can be bridged by a buta-1,3-diene-1,4-diyl group, these rings being bonded to the structure via one of the nitrogen ring members;

6-membered heteroaryl, containing one to three or one to four nitrogen atoms: 6-membered ring heteroaryl groups, which beside carbon atoms can contain one to three or one to four nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 6-membered heteroaryl, containing one to four nitrogen atoms: 6-membered ring heteroaryl groups in which two adjacent carbon ring members can be bridged by a buta-1,3-diene-1,4-diyl group, eg. quinoline, isoquinoline, quinazoline and quinoxaline, or the corresponding oxy, thio, carbonyl or sulfonyl groups;

heteroarylamino: aromatic mono- or polycyclic radicals, which beside carbon ring members can additionally contain one to four nitrogen atoms or one to three nitrogen atoms and an oxygen or a sulfur atom and which are bonded to the structure via a nitrogen atom.

The statement "partially or completely halogenated" is intended to express that in the groups characterized in this way the hydrogen atoms can be partially or completely replaced by identical or different halogen atoms, as mentioned above.

The statement "unsubstituted or substituted" is intended to express that in the groups characterized in this way the hydrogen atoms can be partially or completely replaced by identical or different groups, for example those which are mentioned under the collective terms listed above.

With respect to their biological action, compounds of the formula I are preferred in which the variables have the following meanings:

X is $NOCH_3$, $CHOCH_3$ or $CHCH_3$;

Y is O or NZ, Z being hydrogen or $C_1$–$C_4$-alkyl;

$R^1$ is hydrogen or $C_1$–$C_4$-alkyl;

$R^2$ is cyano, nitro, halogen, $C_1$–$C_4$-alkyl, trifluoromethyl or $C_1$–$C_4$-alkoxy;

m is 0, 1 or 2, it being possible for the radicals $R^2$ to be different if m is 2;

$R^3$ is hydrogen, cyano, $C_1$–$C_4$-alkyl, $C_1$–$C_4$-haloalkyl, $C_1$–$C_4$-alkoxy or cyclopropyl;

$R^4$, $R^5$ and $R^6$ independently of one another are:
hydrogen;

$C_1$–$C_6$-alkyl, $C_2$–$C_6$-alkenyl, $C_2$–$C_6$-alkynyl, it being possible for these radicals to be partially or completely halogenated and/or to carry one to three of the following groups: cyano, nitro, hydroxyl, mercapto, amino, carboxyl, aminocarbonyl, aminothiocarbonyl, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_1$–$C_6$-alkylsulfonyl, $C_1$–$C_6$-alkylsulfoxyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyloxy, $C_3$–$C_6$-cycloalkyl, $C_3$–$C_6$-cycloalkyloxy, heterocyclyl, heterocyclyloxy, aryl, aryloxy, aryl-$C_1$–$C_4$-alkoxy, arylthio, aryl-$C_1$–$C_4$-alkylthio, heteroaryl, heteroaryloxy, heteroaryl-$C_1$–$C_4$-alkoxy, heteroarylthio and heteroaryl-$C_1$–$C_4$-alkylthio, it being possible for the cyclic groups in turn to be partially or completely halogenated and/or to carry one to three of the following substituents: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, heteroaryl, heteroaryloxy, heteroarylthio, $C_3$–$C_6$-alkynyloxy, $C_1$–$C_4$-alkylenedioxy, which can be halogenated, and $C(=NOR^7)$-$A_n$-$R^8$, A being oxygen, sulfur or nitrogen and the nitrogen carrying hydrogen or $C_1$–$C_6$-alkyl, n being 0 or 1, $R^7$ being hydrogen or $C_1$–$C_6$-alkyl and $R^8$ being hydrogen or $C_1$–$C_6$-alkyl;

$C_3$–$C_6$-cycloalkyl, $C_3$–$C_6$-cycloalkenyl, heterocyclyl, it being possible for these radicals to be partially or completely halogenated and/or to carry one to three of the following groups: cyano, $C_1$–$C_6$-alkyl, $C_1$–$C_6$-haloalkyl, $C_2$–$C_6$-alkenyl, $C_1$–$C_6$-alkoxy and $C_1$–$C_6$-alkylthio;

aryl or heteroaryl, it being possible for these radicals to be partially or completely halogenated and/or to carry one to three of the following groups: cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylcarbonyl, $C_1$–$C_6$-alkylsulfonyl, $C_1$–$C_6$-alkylsulfoxyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, arylthio, heteroaryl, heteroaryloxy, heteroarylthio, $C_3$–$C_6$-alkynyloxy, $C_1$–$C_4$-alkylenedioxy, which can be halogenated, and $C(=NOR^7)$-$A_n$-$R^8$, A being oxygen, sulfur or nitrogen and the nitrogen carrying hydrogen or $C_1$–$C_6$-alkyl, n being 0 or 1, $R^7$ being hydrogen or $C_1$–$C_6$-alkyl and $R^8$ being hydrogen or $C_1$–$C_6$-alkyl and it being possible for the cyclic groups in turn to be partially or completely halogenated and/or to carry one to three of the following substituents: cyano, nitro, hydroxyl, $C_1$–$C_6$-alkyl, $C_1$–$C_6$-haloalkyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_2$–$C_6$-alkenyl, $C_2$–$C_6$-alkenyloxy, $C_3$–$C_6$-alkynyloxy and $C_1$–$C_4$-alkylenedioxy, which can be halogenated;

$R^5$ and $R^6$, together with the carbon atom to which they are bonded, are an unsubstituted or substituted saturated or unsaturated carbocyclic or heterocyclic ring, if desired preferably substituted as follows: partially or completely halogenated and/or carrying one to three of the following groups: cyano, $C_1$–$C_6$-alkyl, $C_1$–$C_6$-haloalkyl, $C_2$–$C_6$-alkenyl, $C_1$–$C_6$-alkoxy and $C_1$–$C_6$-alkylthio, and their salts.

Furthermore, compounds of the formula I are preferred in which m is 0.

Equally, preferred compounds of the formula I are those in which $R^1$ is methyl.

In addition, compounds I are preferred in which $R^3$ is hydrogen, cyclopropyl, methyl, ethyl, 1-methylethyl, trifluoromethyl, cyano or methoxy.

Particularly preferred compounds I are those in which $R^3$ is methyl.

In addition, compounds I are preferred in which $R^3$ is trifluoromethyl.

Particularly preferred compounds I are also those in which $R^3$ is methoxy.

In addition, compounds I are preferred in which $R^4$ is unsubstituted or substituted $C_1$–$C_6$-alkyl, $C_2$–$C_6$-alkenyl or $C_2$–$C_6$-alkynyl.

Additionally, compounds I are preferred in which $R^4$ is unsubstituted or substituted heterocyclyl or unsubstituted or substituted $C_3$–$C_6$-cycloalkenyl.

Particularly preferred compounds I are those in which $R^4$ is $C_1$–$C_4$-alkyl.

Additionally, compounds I are preferred in which $R^4$ is unsubstituted or substituted $C_3$–$C_6$-cycloalkyl.

In addition, compounds I are preferred in which $R^4$ is unsubstituted or substituted aryl or hetaryl.

In addition, compounds I are preferred in which $R^4$ is unsubst. or subst. pyridyl, pyrimidyl, pyrazinyl, pyridazinyl or triazinyl.

In addition, compounds I are preferred in which $R^4$ is unsubst. or subst. furyl, thienyl or pyrrolyl.

In addition, compounds I are preferred in which $R^4$ is unsubst. or subst. oxazolyl, thiazolyl, isoxazolyl, isothiazolyl, pyrazolyl or imidazolyl.

In addition, compounds I are preferred in which $R^4$ is unsubst. or subst. oxadiazolyl, thiadiazolyl or triazolyl.

Additionally, compounds I are preferred in which $R^4$ is phenyl which is unsubstituted or carries one or two of the following groups: nitro, cyano, hydroxyl, amino, aminocarbonyl, aminothiocarbonyl, halogen, $C_1$–$C_4$-alkyl, $C_1$–$C_4$-haloalkyl, $C_3$–$C_6$-cycloalkyl, $C_1$–$C_4$-alkoxy, $C_1$–$C_4$-haloalkoxy, $C_1$–$C_4$-alkylamino, $C_1$–$C_4$-alkylcarbonyl, di-$C_1$–$C_4$-alkylamino, $C_1$–$C_4$-alkylsulfonyl, $C_1$–$C_4$-alkoxycarbonyl, $C_1$–$C_4$-alkylaminocarbonyl, di-$C_1$–$C_4$-alkylaminocarbonyl, $C_1$–$C_4$-alkylthio, $C_2$–$C_6$-alkenyl, $C_2$–$C_6$-alkenyloxy, $C_3$–$C_6$-alkynyloxy and $C_1$–$C_4$-alkylenedioxy, which can be halogenated.

In addition, compounds I are preferred in which $R^5$ is unsubstituted or substituted $C_1$–$C_6$-alkyl.

Additionally, compounds I are preferred in which $R^5$ is methyl or ethyl.

In addition, compounds I are preferred in which $R^5$ is hydrogen.

Additionally, compounds I are preferred in which $R^5$ is unsubstituted or substituted $C_2$–$C_6$-alkenyl.

Furthermore, compounds I are preferred in which $R^5$ is unsubstituted or substituted $C_2$–$C_6$-alkynyl.

Additionally, compounds I are preferred in which $R^5$ is unsubstituted or substituted hetaryl.

In addition, compounds I are preferred in which $R^5$ is unsubst. or subst. pyridyl, pyrimidyl, pyrazinyl, pyridazinyl or triazinyl.

In addition, compounds I are preferred in which $R^5$ is unsubst. or subst. furyl, thienyl or pyrrolyl.

In addition, compounds I are preferred in which $R^5$ is unsubst. or subst. oxazolyl, thiazolyl, isoxazolyl, isothiazolyl, pyrazolyl or imidazolyl.

In addition, compounds I are preferred in which $R^5$ is unsubst. or subst. aryl.

Additionally, compounds I are preferred in which $R^5$ is phenyl which is unsubstituted or carries one or two of the following groups: nitro, cyano, hydroxyl, amino, aminocarbonyl, aminothiocarbonyl, halogen, $C_1$–$C_4$-alkyl, $C_1$–$C_4$-haloalkyl, $C_3$–$C_6$-cycloalkyl, $C_1$–$C_4$-alkoxy, $C_1$–$C_4$-haloalkoxy, $C_1$–$C_4$-alkylamino, $C_1$–$C_4$-alkylcarbonyl, di-$C_1$–$C_4$-alkylamino, $C_1$–$C_4$-alkylsulfonyl, $C_1$–$C_4$-alkoxycarbonyl, $C_1$–$C_4$-alkylaminocarbonyl, di-$C_1$–$C_4$-alkylaminocarbonyl, $C_1$–$C_4$-alkylthio, $C_2$–$C_6$-alkenyl, $C_2$–$C_6$-alkenyloxy, $C_3$–$C_6$-alkynyloxy and $C_1$–$C_4$-alkylenedioxy, which can be halogenated.

In addition, compounds I are preferred in which $R^6$ is unsubst. or subst. $C_1$–$C_6$-alkyl.

Additionally, compounds I are preferred in which $R^6$ is methyl or ethyl.

In addition, compounds I are preferred in which $R^6$ is hydrogen.

Additionally, compounds I are preferred in which $R^6$ is unsubst. or subst. $C_2$–$C_6$-alkenyl.

Additionally, compounds I are preferred in which $R^6$ is unsubst. or subst. $C_2$–$C_6$-alkynyl.

Additionally, compounds I are preferred in which $R^6$ is unsubstituted or substituted hetaryl.

In addition, compounds I are preferred in which $R^6$ is unsubst. or subst. pyridyl, pyrimidyl, pyrazinyl, pyridazinyl or triazinyl.

In addition, compounds I are preferred in which $R^6$ is unsubst. or subst. furyl, thienyl or pyrrolyl.

In addition, compounds I are preferred in which $R^6$ is unsubst. or subst. oxazolyl, thiazolyl, isoxazolyl, isothiazolyl, pyrazolyl or imidazolyl.

In addition, compounds I are preferred in which $R^6$ is unsubst. or subst. aryl.

Additionally, compounds I are preferred in which $R^6$ is phenyl which is unsubstituted or carries one or two of the following groups: nitro, cyano, hydroxyl, amino, aminocarbonyl, aminothiocarbonyl, halogen, $C_1$–$C_4$-alkyl, $C_1$–$C_4$-haloalkyl, $C_3$–$C_6$-cycloalkyl, $C_1$–$C_4$-alkoxy, $C_1$–$C_4$-haloalkoxy, $C_1$–$C_4$-alkylamino, $C_1$–$C_4$-alkylcarbonyl, di-$C_1$–$C_4$-alkylamino, $C_1$–$C_4$-alkylsulfonyl, $C_1$–$C_4$-alkoxycarbonyl, $C_1$–$C_4$-alkylaminocarbonyl, di-$C_1$–$C_4$-alkylaminocarbonyl, $C_1$–$C_4$-alkylthio, $C_2$–$C_6$-alkenyl, $C_2$–$C_6$-alkenyloxy, $C_3$–$C_6$-alkynyloxy and $C_1$–$C_4$-alkylenedioxy, which can be halogenated.

In addition, compounds of the formula I are preferred in which X is $NOCH_3$.

In addition, compounds of the formula I are preferred in which X is $CHOCH_3$.

In addition, compounds of the formula I are preferred in which X is $CHCH_3$.

In addition, compounds of the formula I are preferred in which Y is O.

Additionally, compounds of the formula I are preferred in which Y is NH.

In particular, the compounds compiled in the following tables are preferred with respect to their use.

The following tables (1 to 728) are based on the formulae I.1, I.2, I.3 and I.4, the double bonds marked by "E" having the E configuration:

(I.1)

$R^5$=hydrogen;
$R^4$=in each case one line of Table A.

Table 5

Compounds of the formula I.1, where
$R^6$=hydrogen;
$R^5$=methyl;
$R^4$=in each case one line of Table A.

Table 6

Compounds of the formula I.2, where
$R^6$=hydrogen;
$R^5$=methyl;
$R^4$=in each case one line of Table A.

Table 7

Compounds of the formula I.3, where
$R^6$=hydrogen;
$R^5$=methyl;
$R^4$=in each case one line of Table A.

Table 8

Compounds of the formula I.4, where
$R^6$=hydrogen;
$R^5$=methyl;
$R^4$=in each case one line of Table A.

Table 9

Compounds of the formula I.1, where
$R^6$=hydrogen;
$R^5$=ethyl;
$R^4$=in each case one line of Table A.

Table 10

Compounds of the formula I.2, where
$R^6$=hydrogen;
$R^5$=ethyl;
$R^4$=in each case one line of Table A.

Table 11

Compounds of the formula I.3, where
$R^6$=hydrogen;
$R^5$=ethyl;
$R^4$=in each case one line of Table A.

Table 12

Compounds of the formula I.4, where
$R^6$=hydrogen;
$R^5$=ethyl;
$R^4$=in each case one line of Table A.

Table 1

Compounds of the formula I.1, where
$R^6$=hydrogen;
$R^5$=hydrogen;
$R^4$=in each case one line of Table A.

Table 2

Compounds of the formula I.2, where
$R^6$=hydrogen;
$R^5$=hydrogen;
$R^4$=in each case one line of Table A.

Table 3

Compounds of the formula I.3, where
$R^6$=hydrogen;
$R^5$=hydrogen;
$R^4$=in each case one line of Table A.

Table 4

Compounds of the formula I.4, where
$R^6$=hydrogen;

Table 13

Compounds of the formula I.1, where
$R^6$=hydrogen;
$R^5$=n-propyl;
$R^4$=in each case one line of Table A.

Table 14

Compounds of the formula I.2, where
$R^6$=hydrogen;

$R^5$=n-propyl;
$R^4$=in each case one line of Table A.

Table 15

Compounds of the formula I.3, where
$R^6$=hydrogen;
$R^5$=n-propyl;
$R^4$=in each case one line of Table A.

Table 16

Compounds of the formula I.4, where
$R^6$=hydrogen;
$R^5$=n-propyl;
$R^4$=in each case one line of Table A.

Table 17

Compounds of the formula I.1, where
$R^6$=hydrogen;
$R^5$=isopropyl;
$R^4$=in each case one line of Table A.

Table 18

Compounds of the formula I.2, where
$R^6$=hydrogen;
$R^5$=isopropyl;
$R^4$=in each case one line of Table A.

Table 19

Compounds of the formula I.3, where
$R^6$=hydrogen;
$R^5$=isopropyl;
$R^4$=in each case one line of Table A.

Table 20

Compounds of the formula I.4, where
$R^6$=hydrogen;
$R^5$=isopropyl;
$R^4$=in each case one line of Table A.

Table 21

Compounds of the formula I.1, where
$R^6$=hydrogen;
$R^5$=cyclopropyl;
$R^4$=in each case one line of Table A.

Table 22

Compounds of the formula I.2, where
$R^6$=hydrogen;
$R^5$=cyclopropyl;
$R^4$=in each case one line of Table A.

Table 23

Compounds of the formula I.3, where
$R^6$=hydrogen;
$R^5$=cyclopropyl;
$R^4$=in each case one line of Table A.

Table 24

Compounds of the formula I.4, where
$R^6$=hydrogen;
$R^5$=cyclopropyl;
$R^4$=in each case one line of Table A.

Table 25

Compounds of the formula I.1, where
$R^6$=hydrogen;
$R^5$=n-butyl;
$R^4$=in each case one line of Table A.

Table 26

Compounds of the formula I.2, where
$R^6$=hydrogen;
$R^5$=n-butyl;
$R^4$=in each case one line of Table A.

Table 27

Compounds of the formula I.3, where
$R^6$=hydrogen;
$R^5$=n-butyl;
$R^4$=in each case one line of Table A.

Table 28

Compounds of the formula I.4, where
$R^6$=hydrogen;
$R^5$=n-butyl;
$R^4$=in each case one line of Table A.

Table 29

Compounds of the formula I.1, where
$R^6$=hydrogen;
$R^5$=isobutyl;
$R^4$=in each case one line of Table A.

Table 30

Compounds of the formula I.2, where
$R^6$=hydrogen;
$R^5$=isobutyl;
$R^4$=in each case one line of Table A.

Table 31

Compounds of the formula I.3, where
$R^6$=hydrogen;
$R^5$=isobutyl;
$R^4$=in each case one line of Table A.

Table 32

Compounds of the formula I.4, where
$R^6$=hydrogen;
$R^5$=isobutyl;
$R^4$=in each case one line of Table A.

Table 33

Compounds of the formula I.1, where
$R^6$=hydrogen;
$R^5$=sec-butyl;
$R^4$=in each case one line of Table A.

Table 34

Compounds of the formula I.2, where
$R^6$=hydrogen;

$R^5$=sec-butyl;
$R^4$=in each case one line of Table A.

Table 35

Compounds of the formula I.3, where
$R^6$=hydrogen;
$R^5$=sec-butyl;
$R^4$=in each case one line of Table A.

Table 36

Compounds of the formula I.4, where
$R^6$=hydrogen;
$R^5$=sec-butyl;
$R^4$=in each case one line of Table A.

Table 37

Compounds of the formula I.1, where
$R^6$=hydrogen;
$R^5$=t-butyl;
$R^4$=in each case one line of Table A.

Table 38

Compounds of the formula I.2, where
$R^6$=hydrogen;
$R^5$=t-butyl;
$R^4$=in each case one line of Table A.

Table 39

Compounds of the formula I.3, where
$R^6$=hydrogen;
$R^5$=t-butyl;
$R^4$=in each case one line of Table A.

Table 40

Compounds of the formula I.4, where
$R^6$=hydrogen;
$R^5$=t-butyl;
$R^4$=in each case one line of Table A.

Table 41

Compounds of the formula I.1, where
$R^6$=hydrogen;
$R^5$=trifluoromethyl;
$R^4$=in each case one line of Table A.

Table 42

Compounds of the formula I.2, where
$R^6$=hydrogen;
$R^5$=trifluoromethyl;
$R^4$=in each case one line of Table A.

Table 43

Compounds of the formula I.3, where
$R^6$=hydrogen;
$R^5$=trifluoromethyl;
$R^4$=in each case one line of Table A.

Table 44

Compounds of the formula I.4, where
$R^6$=hydrogen;
$R^5$=trifluoromethyl;
$R^4$=in each case one line of Table A.

Table 45

Compounds of the formula I.1, where
$R^6$=hydrogen;
$R^5$=pentafluoroethyl;
$R^4$=in each case one line of Table A.

Table 46

Compounds of the formula I.2, where
$R^6$=hydrogen;
$R^5$=pentafluoroethyl;
$R^4$=in each case one line of Table A.

Table 47

Compounds of the formula I.3, where
$R^6$=hydrogen;
$R^5$=pentafluoroethyl;
$R^4$=in each case one line of Table A.

Table 48

Compounds of the formula I.4, where
$R^6$=hydrogen;
$R^5$=pentafluoroethyl;
$R^4$=in each case one line of Table A.

Table 49

Compounds of the formula I.1, where
$R^6$=hydrogen;
$R^5$=cyanomethyl;
$R^4$=in each case one line of Table A.

Table 50

Compounds of the formula I.2, where
$R^6$=hydrogen;
$R^5$=cyanomethyl;
$R^4$=in each case one line of Table A.

Table 51

Compounds of the formula I.3, where
$R^6$=hydrogen;
$R^5$=cyanomethyl;
$R^4$=in each case one line of Table A.

Table 52

Compounds of the formula I.4, where
$R^6$=hydrogen;
$R^5$=cyanomethyl;
$R^4$=in each case one line of Table A.

Table 53

Compounds of the formula I.1, where
$R^6$=hydrogen;
$R^5$=methoxymethyl;
$R^4$=in each case one line of Table A.

Table 54

Compounds of the formula I.2, where
$R^6$=hydrogen;

$R^5$=methoxymethyl;
$R^4$=in each case one line of Table A.

Table 55

Compounds of the formula I.3, where
$R^6$=hydrogen;
$R^5$=methoxymethyl;
$R^4$=in each case one line of Table A.

Table 56

Compounds of the formula I.4, where
$R^6$=hydrogen;
$R^5$=methoxymethyl;
$R^4$=in each case one line of Table A.

Table 57

Compounds of the formula I.1, where
$R^6$=hydrogen;
$R^5$=ethoxymethyl;
$R^4$=in each case one line of Table A.

Table 58

Compounds of the formula I.2, where
$R^6$=hydrogen;
$R^5$=ethoxymethyl;
$R^4$=in each case one line of Table A.

Table 59

Compounds of the formula I.3, where
$R^6$=hydrogen;
$R^5$=ethoxymethyl;
$R^4$=in each case one line of Table A.

Table 60

Compounds of the formula I.4, where
$R^6$=hydrogen;
$R^5$=ethoxymethyl;
$R^4$=in each case one line of Table A.

Table 61

Compounds of the formula I.1, where
$R^6$=hydrogen;
$R^5$=isopropoxymethyl;
$R^4$=in each case one line of Table A.

Table 62

Compounds of the formula I.2, where
$R^6$=hydrogen;
$R^5$=isopropoxymethyl;
$R^4$=in each case one line of Table A.

Table 63

Compounds of the formula I.3, where
$R^6$=hydrogen;
$R^5$=isopropoxymethyl;
$R^4$=in each case one line of Table A.

Table 64

Compounds of the formula I.4, where
$R^6$=hydrogen;
$R^5$=isopropoxymethyl;
$R^4$=in each case one line of Table A.

Table 65

Compounds of the formula I.1, where
$R^6$=hydrogen;
$R^5$=cyclopropylmethyl;
$R^4$=in each case one line of Table A.

Table 66

Compounds of the formula I.2, where
$R^6$=hydrogen;
$R^5$=cyclopropylmethyl;
$R^4$=in each case one line of Table A.

Table 67

Compounds of the formula I.3, where
$R^6$=hydrogen;
$R^5$=cyclopropylmethyl;
$R^4$=in each case one line of Table A.

Table 68

Compounds of the formula I.4, where
$R^6$=hydrogen;
$R^5$=cyclopropylmethyl;
$R^4$=in each case one line of Table A.

Table 69

Compounds of the formula I.1, where
$R^6$=hydrogen;
$R^5$=phenoxymethyl;
$R^4$=in each case one line of Table A.

Table 70

Compounds of the formula I.2, where
$R^6$=hydrogen;
$R^5$=phenoxymethyl;
$R^4$=in each case one line of Table A.

Table 71

Compounds of the formula I.3, where
$R^6$=hydrogen;
$R^5$=phenoxymethyl;
$R^4$=in each case one line of Table A.

Table 72

Compounds of the formula I.4, where
$R^6$=hydrogen;
$R^5$=phenoxymethyl;
$R^4$=in each case one line of Table A.

Table 73

Compounds of the formula I.1, where
$R^6$=hydrogen;
$R^5$=2-chlorophenoxymethyl;
$R^4$=in each case one line of Table A.

Table 74

Compounds of the formula I.2, where
$R^6$=hydrogen;

$R^5$=2-chlorophenoxymethyl;
$R^4$=in each case one line of Table A.

Table 75

Compounds of the formula I.3, where
$R^6$=hydrogen;
$R^5$=2-chlorophenoxymethyl;
$R^4$=in each case one line of Table A.

Table 76

Compounds of the formula I.4, where
$R^6$=hydrogen;
$R^5$=2-chlorophenoxymethyl;
$R^4$=in each case one line of Table A.

Table 77

Compounds of the formula I.1, where
$R^6$=hydrogen;
$R^5$=3-chlorophenoxymethyl;
$R^4$=in each case one line of Table A.

Table 78

Compounds of the formula I.2, where
$R^6$=hydrogen;
$R^5$=3-chlorophenoxymethyl;
$R^4$=in each case one line of Table A.

Table 79

Compounds of the formula I.3, where
$R^6$=hydrogen;
$R^5$=3-chlorophenoxymethyl;
$R^4$=in each case one line of Table A.

Table 80

Compounds of the formula I.4, where
$R^6$=hydrogen;
$R^5$=3-chlorophenoxymethyl;
$R^4$=in each case one line of Table A.

Table 81

Compounds of the formula I.1, where
$R^6$=hydrogen;
$R^5$=4-chlorophenoxymethyl;
$R^4$=in each case one line of Table A.

Table 82

Compounds of the formula I.2, where
$R^6$=hydrogen;
$R^5$=4-chlorophenoxymethyl;
$R^4$=in each case one line of Table A.

Table 83

Compounds of the formula I.3, where
$R^6$=hydrogen;
$R^5$=4-chlorophenoxymethyl;
$R^4$=in each case one line of Table A.

Table 84

Compounds of the formula I.4, where
$R^6$=hydrogen;
$R^5$=4-chlorophenoxymethyl;
$R^4$=in each case one line of Table A.

Table 85

Compounds of the formula I.1, where
$R^6$=hydrogen;
$R^5$=2-cyanophenoxymethyl;
$R^4$=in each case one line of Table A.

Table 86

Compounds of the formula I.2, where
$R^6$=hydrogen;
$R^5$=2-cyanophenoxymethyl;
$R^4$=in each case one line of Table A.

Table 87

Compounds of the formula I.3, where
$R^6$=hydrogen;
$R^5$=2-cyanophenoxymethyl;
$R^4$=in each case one line of Table A.

Table 88

Compounds of the formula I.4, where
$R^6$=hydrogen;
$R^5$=2-cyanophenoxymethyl;
$R^4$=in each case one line of Table A.

Table 89

Compounds of the formula I.1, where
$R^6$=hydrogen;
$R^5$=4-methylphenoxymethyl;
$R^4$=in each case one line of Table A.

Table 90

Compounds of the formula I.2, where
$R^6$=hydrogen;
$R^5$=4-methylphenoxymethyl;
$R^4$=in each case one line of Table A.

Table 91

Compounds of the formula I.3, where
$R^6$=hydrogen;
$R^5$=4-methylphenoxymethyl;
$R^4$=in each case one line of Table A.

Table 92

Compounds of the formula I.4, where
$R^6$=hydrogen;
$R^5$=4-methylphenoxymethyl;
$R^4$=in each case one line of Table A.

Table 93

Compounds of the formula I.1, where
$R^6$=hydrogen;
$R^5$=3-methoxyphenoxymethyl;
$R^4$=in each case one line of Table A.

Table 94

Compounds of the formula I.2, where
$R^6$=hydrogen;

Table 95

Compounds of the formula I.3, where
R$^6$=hydrogen;
R$^5$=3-methoxyphenoxymethyl;
R$^4$=in each case one line of Table A.

Table 96

Compounds of the formula I.4, where
R$^6$=hydrogen;
R$^5$=3-methoxyphenoxymethyl;
R$^4$=in each case one line of Table A.

Table 97

Compounds of the formula I.1, where
R$^6$=hydrogen;
R$^5$=4-trifluoromethylphenoxymethyl;
R$^4$=in each case one line of Table A.

Table 98

Compounds of the formula I.2, where
R$^6$=hydrogen;
R$^5$=4-trifluoromethylphenoxymethyl;
R$^4$=in each case one line of Table A.

Table 99

Compounds of the formula I.3, where
R$^6$=hydrogen;
R$^5$=4-trifluoromethylphenoxymethyl;
R$^4$=in each case one line of Table A.

Table 100

Compounds of the formula I.4, where
R$^6$=hydrogen;
R$^5$=4-trifluoromethylphenoxymethyl;
R$^4$=in each case one line of Table A.

Table 101

Compounds of the formula I.1, where
R$^6$=hydrogen;
R$^5$=2-(3-nitrophenoxy)eth-1-yl;
R$^4$=in each case one line of Table A.

Table 102

Compounds of the formula I.2, where
R$^6$=hydrogen;
R$^5$=2-(3-nitrophenoxy)eth-1-yl;
R$^4$=in each case one line of Table A.

Table 103

Compounds of the formula I.3, where
R$^6$=hydrogen;
R$^5$=2-(3-nitrophenoxy)eth-1-yl;
R$^4$=in each case one line of Table A.

Table 104

Compounds of the formula I.4, where
R$^6$=hydrogen;
R$^5$=2-(3-nitrophenoxy)eth-1-yl;
R$^4$=in each case one line of Table A.

Table 105

Compounds of the formula I.1, where
R$^6$=hydrogen;
R$^5$=2-pyridyloxymethyl;
R$^4$=in each case one line of Table A.

Table 106

Compounds of the formula I.2, where
R$^6$=hydrogen;
R$^5$=2-pyridyloxymethyl;
R$^4$=in each case one line of Table A.

Table 107

Compounds of the formula I.3, where
R$^6$=hydrogen;
R$^5$=2-pyridyloxymethyl;
R$^4$=in each case one line of Table A.

Table 108

Compounds of the formula I.4, where
R$^6$=hydrogen;
R$^5$=2-pyridyloxymethyl;
R$^4$=in each case one line of Table A.

Table 109

Compounds of the formula I.1, where
R$^6$=hydrogen;
R$^5$=4-chloropyrimidin-6-yloxymethyl;
R$^4$=in each case one line of Table A.

Table 110

Compounds of the formula I.2, where
R$^6$=hydrogen;
R$^5$=4-chloropyrimidin-6-yloxymethyl;
R$^4$=in each case one line of Table A.

Table 111

Compounds of the formula I.3, where
R$^6$=hydrogen;
R$^5$=4-chloropyrimidin-6-yloxymethyl;
R$^4$=in each case one line of Table A.

Table 112

Compounds of the formula I.4, where
R$^6$=hydrogen;
R$^5$=4-chloropyrimidin-6-yloxymethyl;
R$^4$=in each case one line of Table A.

Table 113

Compounds of the formula I.1, where
R$^6$=hydrogen;
R$^5$=5-methylisoxazol-3-yloxymethyl;
R$^4$=in each case one line of Table A.

Table 114

Compounds of the formula I.2, where
R$^6$=hydrogen;

Table 115
Compounds of the formula I.3, where
$R^6$=hydrogen;
$R^5$=5-methylisoxazol-3-yloxymethyl;
$R^4$=in each case one line of Table A.

Table 116
Compounds of the formula I.4, where
$R^6$=hydrogen;
$R^5$=5-methylisoxazol-3-yloxymethyl;
$R^4$=in each case one line of Table A.

Table 117
Compounds of the formula I.1, where
$R^6$=hydrogen;
$R^5$=1-phenylpyrazol-3-yloxymethyl;
$R^4$=in each case one line of Table A.

Table 118
Compounds of the formula I.2, where
$R^6$=hydrogen;
$R^5$=1-phenylpyrazol-3-yloxymethyl;
$R^4$=in each case one line of Table A.

Table 119
Compounds of the formula I.3, where
$R^6$=hydrogen;
$R^5$=1-phenylpyrazol-3-yloxymethyl;
$R^4$=in each case one line of Table A.

Table 120
Compounds of the formula I.4, where
$R^6$=hydrogen;
$R^5$=1-phenylpyrazol-3-yloxymethyl;
$R^4$=in each case one line of Table A.

Table 121
Compounds of the formula I.1, where
$R^6$=hydrogen;
$R^5$=3-chloropyrid-6-yloxymethyl;
$R^4$=in each case one line of Table A.

Table 122
Compounds of the formula I.2, where
$R^6$=hydrogen;
$R^5$=3-chloropyrid-6-yloxymethyl;
$R^4$=in each case one line of Table A.

Table 123
Compounds of the formula I.3, where
$R^6$=hydrogen;
$R^5$=3-chloropyrid-6-yloxymethyl;
$R^4$=in each case one line of Table A.

Table 124
Compounds of the formula I.4, where
$R^6$=hydrogen;
$R^5$=3-chloropyrid-6-yloxymethyl;
$R^4$=in each case one line of Table A.

Table 125
Compounds of the formula I.1, where
$R^6$=hydrogen;
$R^5$=2-isopropyloxazol-4-yloxymethyl;
$R^4$=in each case one line of Table A.

Table 126
Compounds of the formula I.2, where
$R^6$=hydrogen;
$R^5$=2-isopropyloxazol-4-yloxymethyl;
$R^4$=in each case one line of Table A.

Table 127
Compounds of the formula I.3, where
$R^6$=hydrogen;
$R^5$=2-isopropyloxazol-4-yloxymethyl;
$R^4$=in each case one line of Table A.

Table 128
Compounds of the formula I.4, where
$R^6$=hydrogen;
$R^5$=2-isopropyloxazol-4-yloxymethyl;
$R^4$=in each case one line of Table A.

Table 129
Compounds of the formula I.1, where
$R^6$=hydrogen;
$R^5$=3-pyridazinyloxymethyl;
$R^4$=in each case one line of Table A.

Table 130
Compounds of the formula I.2, where
$R^6$=hydrogen;
$R^5$=3-pyridazinyloxymethyl;
$R^4$=in each case one line of Table A.

Table 131
Compounds of the formula I.3, where
$R^6$=hydrogen;
$R^5$=3-pyridazinyloxymethyl;
$R^4$=in each case one line of Table A.

Table 132
Compounds of the formula I.4, where
$R^6$=hydrogen;
$R^5$=3-pyridazinyloxymethyl;
$R^4$=in each case one line of Table A.

Table 133
Compounds of the formula I.1, where
$R^6$=hydrogen;
$R^5$=5-methylpyrimidin-2-yloxymethyl;
$R^4$=in each case one line of Table A.

Table 134
Compounds of the formula I.2, where
$R^6$=hydrogen;

$R^5$=5-methylpyrimidin-2-yloxymethyl;
$R^4$=in each case one line of Table A.

Table 135

Compounds of the formula I.3, where
$R^6$=hydrogen;
$R^5$=5-methylpyrimidin-2-yloxymethyl;
$R^4$=in each case one line of Table A.

Table 136

Compounds of the formula I.4, where
$R^6$=hydrogen;
$R^5$=5-methylpyrimidin-2-yloxymethyl;
$R^4$=in each case one line of Table A.

Table 137

Compounds of the formula I.1, where
$R^6$=hydrogen;
$R^5$=ethenyl;
$R^4$=in each case one line of Table A.

Table 138

Compounds of the formula I.2, where
$R^6$=hydrogen;
$R^5$=ethenyl;
$R^4$=in each case one line of Table A.

Table 139

Compounds of the formula I.3, where
$R^6$=hydrogen;
$R^5$=ethenyl;
$R^4$=in each case one line of Table A.

Table 140

Compounds of the formula I.4, where
$R^6$=hydrogen;
$R^5$=ethenyl;
$R^4$=in each case one line of Table A.

Table 141

Compounds of the formula I.1, where
$R^6$=hydrogen;
$R^5$=prop-2-en-1-yl;
$R^4$=in each case one line of Table A.

Table 142

Compounds of the formula I.2, where
$R^6$=hydrogen;
$R^5$=prop-2-en-1-yl;
$R^4$=in each case one line of Table A.

Table 143

Compounds of the formula I.3, where
$R^6$=hydrogen;
$R^5$=prop-2-en-1-yl;
$R^4$=in each case one line of Table A.

Table 144

Compounds of the formula I.4, where
$R^6$=hydrogen;
$R^5$=prop-2-en-1-yl;
$R^4$=in each case one line of Table A.

Table 145

Compounds of the formula I.1, where
$R^6$=hydrogen;
$R^5$=E-3-chloroprop-2-en-1-yl;
$R^4$=in each case one line of Table A.

Table 146

Compounds of the formula I.2, where
$R^6$=hydrogen;
$R^5$=E-3-chloroprop-2-en-1-yl;
$R^4$=in each case one line of Table A.

Table 147

Compounds of the formula I.3, where
$R^6$=hydrogen;
$R^5$=E-3-chloroprop-2-en-1-yl;
$R^4$=in each case one line of Table A.

Table 148

Compounds of the formula I.4, where
$R^6$=hydrogen;
$R^5$=E-3-chloroprop-2-en-1-yl;
$R^4$=in each case one line of Table A.

Table 149

Compounds of the formula I.1, where
$R^6$=hydrogen;
$R^5$=E-but-2-en-1-yl;
$R^4$=in each case one line of Table A.

Table 150

Compounds of the formula I.2, where
$R^6$=hydrogen;
$R^5$=E-but-2-en-1-yl;
$R^4$=in each case one line of Table A.

Table 151

Compounds of the formula I.3, where
$R^6$=hydrogen;
$R^5$=E-but-2-en-1-yl;
$R^4$=in each case one line of Table A.

Table 152

Compounds of the formula I.4, where
$R^6$=hydrogen;
$R^5$=E-but-2-en-1-yl;
$R^4$=in each case one line of Table A.

Table 153

Compounds of the formula I.1, where
$R^6$=hydrogen;
$R^5$=ethynyl;
$R^4$=in each case one line of Table A.

Table 154

Compounds of the formula I.2, where
$R^6$=hydrogen;

Table 155
Compounds of the formula I.3, where
$R^6$=hydrogen;
$R^5$=ethynyl;
$R^4$=in each case one line of Table A.

Table 156
Compounds of the formula I.4, where
$R^6$=hydrogen;
$R^5$=ethynyl;
$R^4$=in each case one line of Table A.

Table 157
Compounds of the formula I.1, where
$R^6$=hydrogen;
$R^5$=prop-2-yn-1-yl;
$R^4$=in each case one line of Table A.

Table 158
Compounds of the formula I.2, where
$R^6$=hydrogen;
$R^5$=prop-2-yn-1-yl;
$R^4$=in each case one line of Table A.

Table 159
Compounds of the formula I.3, where
$R^6$=hydrogen;
$R^5$=prop-2-yn-1-yl;
$R^4$=in each case one line of Table A.

Table 160
Compounds of the formula I.4, where
$R^6$=hydrogen;
$R^5$=prop-2-yn-1-yl;
$R^4$=in each case one line of Table A.

Table 161
Compounds of the formula I.1, where
$R^6$=hydrogen;
$R^5$=prop-1-yn-1-yl;
$R^4$=in each case one line of Table A.

Table 162
Compounds of the formula I.2, where
$R^6$=hydrogen;
$R^5$=prop-1-yn-1-yl;
$R^4$=in each case one line of Table A.

Table 163
Compounds of the formula I.3, where
$R^6$=hydrogen;
$R^5$=prop-1-yn-1-yl;
$R^4$=in each case one line of Table A.

Table 164
Compounds of the formula I.4, where
$R^6$=hydrogen;
$R^5$=prop-1-yn-1-yl;
$R^4$=in each case one line of Table A.

Table 165
Compounds of the formula I.1, where
$R^6$=hydrogen;
$R^5$=phenylethynyl;
$R^4$=in each case one line of Table A.

Table 166
Compounds of the formula I.2, where
$R^6$=hydrogen;
$R^5$=phenylethynyl;
$R^4$=in each case one line of Table A.

Table 167
Compounds of the formula I.3, where
$R^6$=hydrogen;
$R^5$=phenylethynyl;
$R^4$=in each case one line of Table A.

Table 168
Compounds of the formula I.4, where
$R^6$=hydrogen;
$R^5$=phenylethynyl;
$R^4$=in each case one line of Table A.

Table 169
Compounds of the formula I.1, where
$R^6$=hydrogen;
$R^5$=oxiran-2-yl;
$R^4$=in each case one line of Table A.

Table 170
Compounds of the formula I.2, where
$R^6$=hydrogen;
$R^5$=oxiran-2-yl;
$R^4$=in each case one line of Table A.

Table 171
Compounds of the formula I.3, where
$R^6$=hydrogen;
$R^5$=oxiran-2-yl;
$R^4$=in each case one line of Table A.

Table 172
Compounds of the formula I.4, where
$R^6$=hydrogen;
$R^5$=oxiran-2-yl;
$R^4$=in each case one line of Table A.

Table 173
Compounds of the formula I.1, where
$R^6$=hydrogen;
$R^5$=1,1-dichlorocyclopropyl;
$R^4$=in each case one line of Table A.

Table 174
Compounds of the formula I.2, where
$R^6$=hydrogen;

$R^5$=1,1-dichlorocyclopropyl;
$R^4$=in each case one line of Table A.

Table 175

Compounds of the formula I.3, where
$R^6$=hydrogen;
$R^5$=1,1-dichlorocyclopropyl;
$R^4$=in each case one line of Table A.

Table 176

Compounds of the formula I.4, where
$R^6$=hydrogen;
$R^5$=1,1-dichlorocyclopropyl;
$R^4$=in each case one line of Table A.

Table 177

Compounds of the formula I.1, where
$R^6$=hydrogen;
$R^5$=phenyl;
$R^4$=in each case one line of Table A.

Table 178

Compounds of the formula I.2, where
$R^6$=hydrogen;
$R^5$=phenyl;
$R^4$=in each case one line of Table A.

Table 179

Compounds of the formula I.3, where
$R^6$=hydrogen;
$R^5$=phenyl;
$R^4$=in each case one line of Table A.

Table 180

Compounds of the formula I.4, where
$R^6$=hydrogen;
$R^5$=phenyl;
$R^4$=in each case one line of Table A.

Table 181

Compounds of the formula I.1, where
$R^6$=hydrogen;
$R^5$=2-naphthyl;
$R^4$=in each case one line of Table A.

Table 182

Compounds of the formula I.2, where
$R^6$=hydrogen;
$R^5$=2-naphthyl;
$R^4$=in each case one line of Table A.

Table 183

Compounds of the formula I.3, where
$R^6$=hydrogen;
$R^5$=2-naphthyl;
$R^4$=in each case one line of Table A.

Table 184

Compounds of the formula I.4, where
$R^6$=hydrogen;
$R^5$=2-naphthyl;
$R^4$=in each case one line of Table A.

Table 185

Compounds of the formula I.1, where
$R^6$=hydrogen;
$R^5$=2-chlorophenyl;
$R^4$=in each case one line of Table A.

Table 186

Compounds of the formula I.2, where
$R^6$=hydrogen;
$R^5$=2-chlorophenyl;
$R^4$=in each case one line of Table A.

Table 187

Compounds of the formula I.3, where
$R^6$=hydrogen;
$R^5$=2-chlorophenyl;
$R^4$=in each case one line of Table A.

Table 188

Compounds of the formula I.4, where
$R^6$=hydrogen;
$R^5$=2-chlorophenyl;
$R^4$=in each case one line of Table A.

Table 189

Compounds of the formula I.1, where
$R^6$=hydrogen;
$R^5$=3-chlorophenyl;
$R^4$=in each case one line of Table A.

Table 190

Compounds of the formula I.2, where
$R^6$=hydrogen;
$R^5$=3-chlorophenyl;
$R^4$=in each case one line of Table A.

Table 191

Compounds of the formula I.3, where
$R^6$=hydrogen;
$R^5$=3-chlorophenyl;
$R^4$=in each case one line of Table A.

Table 192

Compounds of the formula I.4, where
$R^6$=hydrogen;
$R^5$=3-chlorophenyl;
$R^4$=in each case one line of Table A.

Table 193

Compounds of the formula I.1, where
$R^6$=hydrogen;
$R^5$=4-chlorophenyl;
$R^4$=in each case one line of Table A.

Table 194

Compounds of the formula I.2, where
$R^6$=hydrogen;

$R^5$=4-chlorophenyl;
$R^4$=in each case one line of Table A.

Table 195

Compounds of the formula I.3, where
$R^6$=hydrogen;
$R^5$=4-chlorophenyl;
$R^4$=in each case one line of Table A.

Table 196

Compounds of the formula I.4, where
$R^6$=hydrogen;
$R^5$=4-chlorophenyl;
$R^4$=in each case one line of Table A.

Table 197

Compounds of the formula I.1, where
$R^6$=hydrogen;
$R^5$=2-nitrophenyl;
$R^4$=in each case one line of Table A.

Table 198

Compounds of the formula I.2, where
$R^6$=hydrogen;
$R^5$=2-nitrophenyl;
$R^4$=in each case one line of Table A.

Table 199

Compounds of the formula I.3, where
$R^6$=hydrogen;
$R^5$=2-nitrophenyl;
$R^4$=in each case one line of Table A.

Table 200

Compounds of the formula I.4, where
$R^6$=hydrogen;
$R^5$=2-nitrophenyl;
$R^4$=in each case one line of Table A.

Table 201

Compounds of the formula I.1, where
$R^6$=hydrogen;
$R^5$=3-cyanophenyl;
$R^4$=in each case one line of Table A.

Table 202

Compounds of the formula I.2, where
$R^6$=hydrogen;
$R^5$=3-cyanophenyl;
$R^4$=in each case one line of Table A.

Table 203

Compounds of the formula I.3, where
$R^6$=hydrogen;
$R^5$=3-cyanophenyl;
$R^4$=in each case one line of Table A.

Table 204

Compounds of the formula I.4, where
$R^6$=hydrogen;
$R^5$=3-cyanophenyl;
$R^4$=in each case one line of Table A.

Table 205

Compounds of the formula I.1, where
$R^6$=hydrogen;
$R^5$=4-methylphenyl;
$R^4$=in each case one line of Table A.

Table 206

Compounds of the formula I.2, where
$R^6$=hydrogen;
$R^5$=4-methylphenyl;
$R^4$=in each case one line of Table A.

Table 207

Compounds of the formula I.3, where
$R^6$=hydrogen;
$R^5$=4-methylphenyl;
$R^4$=in each case one line of Table A.

Table 208

Compounds of the formula I.4, where
$R^6$=hydrogen;
$R^5$=4-methylphenyl;
$R^4$=in each case one line of Table A.

Table 209

Compounds of the formula I.1, where
$R^6$=hydrogen;
$R^5$=3-tert-butylphenyl;
$R^4$=in each case one line of Table A.

Table 210

Compounds of the formula I.2, where
$R^6$=hydrogen;
$R^5$=3-tert-butylphenyl;
$R^4$=in each case one line of Table A.

Table 211

Compounds of the formula I.3, where
$R^6$=hydrogen;
$R^5$=3-tert-butylphenyl;
$R^4$=in each case one line of Table A.

Table 212

Compounds of the formula I.4, where
$R^6$=hydrogen;
$R^5$=3-tert-butylphenyl;
$R^4$=in each case one line of Table A.

Table 213

Compounds of the formula I.1, where
$R^6$=hydrogen;
$R^5$=4-trifluoromethylphenyl;
$R^4$=in each case one line of Table A.

Table 214

Compounds of the formula I.2, where
$R^6$=hydrogen;

R⁵=4-trifluoromethylphenyl;
R⁴=in each case one line of Table A.

Table 215

Compounds of the formula I.3, where
R⁶=hydrogen;
R⁵=4-trifluoromethylphenyl;
R⁴=in each case one line of Table A.

Table 216

Compounds of the formula I.4, where
R⁶=hydrogen;
R⁵=4-trifluoromethylphenyl;
R⁴=in each case one line of Table A.

Table 217

Compounds of the formula I.1, where
R⁶=hydrogen;
R⁵=2-methoxyphenyl;
R⁴=in each case one line of Table A.

Table 218

Compounds of the formula I.2, where
R⁶=hydrogen;
R⁵=2-methoxyphenyl;
R⁴=in each case one line of Table A.

Table 219

Compounds of the formula I.3, where
R⁶=hydrogen;
R⁵=2-methoxyphenyl;
R⁴=in each case one line of Table A.

Table 220

Compounds of the formula I.4, where
R⁶=hydrogen;
R⁵=2-methoxyphenyl;
R⁴=in each case one line of Table A.

Table 221

Compounds of the formula I.1, where
R⁶=hydrogen;
R⁵=2,4-dichlorophenyl;
R⁴=in each case one line of Table A.

Table 222

Compounds of the formula I.2, where
R⁶=hydrogen;
R⁵=2,4-dichlorophenyl;
R⁴=in each case one line of Table A.

Table 223

Compounds of the formula I.3, where
R⁶=hydrogen;
R⁵=2,4-dichlorophenyl;
R⁴=in each case one line of Table A.

Table 224

Compounds of the formula I.4, where
R⁶=hydrogen;
R⁵=2,4-dichlorophenyl;
R⁴=in each case one line of Table A.

Table 225

Compounds of the formula I.1, where
R⁶=hydrogen;
R⁵=4-fluorophenyl;
R⁴=in each case one line of Table A.

Table 226

Compounds of the formula I.2, where
R⁶=hydrogen;
R⁵=4-fluorophenyl;
R⁴=in each case one line of Table A.

Table 227

Compounds of the formula I.3, where
R⁶=hydrogen;
R⁵=4-fluorophenyl;
R⁴=in each case one line of Table A.

Table 228

Compounds of the formula I.4, where
R⁶=hydrogen;
R⁵=4-fluorophenyl;
R⁴=in each case one line of Table A.

Table 229

Compounds of the formula I.1, where
R⁶=hydrogen;
R⁵=2-pyridyl;
R⁴=in each case one line of Table A.

Table 230

Compounds of the formula I.2, where
R⁶=hydrogen;
R⁵=2-pyridyl;
R⁴=in each case one line of Table A.

Table 231

Compounds of the formula I.3, where
R⁶=hydrogen;
R⁵=2-pyridyl;
R⁴=in each case one line of Table A.

Table 232

Compounds of the formula I.4, where
R⁶=hydrogen;
R⁵=2-pyridyl;
R⁴=in each case one line of Table A.

Table 233

Compounds of the formula I.1, where
R⁶=hydrogen;
R⁵=2-chloropyridin-6-yl;
R⁴=in each case one line of Table A.

Table 234

Compounds of the formula I.2, where
R⁶=hydrogen;

$R^5$=2-chloropyridin-6-yl;
$R^4$=in each case one line of Table A.

Table 235

Compounds of the formula I.3, where
$R^6$=hydrogen;
$R^5$=2-chloropyridin-6-yl;
$R^4$=in each case one line of Table A.

Table 236

Compounds of the formula I.4, where
$R^6$=hydrogen;
$R^5$=2-chloropyridin-6-yl;
$R^4$=in each case one line of Table A.

Table 237

Compounds of the formula I.1, where
$R^6$=hydrogen;
$R^5$=5-methylpyrimidin-2-yl;
$R^4$=in each case one line of Table A.

Table 238

Compounds of the formula I.2, where
$R^6$=hydrogen;
$R^5$=5-methylpyrimidin-2-yl;
$R^4$=in each case one line of Table A.

Table 239

Compounds of the formula I.3, where
$R^6$=hydrogen;
$R^5$=5-methylpyrimidin-2-yl;
$R^4$=in each case one line of Table A.

Table 240

Compounds of the formula I.4, where
$R^6$=hydrogen;
$R^5$=5-methylpyrimidin-2-yl;
$R^4$=in each case one line of Table A.

Table 241

Compounds of the formula I.1, where
$R^6$=hydrogen;
$R^5$=2-chloropyridin-5-yl;
$R^4$=in each case one line of Table A.

Table 242

Compounds of the formula I.2, where
$R^6$=hydrogen;
$R^5$=2-chloropyridin-5-yl;
$R^4$=in each case one line of Table A.

Table 243

Compounds of the formula I.3, where
$R^6$=hydrogen;
$R^5$=2-chloropyridin-5-yl;
$R^4$=in each case one line of Table A.

Table 244

Compounds of the formula I.4, where
$R^6$=hydrogen;
$R^5$=2-chloropyridin-5-yl;
$R^4$=in each case one line of Table A.

Table 245

Compounds of the formula I.1, where
$R^6$=hydrogen;
$R^5$=5-cyanothien-2-yl;
$R^4$=in each case one line of Table A.

Table 246

Compounds of the formula I.2, where
$R^6$=hydrogen;
$R^5$=5-cyanothien-2-yl;
$R^4$=in each case one line of Table A.

Table 247

Compounds of the formula I.3, where
$R^6$=hydrogen;
$R^5$=5-cyanothien-2-yl;
$R^4$=in each case one line of Table A.

Table 248

Compounds of the formula I.4, where
$R^6$=hydrogen;
$R^5$=5-cyanothien-2-yl;
$R^4$=in each case one line of Table A.

Table 249

Compounds of the formula I.1, where
$R^6$=hydrogen;
$R^5$=4-chlorooxazol-2-yl;
$R^4$=in each case one line of Table A.

Table 250

Compounds of the formula I.2, where
$R^6$=hydrogen;
$R^5$=4-chlorooxazol-2-yl;
$R^4$=in each case one line of Table A.

Table 251

Compounds of the formula I.3, where
$R^6$=hydrogen;
$R^5$=4-chlorooxazol-2-yl;
$R^4$=in each case one line of Table A.

Table 252

Compounds of the formula I.4, where
$R^6$=hydrogen;
$R^5$=4-chlorooxazol-2-yl;
$R^4$=in each case one line of Table A.

Table 253

Compounds of the formula I.1, where
$R^6$=hydrogen;
$R^5$=1-methylpyrazol-3-yl;
$R^4$=in each case one line of Table A.

Table 254

Compounds of the formula I.2, where
$R^6$=hydrogen;

$R^5$=1-methylpyrazol-3-yl;
$R^4$=in each case one line of Table A.

Table 255

Compounds of the formula I.3, where
$R^6$=hydrogen;
$R^5$=1-methylpyrazol-3-yl;
$R^4$=in each case one line of Table A.

Table 256

Compounds of the formula I.4, where
$R^6$=hydrogen;
$R^5$=1-methylpyrazol-3-yl;
$R^4$=in each case one line of Table A.

Table 257

Compounds of the formula I.1, where
$R^6$=hydrogen;
$R^5$=5-trifluoromethyl-1,2,4-oxadiazol-3-yl;
$R^4$=in each case one line of Table A.

Table 258

Compounds of the formula I.2, where
$R^6$=hydrogen;
$R^5$=5-trifluoromethyl-1,2,4-oxadiazol-3-yl;
$R^4$=in each case one line of Table A.

Table 259

Compounds of the formula I.3, where
$R^6$=hydrogen;
$R^5$=5-trifluoromethyl-1,2,4-oxadiazol-3-yl;
$R^4$=in each case one line of Table A.

Table 260

Compounds of the formula I.4, where
$R^6$=hydrogen;
$R^5$=5-trifluoromethyl-1,2,4-oxadiazol-3-yl;
$R^4$=in each case one line of Table A.

Table 261

Compounds of the formula I.1, where
$R^6$=methyl;
$R^5$=n-hexyl;
$R^4$=in each case one line of Table A.

Table 262

Compounds of the formula I.2, where
$R^6$=methyl;
$R^5$=n-hexyl;
$R^4$=in each case one line of Table A.

Table 263

Compounds of the formula I.3, where
$R^6$=methyl;
$R^5$=n-hexyl;
$R^4$=in each case one line of Table A.

Table 264

Compounds of the formula I.4, where
$R^6$=methyl;
$R^5$=n-hexyl;
$R^4$=in each case one line of Table A.

Table 265

Compounds of the formula I.1, where
$R^6$=methyl;
$R^5$=methyl;
$R^4$=in each case one line of Table A.

Table 266

Compounds of the formula I.2, where
$R^6$=methyl;
$R^5$=methyl;
$R^4$=in each case one line of Table A.

Table 267

Compounds of the formula I.3, where
$R^6$=methyl;
$R^5$=methyl;
$R^4$=in each case one line of Table A.

Table 268

Compounds of the formula I.4, where
$R^6$=methyl;
$R^5$=methyl;
$R^4$=in each case one line of Table A.

Table 269

Compounds of the formula I.1, where
$R^6$=methyl;
$R^5$=ethyl;
$R^4$=in each case one line of Table A.

Table 270

Compounds of the formula I.2, where
$R^6$=methyl;
$R^5$=ethyl;
$R^4$=in each case one line of Table A.

Table 271

Compounds of the formula I.3, where
$R^6$=methyl;
$R^5$=ethyl;
$R^4$=in each case one line of Table A.

Table 272

Compounds of the formula I.4, where
$R^6$=methyl;
$R^5$=ethyl;
$R^4$=in each case one line of Table A.

Table 273

Compounds of the formula I.1, where
$R^6$=methyl;
$R^5$=n-propyl;
$R^4$=in each case one line of Table A.

Table 274

Compounds of the formula I.2, where
$R^6$=methyl;

$R^5$=n-propyl;
$R^4$=in each case one line of Table A.

Table 275

Compounds of the formula I.3, where
$R^6$=methyl;
$R^5$=n-propyl;
$R^4$=in each case one line of Table A.

Table 276

Compounds of the formula I.4, where
$R^6$=methyl;
$R^5$=n-propyl;
$R^4$=in each case one line of Table A.

Table 277

Compounds of the formula I.1, where
$R^6$=methyl;
$R^5$=isopropyl;
$R^4$=in each case one line of Table A.

Table 278

Compounds of the formula I.2, where
$R^6$=methyl;
$R^5$=isopropyl;
$R^4$=in each case one line of Table A.

Table 279

Compounds of the formula I.3, where
$R^6$=methyl;
$R^5$=isopropyl;
$R^4$=in each case one line of Table A.

Table 280

Compounds of the formula I.4, where
$R^6$=methyl;
$R^5$=isopropyl;
$R^4$=in each case one line of Table A.

Table 281

Compounds of the formula I.1, where
$R^6$=methyl;
$R^5$=cyclopropyl;
$R^4$=in each case one line of Table A.

Table 282

Compounds of the formula I.2, where
$R^6$=methyl;
$R^5$=cyclopropyl;
$R^4$=in each case one line of Table A.

Table 283

Compounds of the formula I.3, where
$R^6$=methyl;
$R^5$=cyclopropyl;
$R^4$=in each case one line of Table A.

Table 284

Compounds of the formula I.4, where
$R^6$=methyl;
$R^5$=cyclopropyl;
$R^4$=in each case one line of Table A.

Table 285

Compounds of the formula I.1, where
$R^6$=methyl;
$R^5$=n-butyl;
$R^4$=in each case one line of Table A.

Table 286

Compounds of the formula I.2, where
$R^6$=methyl;
$R^5$=n-butyl;
$R^4$=in each case one line of Table A.

Table 287

Compounds of the formula I.3, where
$R^6$=methyl;
$R^5$=n-butyl;
$R^4$=in each case one line of Table A.

Table 288

Compounds of the formula I.4, where
$R^6$=methyl;
$R^5$=n-butyl;
$R^4$=in each case one line of Table A.

Table 289

Compounds of the formula I.1, where
$R^6$=methyl;
$R^5$=isobutyl;
$R^4$=in each case one line of Table A.

Table 290

Compounds of the formula I.2, where
$R^6$=methyl;
$R^5$=isobutyl;
$R^4$=in each case one line of Table A.

Table 291

Compounds of the formula I.3, where
$R^6$=methyl;
$R^5$=isobutyl;
$R^4$=in each case one line of Table A.

Table 292

Compounds of the formula I.4, where
$R^6$=methyl;
$R^5$=isobutyl;
$R^4$=in each case one line of Table A.

Table 293

Compounds of the formula I.1, where
$R^6$=methyl;
$R^5$=sec-butyl;
$R^4$=in each case one line of Table A.

Table 294

Compounds of the formula I.2, where
$R^6$=methyl;

$R^5$=sec-butyl;
$R^4$=in each case one line of Table A.

Table 295

Compounds of the formula I.3, where
$R^6$=methyl;
$R^5$=sec-butyl;
$R^4$=in each case one line of Table A.

Table 296

Compounds of the formula I.4, where
$R^6$=methyl;
$R^5$=sec-butyl;
$R^4$=in each case one line of Table A.

Table 297

Compounds of the formula I.1, where
$R^6$=methyl;
$R^5$=tert-butyl;
$R^4$=in each case one line of Table A.

Table 298

Compounds of the formula I.2, where
$R^6$=methyl;
$R^5$=tert-butyl;
$R^4$=in each case one line of Table A.

Table 299

Compounds of the formula I.3, where
$R^6$=methyl;
$R^5$=tert-butyl;
$R^4$=in each case one line of Table A.

Table 300

Compounds of the formula I.4, where
$R^6$=methyl;
$R^5$=tert-butyl;
$R^4$=in each case one line of Table A.

Table 301

Compounds of the formula I.1, where
$R^6$=methyl;
$R^5$=trifluoromethyl;
$R^4$=in each case one line of Table A.

Table 302

Compounds of the formula I.2, where
$R^6$=methyl;
$R^5$=trifluoromethyl;
$R^4$=in each case one line of Table A.

Table 303

Compounds of the formula I.3, where
$R^6$=methyl;
$R^5$=trifluoromethyl;
$R^4$=in each case one line of Table A.

Table 304

Compounds of the formula I.4, where
$R^6$=methyl;
$R^5$=trifluoromethyl;
$R^4$=in each case one line of Table A.

Table 305

Compounds of the formula I.1, where
$R^6$=methyl;
$R^5$=pentafluoroethyl;
$R^4$=in each case one line of Table A.

Table 306

Compounds of the formula I.2, where
$R^6$=methyl;
$R^5$=pentafluoroethyl;
$R^4$=in each case one line of Table A.

Table 307

Compounds of the formula I.3, where
$R^6$=methyl;
$R^5$=pentafluoroethyl;
$R^4$=in each case one line of Table A.

Table 308

Compounds of the formula I.4, where
$R^6$=methyl;
$R^5$=pentafluoroethyl;
$R^4$=in each case one line of Table A.

Table 309

Compounds of the formula I.1, where
$R^6$=methyl;
$R^5$=cyanomethyl;
$R^4$=in each case one line of Table A.

Table 310

Compounds of the formula I.2, where
$R^6$=methyl;
$R^5$=cyanomethyl;
$R^4$=in each case one line of Table A.

Table 311

Compounds of the formula I.3, where
$R^6$=methyl;
$R^5$=cyanomethyl;
$R^4$=in each case one line of Table A.

Table 312

Compounds of the formula I.4, where
$R^6$=methyl;
$R^5$=cyanomethyl;
$R^4$=in each case one line of Table A.

Table 313

Compounds of the formula I.1, where
$R^6$=methyl;
$R^5$=methoxymethyl;
$R^4$=in each case one line of Table A.

Table 314

Compounds of the formula I.2, where
$R^6$=methyl;

$R^5$=methoxymethyl;
$R^4$=in each case one line of Table A.

Table 315

Compounds of the formula I.3, where
$R^6$=methyl;
$R^5$=methoxymethyl;
$R^4$=in each case one line of Table A.

Table 316

Compounds of the formula I.4, where
$R^6$=methyl;
$R^5$=methoxymethyl;
$R^4$=in each case one line of Table A.

Table 317

Compounds of the formula I.1, where
$R^6$=methyl;
$R^5$=ethoxymethyl;
$R^4$=in each case one line of Table A.

Table 318

Compounds of the formula I.2, where
$R^6$=methyl;
$R^5$=ethoxymethyl;
$R^4$=in each case one line of Table A.

Table 319

Compounds of the formula I.3, where
$R^6$=methyl;
$R^5$=ethoxymethyl;
$R^4$=in each case one line of Table A.

Table 320

Compounds of the formula I.4, where
$R^6$=methyl;
$R^5$=ethoxymethyl;
$R^4$=in each case one line of Table A.

Table 321

Compounds of the formula I.1, where
$R^6$=methyl;
$R^5$=isopropoxymethyl;
$R^4$=in each case one line of Table A.

Table 322

Compounds of the formula I.2, where
$R^6$=methyl;
$R^5$=isopropoxymethyl;
$R^4$=in each case one line of Table A.

Table 323

Compounds of the formula I.3, where
$R^6$=methyl;
$R^5$=isopropoxymethyl;
$R^4$=in each case one line of Table A.

Table 324

Compounds of the formula I.4, where
$R^6$=methyl;
$R^5$=isopropoxymethyl;
$R^4$=in each case one line of Table A.

Table 325

Compounds of the formula I.1, where
$R^6$=methyl;
$R^5$=cyclopropylmethyl;
$R^4$=in each case one line of Table A.

Table 326

Compounds of the formula I.2, where
$R^6$=methyl;
$R^5$=cyclopropylmethyl;
$R^4$=in each case one line of Table A.

Table 327

Compounds of the formula I.3, where
$R^6$=methyl;
$R^5$=cyclopropylmethyl;
$R^4$=in each case one line of Table A.

Table 328

Compounds of the formula I.4, where
$R^6$=methyl;
$R^5$=cyclopropylmethyl;
$R^4$=in each case one line of Table A.

Table 329

Compounds of the formula I.1, where
$R^6$=methyl;
$R^5$=phenoxymethyl;
$R^4$=in each case one line of Table A.

Table 330

Compounds of the formula I.2, where
$R^6$=methyl;
$R^5$=phenoxymethyl;
$R^4$=in each case one line of Table A.

Table 331

Compounds of the formula I.3, where
$R^6$=methyl;
$R^5$=phenoxymethyl;
$R^4$=in each case one line of Table A.

Table 332

Compounds of the formula I.4, where
$R^6$=methyl;
$R^5$=phenoxymethyl;
$R^4$=in each case one line of Table A.

Table 333

Compounds of the formula I.1, where
$R^6$=methyl;
$R^5$=2-chlorophenoxymethyl;
$R^4$=in each case one line of Table A.

Table 334

Compounds of the formula I.2, where
$R^6$=methyl;

$R^5$=2-chlorophenoxymethyl;
$R^4$=in each case one line of Table A.

Table 335

Compounds of the formula I.3, where
$R^6$=methyl;
$R^5$=2-chlorophenoxymethyl;
$R^4$=in each case one line of Table A.

Table 336

Compounds of the formula I.4, where
$R^6$=methyl;
$R^5$=2-chlorophenoxymethyl;
$R^4$=in each case one line of Table A.

Table 337

Compounds of the formula I.1, where
$R^6$=methyl;
$R^5$=3-chlorophenoxymethyl;
$R^4$=in each case one line of Table A.

Table 338

Compounds of the formula I.2, where
$R^6$=methyl;
$R^5$=3-chlorophenoxymethyl;
$R^4$=in each case one line of Table A.

Table 339

Compounds of the formula I.3, where
$R^6$=methyl;
$R^5$=3-chlorophenoxymethyl;
$R^4$=in each case one line of Table A.

Table 340

Compounds of the formula I.4, where
$R^6$=methyl;
$R^5$=3-chlorophenoxymethyl;
$R^4$=in each case one line of Table A.

Table 341

Compounds of the formula I.1, where
$R^6$=methyl;
$R^5$=4-chlorophenoxymethyl;
$R^4$=in each case one line of Table A.

Table 342

Compounds of the formula I.2, where
$R^6$=methyl;
$R^5$=4-chlorophenoxymethyl;
$R^4$=in each case one line of Table A.

Table 343

Compounds of the formula I.3, where
$R^6$=methyl;
$R^5$=4-chlorophenoxymethyl;
$R^4$=in each case one line of Table A.

Table 344

Compounds of the formula I.4, where
$R^6$=methyl;
$R^5$=4-chlorophenoxymethyl;
$R^4$=in each case one line of Table A.

Table 345

Compounds of the formula I.1, where
$R^6$=methyl;
$R^5$=2-cyanophenoxymethyl;
$R^4$=in each case one line of Table A.

Table 346

Compounds of the formula I.2, where
$R^6$=methyl;
$R^5$=2-cyanophenoxymethyl;
$R^4$=in each case one line of Table A.

Table 347

Compounds of the formula I.3, where
$R^6$=methyl;
$R^5$=2-cyanophenoxymethyl;
$R^4$=in each case one line of Table A.

Table 348

Compounds of the formula I.4, where
$R^6$=methyl;
$R^5$=2-cyanophenoxymethyl;
$R^4$=in each case one line of Table A.

Table 349

Compounds of the formula I.1, where
$R^6$=methyl;
$R^5$=4-methylphenoxymethyl;
$R^4$=in each case one line of Table A.

Table 350

Compounds of the formula I.2, where
$R^6$=methyl;
$R^5$=4-methylphenoxymethyl;
$R^4$=in each case one line of Table A.

Table 351

Compounds of the formula I.3, where
$R^6$=methyl;
$R^5$=4-methylphenoxymethyl;
$R^4$=in each case one line of Table A.

Table 352

Compounds of the formula I.4, where
$R^6$=methyl;
$R^5$=4-methylphenoxymethyl;
$R^4$=in each case one line of Table A.

Table 353

Compounds of the formula I.1, where
$R^6$=methyl;
$R^5$=3-methoxyphenoxymethyl;
$R^4$=in each case one line of Table A.

Table 354

Compounds of the formula I.2, where
$R^6$=methyl;

$R^5$=3-methoxyphenoxymethyl;
$R^4$=in each case one line of Table A.

Table 355

Compounds of the formula I.3, where
$R^6$=methyl;
$R^5$=3-methoxyphenoxymethyl;
$R^4$=in each case one line of Table A.

Table 356

Compounds of the formula I.4, where
$R^6$=methyl;
$R^5$=3-methoxyphenoxymethyl;
$R^4$=in each case one line of Table A.

Table 357

Compounds of the formula I.1, where
$R^6$=methyl;
$R^5$=4-trifluoromethylphenoxymethyl;
$R^4$=in each case one line of Table A.

Table 358

Compounds of the formula I.2, where
$R^6$=methyl;
$R^5$=4-trifluoromethylphenoxymethyl;
$R^4$=in each case one line of Table A.

Table 359

Compounds of the formula I.3, where
$R^6$=methyl;
$R^5$=4-trifluoromethylphenoxymethyl;
$R^4$=in each case one line of Table A.

Table 360

Compounds of the formula I.4, where
$R^6$=methyl;
$R^5$=4-trifluoromethylphenoxymethyl;
$R^4$=in each case one line of Table A.

Table 361

Compounds of the formula I.1, where
$R^6$=methyl;
$R^5$=2-(3-nitrophenoxy)eth-1-yl;
$R^4$=in each case one line of Table A.

Table 362

Compounds of the formula I.2, where
$R^6$=methyl;
$R^5$=2-(3-nitrophenoxy)eth-1-yl;
$R^4$=in each case one line of Table A.

Table 363

Compounds of the formula I.3, where
$R^6$=methyl;
$R^5$=2-(3-nitrophenoxy)eth-1-yl;
$R^4$=in each case one line of Table A.

Table 364

Compounds of the formula I.4, where
$R^6$=methyl;
$R^5$=2-(3-nitrophenoxy)eth-1-yl;
$R^4$=in each case one line of Table A.

Table 365

Compounds of the formula I.1, where
$R^6$=methyl;
$R^5$=2-pyridyloxymethyl;
$R^4$=in each case one line of Table A.

Table 366

Compounds of the formula I.2, where
$R^6$=methyl;
$R^5$=2-pyridyloxymethyl;
$R^4$=in each case one line of Table A.

Table 367

Compounds of the formula I.3, where
$R^6$=methyl;
$R^5$=2-pyridyloxymethyl;
$R^4$=in each case one line of Table A.

Table 368

Compounds of the formula I.4, where
$R^6$=methyl;
$R^5$=2-pyridyloxymethyl;
$R^4$=in each case one line of Table A.

Table 369

Compounds of the formula I.1, where
$R^6$=methyl;
$R^5$=4-chloropyrimidin-6-yloxymethyl;
$R^4$=in each case one line of Table A.

Table 370

Compounds of the formula I.2, where
$R^6$=methyl;
$R^5$=4-chloropyrimidin-6-yloxymethyl;
$R^4$=in each case one line of Table A.

Table 371

Compounds of the formula I.3, where
$R^6$=methyl;
$R^5$=4-chloropyrimidin-6-yloxymethyl;
$R^4$=in each case one line of Table A.

Table 372

Compounds of the formula I.4, where
$R^6$=methyl;
$R^5$=4-chloropyrimidin-6-yloxymethyl;
$R^4$=in each case one line of Table A.

Table 373

Compounds of the formula I.1, where
$R^6$=methyl;
$R^5$=5-methylisoxazol-3-yloxymethyl;
$R^4$=in each case one line of Table A.

Table 374

Compounds of the formula I.2, where
$R^6$=methyl;

$R^5$=5-methylisoxazol-3-yloxymethyl;
$R^4$=in each case one line of Table A.

Table 375

Compounds of the formula I.3, where
$R^6$=methyl;
$R^5$=5-methylisoxazol-3-yloxymethyl;
$R^4$=in each case one line of Table A.

Table 376

Compounds of the formula I.4, where
$R^6$=methyl;
$R^5$=5-methylisoxazol-3-yloxymethyl;
$R^4$=in each case one line of Table A.

Table 377

Compounds of the formula I.1, where
$R^6$=methyl;
$R^5$=1-phenylpyrazol-3-yloxymethyl;
$R^4$=in each case one line of Table A.

Table 378

Compounds of the formula I.2, where
$R^6$=methyl;
$R^5$=1-phenylpyrazol-3-yloxymethyl;
$R^4$=in each case one line of Table A.

Table 379

Compounds of the formula I.3, where
$R^6$=methyl;
$R^5$=1-phenylpyrazol-3-yloxymethyl;
$R^4$=in each case one line of Table A.

Table 380

Compounds of the formula I.4, where
$R^6$=methyl;
$R^5$=1-phenylpyrazol-3-yloxymethyl;
$R^4$=in each case one line of Table A.

Table 381

Compounds of the formula I.1, where
$R^6$=methyl;
$R^5$=3-chloropyrid-6-yloxymethyl;
$R^4$=in each case one line of Table A.

Table 382

Compounds of the formula I.2, where
$R^6$=methyl;
$R^5$=3-chloropyrid-6-yloxymethyl;
$R^4$=in each case one line of Table A.

Table 383

Compounds of the formula I.3, where
$R^6$=methyl;
$R^5$=3-chloropyrid-6-yloxymethyl;
$R^4$=in each case one line of Table A.

Table 384

Compounds of the formula I.4, where
$R^6$=methyl;
$R^5$=3-chloropyrid-6-yloxymethyl;
$R^4$=in each case one line of Table A.

Table 385

Compounds of the formula I.1, where
$R^6$=methyl;
$R^5$=2-isopropyloxazol-4-yloxymethyl;
$R^4$=in each case one line of Table A.

Table 386

Compounds of the formula I.2, where
$R^6$=methyl;
$R^5$=2-isopropyloxazol-4-yloxymethyl;
$R^4$=in each case one line of Table A.

Table 387

Compounds of the formula I.3, where
$R^6$=methyl;
$R^5$=2-isopropyloxazol-4-yloxymethyl;
$R^4$=in each case one line of Table A.

Table 388

Compounds of the formula I.4, where
$R^6$=methyl;
$R^5$=2-isopropyloxazol-4-yloxymethyl;
$R^4$=in each case one line of Table A.

Table 389

Compounds of the formula I.1, where
$R^6$=methyl;
$R^5$=3-pyridazinyloxymethyl;
$R^4$=in each case one line of Table A.

Table 390

Compounds of the formula I.2, where
$R^6$=methyl;
$R^5$=3-pyridazinyloxymethyl;
$R^4$=in each case one line of Table A.

Table 391

Compounds of the formula I.3, where
$R^6$=methyl;
$R^5$=3-pyridazinyloxymethyl;
$R^4$=in each case one line of Table A.

Table 392

Compounds of the formula I.4, where
$R^6$=methyl;
$R^5$=3-pyridazinyloxymethyl;
$R^4$=in each case one line of Table A.

Table 393

Compounds of the formula I.1, where
$R^6$=methyl;
$R^5$=5-methylpyrimidin-2-yloxymethyl;
$R^4$=in each case one line of Table A.

Table 394

Compounds of the formula I.2, where
$R^6$=methyl;

R⁵=5-methylpyrimidin-2-yloxymethyl;
R⁴=in each case one line of Table A.

Table 395

Compounds of the formula I.3, where
R⁶=methyl;
R⁵=5-methylpyrimidin-2-yloxymethyl;
R⁴=in each case one line of Table A.

Table 396

Compounds of the formula I.4, where
R⁶=methyl;
R⁵=5-methylpyrimidin-2-yloxymethyl;
R⁴=in each case one line of Table A.

Table 397

Compounds of the formula I.1, where
R⁶=methyl;
R⁵=ethenyl;
R⁴=in each case one line of Table A.

Table 398

Compounds of the formula I.2, where
R⁶=methyl;
R⁵=ethenyl;
R⁴=in each case one line of Table A.

Table 399

Compounds of the formula I.3, where
R⁶=methyl;
R⁵=ethenyl;
R⁴=in each case one line of Table A.

Table 400

Compounds of the formula I.4, where
R⁶=methyl;
R⁵=ethenyl;
R⁴=in each case one line of Table A.

Table 401

Compounds of the formula I.1, where
R⁶=methyl;
R⁵=prop-2-en-1-yl;
R⁴=in each case one line of Table A.

Table 402

Compounds of the formula I.2, where
R⁶=methyl;
R⁵=prop-2-en-1-yl;
R⁴=in each case one line of Table A.

Table 403

Compounds of the formula I.3, where
R⁶=methyl;
R⁵=prop-2-en-1-yl;
R⁴=in each case one line of Table A.

Table 404

Compounds of the formula I.4, where
R⁶=methyl;
R⁵=prop-2-en-1-yl;
R⁴=in each case one line of Table A.

Table 405

Compounds of the formula I.1, where
R⁶=methyl;
R⁵=E-3-chloroprop-2-en-1-yl;
R⁴=in each case one line of Table A.

Table 406

Compounds of the formula I.2, where
R⁶=methyl;
R⁵=E-3-chloroprop-2-en-1-yl;
R⁴=in each case one line of Table A.

Table 407

Compounds of the formula I.3, where
R⁶=methyl;
R⁵=E-3-chloroprop-2-en-1-yl;
R⁴=in each case one line of Table A.

Table 408

Compounds of the formula I.4, where
R⁶=methyl;
R⁵=E-3-chloroprop-2-en-1-yl;
R⁴=in each case one line of Table A.

Table 409

Compounds of the formula I.1, where
R⁶=methyl;
R⁵=E-but-2-en-1-yl;
R⁴=in each case one line of Table A.

Table 410

Compounds of the formula I.2, where
R⁶=methyl;
R⁵=E-but-2-en-1-yl;
R⁴=in each case one line of Table A.

Table 411

Compounds of the formula I.3, where
R⁶=methyl;
R⁵=E-but-2-en-1-yl;
R⁴=in each case one line of Table A.

Table 412

Compounds of the formula I.4, where
R⁶=methyl;
R⁵=E-but-2-en-1-yl;
R⁴=in each case one line of Table A.

Table 413

Compounds of the formula I.1, where
R⁶=methyl;
R⁵=ethynyl;
R⁴=in each case one line of Table A.

Table 414

Compounds of the formula I.2, where
R⁶=methyl;

Table 415

Compounds of the formula I.3, where
$R^6$=methyl;
$R^5$=ethynyl;
$R^4$=in each case one line of Table A.

Table 416

Compounds of the formula I.4, where
$R^6$=methyl;
$R^5$=ethynyl;
$R^4$=in each case one line of Table A.

Table 417

Compounds of the formula I.1, where
$R^6$=methyl;
$R^5$=prop-2-yn-1-yl;
$R^4$=in each case one line of Table A.

Table 418

Compounds of the formula I.2, where
$R^6$=methyl;
$R^5$=prop-2-yn-1-yl;
$R^4$=in each case one line of Table A.

Table 419

Compounds of the formula I.3, where
$R^6$=methyl;
$R^5$=prop-2-yn-1-yl;
$R^4$=in each case one line of Table A.

Table 420

Compounds of the formula I.4, where
$R^6$=methyl;
$R^5$=prop-2-yn-1-yl;
$R^4$=in each case one line of Table A.

Table 421

Compounds of the formula I.1, where
$R^6$=methyl;
$R^5$=prop-1-yn-1-yl;
$R^4$=in each case one line of Table A.

Table 422

Compounds of the formula I.2, where
$R^6$=methyl;
$R^5$=prop-1-yn-1-yl;
$R^4$=in each case one line of Table A.

Table 423

Compounds of the formula I.3, where
$R^6$=methyl;
$R^5$=prop-1-yn-1-yl;
$R^4$=in each case one line of Table A.

Table 424

Compounds of the formula I.4, where
$R^6$=methyl;
$R^5$=prop-1-yn-1-yl;
$R^4$=in each case one line of Table A.

Table 425

Compounds of the formula I.1, where
$R^6$=methyl;
$R^5$=phenylethynyl;
$R^4$=in each case one line of Table A.

Table 426

Compounds of the formula I.2, where
$R^6$=methyl;
$R^5$=phenylethynyl;
$R^4$=in each case one line of Table A.

Table 427

Compounds of the formula I.3, where
$R^6$=methyl;
$R^5$=phenylethynyl;
$R^4$=in each case one line of Table A.

Table 428

Compounds of the formula I.4, where
$R^6$=methyl;
$R^5$=phenylethynyl;
$R^4$=in each case one line of Table A.

Table 429

Compounds of the formula I.1, where
$R^6$=methyl;
$R^5$=oxiran-2-yl;
$R^4$=in each case one line of Table A.

Table 430

Compounds of the formula I.2, where
$R^6$=methyl;
$R^5$=oxiran-2-yl;
$R^4$=in each case one line of Table A.

Table 431

Compounds of the formula I.3, where
$R^6$=methyl;
$R^5$=oxiran-2-yl;
$R^4$=in each case one line of Table A.

Table 432

Compounds of the formula I.4, where
$R^6$=methyl;
$R^5$=oxiran-2-yl;
$R^4$=in each case one line of Table A.

Table 433

Compounds of the formula I.1, where
$R^6$=methyl;
$R^5$=1,1-dichlorocyclopropyl;
$R^4$=in each case one line of Table A.

Table 434

Compounds of the formula I.2, where
$R^6$=methyl;

Table 435

Compounds of the formula I.3, where
$R^6$=methyl;
$R^5$=1,1-dichlorocyclopropyl;
$R^4$=in each case one line of Table A.

Table 436

Compounds of the formula I.4, where
$R^6$=methyl;
$R^5$=1,1-dichlorocyclopropyl;
$R^4$=in each case one line of Table A.

Table 437

Compounds of the formula I.1, where
$R^6$=methyl;
$R^5$=phenyl;
$R^4$=in each case one line of Table A.

Table 438

Compounds of the formula I.2, where
$R^6$=methyl;
$R^5$=phenyl;
$R^4$=in each case one line of Table A.

Table 439

Compounds of the formula I.3, where
$R^6$=methyl;
$R^5$=phenyl;
$R^4$=in each case one line of Table A.

Table 440

Compounds of the formula I.4, where
$R^6$=methyl;
$R^5$=phenyl;
$R^4$=in each case one line of Table A.

Table 441

Compounds of the formula I.1, where
$R^6$=methyl;
$R^5$=2-naphthyl;
$R^4$=in each case one line of Table A.

Table 442

Compounds of the formula I.2, where
$R^6$=methyl;
$R^5$=2-naphthyl;
$R^4$=in each case one line of Table A.

Table 443

Compounds of the formula I.3, where
$R^6$=methyl;
$R^5$=2-naphthyl;
$R^4$=in each case one line of Table A.

Table 444

Compounds of the formula I.4, where
$R^6$=methyl;
$R^5$=2-naphthyl;
$R^4$=in each case one line of Table A.

Table 445

Compounds of the formula I.1, where
$R^6$=methyl;
$R^5$=2-chlorophenyl;
$R^4$=in each case one line of Table A.

Table 446

Compounds of the formula I.2, where
$R^6$=methyl;
$R^5$=2-chlorophenyl;
$R^4$=in each case one line of Table A.

Table 447

Compounds of the formula I.3, where
$R^6$=methyl;
$R^5$=2-chlorophenyl;
$R^4$=in each case one line of Table A.

Table 448

Compounds of the formula I.4, where
$R^6$=methyl;
$R^5$=2-chlorophenyl;
$R^4$=in each case one line of Table A.

Table 449

Compounds of the formula I.1, where
$R^6$=methyl;
$R^5$=3-chlorophenyl;
$R^4$=in each case one line of Table A.

Table 450

Compounds of the formula I.2, where
$R^6$=methyl;
$R^5$=3-chlorophenyl;
$R^4$=in each case one line of Table A.

Table 451

Compounds of the formula I.3, where
$R^6$=methyl;
$R^5$=3-chlorophenyl;
$R^4$=in each case one line of Table A.

Table 452

Compounds of the formula I.4, where
$R^6$=methyl;
$R^5$=3-chlorophenyl;
$R^4$=in each case one line of Table A.

Table 453

Compounds of the formula I.1, where
$R^6$=methyl;
$R^5$=4-chlorophenyl;
$R^4$=in each case one line of Table A.

Table 454

Compounds of the formula I.2, where
$R^6$=methyl;

$R^5$=4-chlorophenyl;
$R^4$=in each case one line of Table A.

Table 455

Compounds of the formula I.3, where
$R^6$=methyl;
$R^5$=4-chlorophenyl;
$R^4$=in each case one line of Table A.

Table 456

Compounds of the formula I.4, where
$R^6$=methyl;
$R^5$=4-chlorophenyl;
$R^4$=in each case one line of Table A.

Table 457

Compounds of the formula I.1, where
$R^6$=methyl;
$R^5$=2-nitrophenyl;
$R^4$=in each case one line of Table A.

Table 458

Compounds of the formula I.2, where
$R^6$=methyl;
$R^5$=2-nitrophenyl;
$R^4$=in each case one line of Table A.

Table 459

Compounds of the formula I.3, where
$R^6$=methyl;
$R^5$=2-nitrophenyl;
$R^4$=in each case one line of Table A.

Table 460

Compounds of the formula I.4, where
$R^6$=methyl;
$R^5$=2-nitrophenyl;
$R^4$=in each case one line of Table A.

Table 461

Compounds of the formula I.1, where
$R^6$=methyl;
$R^5$=3-cyanophenyl;
$R^4$=in each case one line of Table A.

Table 462

Compounds of the formula I.2, where
$R^6$=methyl;
$R^5$=3-cyanophenyl;
$R^4$=in each case one line of Table A.

Table 463

Compounds of the formula I.3, where
$R^6$=methyl;
$R^5$=3-cyanophenyl;
$R^4$=in each case one line of Table A.

Table 464

Compounds of the formula I.4, where
$R^6$=methyl;
$R^5$=3-cyanophenyl;
$R^4$=in each case one line of Table A.

Table 465

Compounds of the formula I.1, where
$R^6$=methyl;
$R^5$=4-methylphenyl;
$R^4$=in each case one line of Table A.

Table 466

Compounds of the formula I.2, where
$R^6$=methyl;
$R^5$=4-methylphenyl;
$R^4$=in each case one line of Table A.

Table 467

Compounds of the formula I.3, where
$R^6$=methyl;
$R^5$=4-methylphenyl;
$R^4$=in each case one line of Table A.

Table 468

Compounds of the formula I.4, where
$R^6$=methyl;
$R^5$=4-methylphenyl;
$R^4$=in each case one line of Table A.

Table 469

Compounds of the formula I.1, where
$R^6$=methyl;
$R^5$=3-tert-butylphenyl;
$R^4$=in each case one line of Table A.

Table 470

Compounds of the formula I.2, where
$R^6$=methyl;
$R^5$=3-tert-butylphenyl;
$R^4$=in each case one line of Table A.

Table 471

Compounds of the formula I.3, where
$R^6$=methyl;
$R^5$=3-tert-butylphenyl;
$R^4$=in each case one line of Table A.

Table 472

Compounds of the formula I.4, where
$R^6$=methyl;
$R^5$=3-tert-butylphenyl;
$R^4$=in each case one line of Table A.

Table 473

Compounds of the formula I.1, where
$R^6$=methyl;
$R^5$=4-trifluoromethylphenyl;
$R^4$=in each case one line of Table A.

Table 474

Compounds of the formula I.2, where
$R^6$=methyl;

$R^5$=4-trifluoromethylphenyl;
$R^4$=in each case one line of Table A.

Table 475

Compounds of the formula I.3, where
$R^6$=methyl;
$R^5$=4-trifluoromethylphenyl;
$R^4$=in each case one line of Table A.

Table 476

Compounds of the formula I.4, where
$R^6$=methyl;
$R^5$=4-trifluoromethylphenyl;
$R^4$=in each case one line of Table A.

Table 477

Compounds of the formula I.1, where
$R^6$=methyl;
$R^5$=2-methoxyphenyl;
$R^4$=in each case one line of Table A.

Table 478

Compounds of the formula I.2, where
$R^6$=methyl;
$R^5$=2-methoxyphenyl;
$R^4$=in each case one line of Table A.

Table 479

Compounds of the formula I.3, where
$R^6$=methyl;
$R^5$=2-methoxyphenyl;
$R^4$=in each case one line of Table A.

Table 480

Compounds of the formula I.4, where
$R^6$=methyl;
$R^5$=2-methoxyphenyl;
$R^4$=in each case one line of Table A.

Table 481

Compounds of the formula I.1, where
$R^6$=methyl;
$R^5$=2,4-dichlorophenyl;
$R^4$=in each case one line of Table A.

Table 482

Compounds of the formula I.2, where
$R^6$=methyl;
$R^5$=2,4-dichlorophenyl;
$R^4$=in each case one line of Table A.

Table 483

Compounds of the formula I.3, where
$R^6$=methyl;
$R^5$=2,4-dichlorophenyl;
$R^4$=in each case one line of Table A.

Table 484

Compounds of the formula I.4, where
$R^6$=methyl;
$R^5$=2,4-dichlorophenyl;
$R^4$=in each case one line of Table A.

Table 485

Compounds of the formula I.1, where
$R^6$=methyl;
$R^5$=4-fluorophenyl;
$R^4$=in each case one line of Table A.

Table 486

Compounds of the formula I.2, where
$R^6$=methyl;
$R^5$=4-fluorophenyl;
$R^4$=in each case one line of Table A.

Table 487

Compounds of the formula I.3, where
$R^6$=methyl;
$R^5$=4-fluorophenyl;
$R^4$=in each case one line of Table A.

Table 488

Compounds of the formula I.4, where
$R^6$=methyl;
$R^5$=4-fluorophenyl;
$R^4$=in each case one line of Table A.

Table 489

Compounds of the formula I.1, where
$R^6$=methyl;
$R^5$=2-pyridyl;
$R^4$=in each case one line of Table A.

Table 490

Compounds of the formula I.2, where
$R^6$=methyl;
$R^5$=2-pyridyl;
$R^4$=in each case one line of Table A.

Table 491

Compounds of the formula I.3, where
$R^6$=methyl;
$R^5$=2-pyridyl;
$R^4$=in each case one line of Table A.

Table 492

Compounds of the formula I.4, where
$R^6$=methyl;
$R^5$=2-pyridyl;
$R^4$=in each case one line of Table A.

Table 493

Compounds of the formula I.1, where
$R^6$=methyl;
$R^5$=2-chloropyridin-6-yl;
$R^4$=in each case one line of Table A.

Table 494

Compounds of the formula I.2, where
$R^6$=methyl;

$R^5$=2-chloropyridin-6-yl;
$R^4$=in each case one line of Table A.

Table 495

Compounds of the formula I.3, where
$R^6$=methyl;
$R^5$=2-chloropyridin-6-yl;
$R^4$=in each case one line of Table A.

Table 496

Compounds of the formula I.4, where
$R^6$=methyl;
$R^5$=2-chloropyridin-6-yl;
$R^4$=in each case one line of Table A.

Table 497

Compounds of the formula I.1, where
$R^6$=methyl;
$R^5$=5-methylpyrimidin-2-yl;
$R^4$=in each case one line of Table A.

Table 498

Compounds of the formula I.2, where
$R^6$=methyl;
$R^5$=5-methylpyrimidin-2-yl;
$R^4$=in each case one line of Table A.

Table 499

Compounds of the formula I.3, where
$R^6$=methyl;
$R^5$=5-methylpyrimidin-2-yl;
$R^4$=in each case one line of Table A.

Table 500

Compounds of the formula I.4, where
$R^6$=methyl;
$R^5$=5-methylpyrimidin-2-yl;
$R^4$=in each case one line of Table A.

Table 501

Compounds of the formula I.1, where
$R^6$=methyl;
$R^5$=2-chloropyridin-5-yl;
$R^4$=in each case one line of Table A.

Table 502

Compounds of the formula I.2, where
$R^6$=methyl;
$R^5$=2-chloropyridin-5-yl;
$R^4$=in each case one line of Table A.

Table 503

Compounds of the formula I.3, where
$R^6$=methyl;
$R^5$=2-chloropyridin-5-yl;
$R^4$=in each case one line of Table A.

Table 504

Compounds of the formula I.4, where
$R^6$=methyl;
$R^5$=2-chloropyridin-5-yl;
$R^4$=in each case one line of Table A.

Table 505

Compounds of the formula I.1, where
$R^6$=methyl;
$R^5$=5-cyanothien-2-yl;
$R^4$=in each case one line of Table A.

Table 506

Compounds of the formula I.2, where
$R^6$=methyl;
$R^5$=5-cyanothien-2-yl;
$R^4$=in each case one line of Table A.

Table 507

Compounds of the formula I.3, where
$R^6$=methyl;
$R^5$=5-cyanothien-2-yl;
$R^4$=in each case one line of Table A.

Table 508

Compounds of the formula I.4, where
$R^6$=methyl;
$R^5$=5-cyanothien-2-yl;
$R^4$=in each case one line of Table A.

Table 509

Compounds of the formula I.1, where
$R^6$=methyl;
$R^5$=4-chlorooxazol-2-yl;
$R^4$=in each case one line of Table A.

Table 510

Compounds of the formula I.2, where
$R^6$=methyl;
$R^5$=4-chlorooxazol-2-yl;
$R^4$=in each case one line of Table A.

Table 511

Compounds of the formula I.3, where
$R^6$=methyl;
$R^5$=4-chlorooxazol-2-yl;
$R^4$=in each case one line of Table A.

Table 512

Compounds of the formula I.4, where
$R^6$=methyl;
$R^5$=4-chlorooxazol-2-yl;
$R^4$=in each case one line of Table A.

Table 513

Compounds of the formula I.1, where
$R^6$=methyl;
$R^5$=1-methoxypyrazol-3-yl;
$R^4$=in each case one line of Table A.

Table 514

Compounds of the formula I.2, where
$R^6$=methyl;

$R^5$=1-methoxypyrazol-3-yl;
$R^4$=in each case one line of Table A.

Table 515

Compounds of the formula I.3, where
$R^6$=methyl;
$R^5$=1-methoxypyrazol-3-yl;
$R^4$=in each case one line of Table A.

Table 516

Compounds of the formula I.4, where
$R^6$=methyl;
$R^5$=1-methoxypyrazol-3-yl;
$R^4$=in each case one line of Table A.

Table 517

Compounds of the formula I.1, where
$R^6$=methyl;
$R^5$=5-trifluoromethyl-1,2,4-oxadiazol-3-yl;
$R^4$=in each case one line of Table A.

Table 518

Compounds of the formula I.2, where
$R^6$=methyl;
$R^5$=5-trifluoromethyl-1,2,4-oxadiazol-3-yl;
$R^4$=in each case one line of Table A.

Table 519

Compounds of the formula I.3, where
$R^6$=methyl;
$R^5$=5-trifluoromethyl-1,2,4-oxadiazol-3-yl;
$R^4$=in each case one line of Table A.

Table 520

Compounds of the formula I.4, where
$R^6$=methyl;
$R^5$=5-trifluoromethyl-1,2,4-oxadiazol-3-yl;
$R^4$=in each case one line of Table A.

Table 521

Compounds of the formula I.1, where
$R^6$=ethyl;
$R^5$=ethyl;
$R^4$=in each case one line of Table A.

Table 522

Compounds of the formula I.2, where
$R^6$=ethyl;
$R^5$=ethyl;
$R^4$=in each case one line of Table A.

Table 523

Compounds of the formula I.3, where
$R^6$=ethyl;
$R^5$=ethyl;
$R^4$=in each case one line of Table A.

Table 524

Compounds of the formula I.4, where
$R^6$=ethyl;
$R^5$=ethyl;
$R^4$=in each case one line of Table A.

Table 525

Compounds of the formula I.1, where
$R^6$=ethyl;
$R^5$=n-propyl;
$R^4$=in each case one line of Table A.

Table 526

Compounds of the formula I.2, where
$R^6$=ethyl;
$R^5$=n-propyl;
$R^4$=in each case one line of Table A.

Table 527

Compounds of the formula I.3, where
$R^6$=ethyl;
$R^5$=n-propyl;
$R^4$=in each case one line of Table A.

Table 528

Compounds of the formula I.4, where
$R^6$=ethyl;
$R^5$=n-propyl;
$R^4$=in each case one line of Table A.

Table 529

Compounds of the formula I.1, where
$R^6$=ethyl;
$R^5$=isopropyl;
$R^4$=in each case one line of Table A.

Table 530

Compounds of the formula I.2, where
$R^6$=ethyl;
$R^5$=isopropyl;
$R^4$=in each case one line of Table A.

Table 531

Compounds of the formula I.3, where
$R^6$=ethyl;
$R^5$=isopropyl;
$R^4$=in each case one line of Table A.

Table 532

Compounds of the formula I.4, where
$R^6$=ethyl;
$R^5$=isopropyl;
$R^4$=in each case one line of Table A.

Table 533

Compounds of the formula I.1, where
$R^6$=ethyl;
$R^5$=cyclopropyl;
$R^4$=in each case one line of Table A.

Table 534

Compounds of the formula I.2, where
$R^6$=ethyl;

$R^5$=cyclopropyl;
$R^4$=in each case one line of Table A.

Table 535

Compounds of the formula I.3, where
$R^6$=ethyl;
$R^5$=cyclopropyl;
$R^4$=in each case one line of Table A.

Table 536

Compounds of the formula I.4, where
$R^6$=ethyl;
$R^5$=cyclopropyl;
$R^4$=in each case one line of Table A.

Table 537

Compounds of the formula I.1, where
$R^6$=ethyl;
$R^5$=tert-butyl;
$R^4$=in each case one line of Table A.

Table 538

Compounds of the formula I.2, where
$R^6$=ethyl;
$R^5$=tert-butyl;
$R^4$=in each case one line of Table A.

Table 539

Compounds of the formula I.3, where
$R^6$=ethyl;
$R^5$=tert-butyl;
$R^4$=in each case one line of Table A.

Table 540

Compounds of the formula I.4, where
$R^6$=ethyl;
$R^5$=tert-butyl;
$R^4$=in each case one line of Table A.

Table 541

Compounds of the formula I.1, where
$R^6$=ethyl;
$R^5$=trifluoromethyl;
$R^4$=in each case one line of Table A.

Table 542

Compounds of the formula I.2, where
$R^6$=ethyl;
$R^5$=trifluoromethyl;
$R^4$=in each case one line of Table A.

Table 543

Compounds of the formula I.3, where
$R^6$=ethyl;
$R^5$=trifluoromethyl;
$R^4$=in each case one line of Table A.

Table 544

Compounds of the formula I.4, where
$R^6$=ethyl;
$R^5$=trifluoromethyl;
$R^4$=in each case one line of Table A.

Table 545

Compounds of the formula I.1, where
$R^6$=ethyl;
$R^5$=phenoxymethyl;
$R^4$=in each case one line of Table A.

Table 546

Compounds of the formula I.2, where
$R^6$=ethyl;
$R^5$=phenoxymethyl;
$R^4$=in each case one line of Table A.

Table 547

Compounds of the formula I.3, where
$R^6$=ethyl;
$R^5$=phenoxymethyl;
$R^4$=in each case one line of Table A.

Table 548

Compounds of the formula I.4, where
$R^6$=ethyl;
$R^5$=phenoxymethyl;
$R^4$=in each case one line of Table A.

Table 549

Compounds of the formula I.1, where
$R^6$=ethyl;
$R^5$=2-pyridyloxymethyl;
$R^4$=in each case one line of Table A.

Table 550

Compounds of the formula I.2, where
$R^6$=ethyl;
$R^5$=2-pyridyloxymethyl;
$R^4$=in each case one line of Table A.

Table 551

Compounds of the formula I.3, where
$R^6$=ethyl;
$R^5$=2-pyridyloxymethyl;
$R^4$=in each case one line of Table A.

Table 552

Compounds of the formula I.4, where
$R^6$=ethyl;
$R^5$=2-pyridyloxymethyl;
$R^4$=in each case one line of Table A.

Table 553

Compounds of the formula I.1, where
$R^6$=ethyl;
$R^5$=5-methylpyrazol-3-yloxymethyl;
$R^4$=in each case one line of Table A.

Table 554

Compounds of the formula I.2, where
$R^6$=ethyl;
$R^5$=5-methylpyrazol-3-yloxymethyl;
$R^4$=in each case one line of Table A.

Table 555

Compounds of the formula I.3, where
$R^6$=ethyl;

$R^5$=5-methylpyrazol-3-yloxymethyl;
$R^4$=in each case one line of Table A.

Table 556
Compounds of the formula I.4, where
$R^6$=ethyl;
$R^5$=5-methylpyrazol-3-yloxymethyl;
$R^4$=in each case one line of Table A.

Table 557
Compounds of the formula I.1, where
$R^6$=ethyl;
$R^5$=ethenyl;
$R^4$=in each case one line of Table A.

Table 558
Compounds of the formula I.2, where
$R^6$=ethyl;
$R^5$=ethenyl;
$R^4$=in each case one line of Table A.

Table 559
Compounds of the formula I.3, where
$R^6$=ethyl;
$R^5$=ethenyl;
$R^4$=in each case one line of Table A.

Table 560
Compounds of the formula I.4, where
$R^6$=ethyl;
$R^5$=ethenyl;
$R^4$=in each case one line of Table A.

Table 561
Compounds of the formula I.1, where
$R^6$=ethyl;
$R^5$=ethynyl;
$R^4$=in each case one line of Table A.

Table 562
Compounds of the formula I.2, where
$R^6$=ethyl;
$R^5$=ethynyl;
$R^4$=in each case one line of Table A.

Table 563
Compounds of the formula I.3, where
$R^6$=ethyl;
$R^5$=ethynyl;
$R^4$=in each case one line of Table A.

Table 564
Compounds of the formula I.4, where
$R^6$=ethyl;
$R^5$=ethynyl;
$R^4$=in each case one line of Table A.

Table 565
Compounds of the formula I.1, where
$R^6$=ethyl;
$R^5$=phenyl;
$R^4$=in each case one line of Table A.

Table 566
Compounds of the formula I.2, where
$R^6$=ethyl;
$R^5$=phenyl;
$R^4$=in each case one line of Table A.

Table 567
Compounds of the formula I.3, where
$R^6$=ethyl;
$R^5$=phenyl;
$R^4$=in each case one line of Table A.

Table 568
Compounds of the formula I.4, where
$R^6$=ethyl;
$R^5$=phenyl;
$R^4$=in each case one line of Table A.

Table 569
Compounds of the formula I.1, where
$R^6$=ethyl;
$R^5$=4-chlorophenyl;
$R^4$=in each case one line of Table A.

Table 570
Compounds of the formula I.2, where
$R^6$=ethyl;
$R^5$=4-chlorophenyl;
$R^4$=in each case one line of Table A.

Table 571
Compounds of the formula I.3, where
$R^6$=ethyl;
$R^5$=4-chlorophenyl;
$R^4$=in each case one line of Table A.

Table 572
Compounds of the formula I.4, where
$R^6$=ethyl;
$R^5$=4-chlorophenyl;
$R^4$=in each case one line of Table A.

Table 573
Compounds of the formula I.1, where
$R^6$=ethyl;
$R^5$=4-fluorophenyl;
$R^4$=in each case one line of Table A.

Table 574
Compounds of the formula I.2, where
$R^6$=ethyl;
$R^5$=4-fluorophenyl;
$R^4$=in each case one line of Table A.

Table 575
Compounds of the formula I.3, where
$R^6$=ethyl;
$R^5$=4-fluorophenyl;
$R^4$=in each case one line of Table A.

Table 576
Compounds of the formula I.4, where
$R^6$=ethyl;
$R^5$=4-fluorophenyl;
$R^4$=in each case one line of Table A.

Table 577
Compounds of the formula I.1, where
$R^6$=ethyl;
$R^5$=2-chloropyrid-6-yl;
$R^4$=in each case one line of Table A.

Table 578
Compounds of the formula I.2, where
$R^6$=ethyl;
$R^5$=2-chloropyrid-6-yl;
$R^4$=in each case one line of Table A.

Table 579
Compounds of the formula I.3, where
$R^6$=ethyl;

$R^5$=2-chloropyrid-6-yl;
$R^4$=in each case one line of Table A.

Table 580
Compounds of the formula I.4, where
$R^6$=ethyl;
$R^5$=2-chloropyrid-6-yl;
$R^4$=in each case one line of Table A.

Table 581
Compounds of the formula I.1, where
$R^6$=isopropyl;
$R^5$=n-propyl;
$R^4$=in each case one line of Table A.

Table 582
Compounds of the formula I.2, where
$R^6$=isopropyl;
$R^5$=n-propyl;
$R^4$=in each case one line of Table A.

Table 583
Compounds of the formula I.3, where
$R^6$=isopropyl;
$R^5$=n-propyl;
$R^4$=in each case one line of Table A.

Table 584
Compounds of the formula I.4, where
$R^6$=isopropyl;
$R^5$=n-propyl;
$R^4$=in each case one line of Table A.

Table 585
Compounds of the formula I.1, where
$R^6$=isopropyl;
$R^5$=isopropyl;
$R^4$=in each case one line of Table A.

Table 586
Compounds of the formula I.2, where
$R^6$=isopropyl;
$R^5$=isopropyl;
$R^4$=in each case one line of Table A.

Table 587
Compounds of the formula I.3, where
$R^6$=isopropyl;
$R^5$=isopropyl;
$R^4$=in each case one line of Table A.

Table 588
Compounds of the formula I.4, where
$R^6$=isopropyl;
$R^5$=isopropyl;
$R^4$=in each case one line of Table A.

Table 589
Compounds of the formula I.1, where
$R^6$=isopropyl;
$R^5$=trifluoromethyl;
$R^4$=in each case one line of Table A.

Table 590
Compounds of the formula I.2, where
$R^6$=isopropyl;
$R^5$=trifluoromethyl;
$R^4$=in each case one line of Table A.

Table 591
Compounds of the formula I.3, where
$R^6$=isopropyl;
$R^5$=trifluoromethyl;
$R^4$=in each case one line of Table A.

Table 592
Compounds of the formula I.4, where
$R^6$=isopropyl;
$R^5$=trifluoromethyl;
$R^4$=in each case one line of Table A.

Table 593
Compounds of the formula I.1, where
$R^6$=isopropyl;
$R^5$=phenoxymethyl;
$R^4$=in each case one line of Table A.

Table 594
Compounds of the formula I.2, where
$R^6$=isopropyl;
$R^5$=phenoxymethyl;
$R^4$=in each case one line of Table A.

Table 595
Compounds of the formula I.3, where
$R^6$=isopropyl;
$R^5$=phenoxymethyl;
$R^4$=in each case one line of Table A.

Table 596
Compounds of the formula I.4, where
$R^6$=isopropyl;
$R^5$=phenoxymethyl;
$R^4$=in each case one line of Table A.

Table 597
Compounds of the formula I.1, where
$R^6$=isopropyl;
$R^5$=4-fluorophenoxymethyl;
$R^4$=in each case one line of Table A.

Table 598
Compounds of the formula I.2, where
$R^6$=isopropyl;
$R^5$=4-fluorophenoxymethyl;
$R^4$=in each case one line of Table A.

Table 599
Compounds of the formula I.3, where
$R^6$=isopropyl;
$R^5$=4-fluorophenoxymethyl;
$R^4$=in each case one line of Table A.

Table 600
Compounds of the formula I.4, where
$R^6$=isopropyl;
$R^5$=4-fluorophenoxymethyl;
$R^4$=in each case one line of Table A.

Table 601
Compounds of the formula I.1, where
$R^6$=isopropyl;
$R^5$=2-pyridyloxymethyl;
$R^4$=in each case one line of Table A.

Table 602
Compounds of the formula I.2, where
$R^6$=isopropyl;
$R^5$=2-pyridyloxymethyl;
$R^4$=in each case one line of Table A.

Table 603
Compounds of the formula I.3, where
$R^6$=isopropyl;

Table 604
Compounds of the formula I.4, where
R$^6$=isopropyl;
R$^5$=2-pyridyloxymethyl;
R$^4$=in each case one line of Table A.

Table 605
Compounds of the formula I.1, where
R$^6$=isopropyl;
R$^5$=ethenyl;
R$^4$=in each case one line of Table A.

Table 606
Compounds of the formula I.2, where
R$^6$=isopropyl;
R$^5$=ethenyl;
R$^4$=in each case one line of Table A.

Table 607
Compounds of the formula I.3, where
R$^6$=isopropyl;
R$^5$=ethenyl;
R$^4$=in each case one line of Table A.

Table 608
Compounds of the formula I.4, where
R$^6$=isopropyl;
R$^5$=ethenyl;
R$^4$=in each case one line of Table A.

Table 609
Compounds of the formula I.1, where
R$^6$=isopropyl;
R$^5$=prop-1-yn-1-yl;
R$^4$=in each case one line of Table A.

Table 610
Compounds of the formula I.2, where
R$^6$=isopropyl;
R$^5$=prop-1-yn-1-yl;
R$^4$=in each case one line of Table A.

Table 611
Compounds of the formula I.3, where
R$^6$=isopropyl;
R$^5$=prop-1-yn-1-yl;
R$^4$=in each case one line of Table A.

Table 612
Compounds of the formula I.4, where
R$^6$=isopropyl;
R$^5$=prop-1-yn-1-yl;
R$^4$=in each case one line of Table A.

Table 613
Compounds of the formula I.1, where
R$^6$=isopropyl;
R$^5$=phenyl;
R$^4$=in each case one line of Table A.

Table 614
Compounds of the formula I.2, where
R$^6$=isopropyl;
R$^5$=phenyl;
R$^4$=in each case one line of Table A.

Table 615
Compounds of the formula I.3, where
R$^6$=isopropyl;
R$^5$=phenyl;
R$^4$=in each case one line of Table A.

Table 616
Compounds of the formula I.4, where
R$^6$=isopropyl;
R$^5$=phenyl;
R$^4$=in each case one line of Table A.

Table 617
Compounds of the formula I.1, where
R$^6$=isopropyl;
R$^5$=3-cyanophenyl;
R$^4$=in each case one line of Table A.

Table 618
Compounds of the formula I.2, where
R$^6$=isopropyl;
R$^5$=3-cyanophenyl;
R$^4$=in each case one line of Table A.

Table 619
Compounds of the formula I.3, where
R$^6$=isopropyl;
R$^5$=3-cyanophenyl;
R$^4$=in each case one line of Table A.

Table 620
Compounds of the formula I.4, where
R$^6$=isopropyl;
R$^5$=3-cyanophenyl;
R$^4$=in each case one line of Table A.

Table 621
Compounds of the formula I.1, where
R$^6$=isopropyl;
R$^5$=2-chloropyrid-6-yl;
R$^4$=in each case one line of Table A.

Table 622
Compounds of the formula I.2, where
R$^6$=isopropyl;
R$^5$=2-chloropyrid-6-yl;
R$^4$=in each case one line of Table A.

Table 623
Compounds of the formula I.3, where
R$^6$=isopropyl;
R$^5$=2-chloropyrid-6-yl;
R$^4$=in each case one line of Table A.

Table 624
Compounds of the formula I.4, where
R$^6$=isopropyl;
R$^5$=2-chloropyrid-6-yl;
R$^4$=in each case one line of Table A.

Table 625
Compounds of the formula I.1, where
R$^6$=cyclopropyl;
R$^5$=cyclopropyl;
R$^4$=in each case one line of Table A.

Table 626
Compounds of the formula I.2, where
R$^6$=cyclopropyl;
R$^5$=cyclopropyl;
R$^4$=in each case one line of Table A.

Table 627
Compounds of the formula I.3, where
R$^6$=cyclopropyl;

$R^5$=cyclopropyl;
$R^4$=in each case one line of Table A.

Table 628
Compounds of the formula I.4, where
$R^6$=cyclopropyl;
$R^5$=cyclopropyl;
$R^4$=in each case one line of Table A.

Table 629
Compounds of the formula I.1, where
$R^6$=cyclopropyl;
$R^5$=trifluoromethyl;
$R^4$=in each case one line of Table A.

Table 630
Compounds of the formula I.2, where
$R^6$=cyclopropyl;
$R^5$=trifluoromethyl;
$R^4$=in each case one line of Table A.

Table 631
Compounds of the formula I.3, where
$R^6$=cyclopropyl;
$R^5$=trifluoromethyl;
$R^4$=in each case one line of Table A.

Table 632
Compounds of the formula I.4, where
$R^6$=cyclopropyl;
$R^5$=trifluoromethyl;
$R^4$=in each case one line of Table A.

Table 633
Compounds of the formula I.1, where
$R^6$=cyclopropyl;
$R^5$=phenoxymethyl;
$R^4$=in each case one line of Table A.

Table 634
Compounds of the formula I.2, where
$R^6$=cyclopropyl;
$R^5$=phenoxymethyl;
$R^4$=in each case one line of Table A.

Table 635
Compounds of the formula I.3, where
$R^6$=cyclopropyl;
$R^5$=phenoxymethyl;
$R^4$=in each case one line of Table A.

Table 636
Compounds of the formula I.4, where
$R^6$=cyclopropyl;
$R^5$=phenoxymethyl;
$R^4$=in each case one line of Table A.

Table 637
Compounds of the formula I.1, where
$R^6$=cyclopropyl;
$R^5$=2-pyridinyloxymethyl;
$R^4$=in each case one line of Table A.

Table 638
Compounds of the formula I.2, where
$R^6$=cyclopropyl;
$R^5$=2-pyridinyloxymethyl;
$R^4$=in each case one line of Table A.

Table 639
Compounds of the formula I.3, where
$R^6$=cyclopropyl;
$R^5$=2-pyridinyloxymethyl;
$R^4$=in each case one line of Table A.

Table 640
Compounds of the formula I.4, where
$R^6$=cyclopropyl;
$R^5$=2-pyridinyloxymethyl;
$R^4$=in each case one line of Table A.

Table 641
Compounds of the formula I.1, where
$R^6$=cyclopropyl;
$R^5$=ethenyl;
$R^4$=in each case one line of Table A.

Table 642
Compounds of the formula I.2, where
$R^6$=cyclopropyl;
$R^5$=ethenyl;
$R^4$=in each case one line of Table A.

Table 643
Compounds of the formula I.3, where
$R^6$=cyclopropyl;
$R^5$=ethenyl;
$R^4$=in each case one line of Table A.

Table 644
Compounds of the formula I.4, where
$R^6$=cyclopropyl;
$R^5$=ethenyl;
$R^4$=in each case one line of Table A.

Table 645
Compounds of the formula I.1, where
$R^6$=cyclopropyl;
$R^5$=ethynyl;
$R^4$=in each case one line of Table A.

Table 646
Compounds of the formula I.2, where
$R^6$=cyclopropyl;
$R^5$=ethynyl;
$R^4$=in each case one line of Table A.

Table 647
Compounds of the formula I.3, where
$R^6$=cyclopropyl;
$R^5$=ethynyl;
$R^4$=in each case one line of Table A.

Table 648
Compounds of the formula I.4, where
$R^6$=cyclopropyl;
$R^5$=ethynyl;
$R^4$=in each case one line of Table A.

Table 649
Compounds of the formula I.1, where
$R^6$=cyclopropyl;
$R^5$=phenyl;
$R^4$=in each case one line of Table A.

Table 650
Compounds of the formula I.2, where
$R^6$=cyclopropyl;
$R^5$=phenyl;
$R^4$=in each case one line of Table A.

Table 651
Compounds of the formula I.3, where
$R^6$=cyclopropyl;

$R^5$=phenyl;
$R^4$=in each case one line of Table A.

Table 652
Compounds of the formula I.4, where
$R^6$=cyclopropyl;
$R^5$=phenyl;
$R^4$=in each case one line of Table A.

Table 653
Compounds of the formula I.1, where
$R^6$=cyclopropyl;
$R^5$=4-chlorophenyl;
$R^4$=in each case one line of Table A.

Table 654
Compounds of the formula I.2, where
$R^6$=cyclopropyl;
$R^5$=4-chlorophenyl;
$R^4$=in each case one line of Table A.

Table 655
Compounds of the formula I.3, where
$R^6$=cyclopropyl;
$R^5$=4-chlorophenyl;
$R^4$=in each case one line of Table A.

Table 656
Compounds of the formula I.4, where
$R^6$=cyclopropyl;
$R^5$=4-chlorophenyl;
$R^4$=in each case one line of Table A.

Table 657
Compounds of the formula I.1, where
$R^6$=cyclopropyl;
$R^5$=4-fluorophenyl;
$R^4$=in each case one line of Table A.

Table 658
Compounds of the formula I.2, where
$R^6$=cyclopropyl;
$R^5$=4-fluorophenyl;
$R^4$=in each case one line of Table A.

Table 659
Compounds of the formula I.3, where
$R^6$=cyclopropyl;
$R^5$=4-fluorophenyl;
$R^4$=in each case one line of Table A.

Table 660
Compounds of the formula I.4, where
$R^6$=cyclopropyl;
$R^5$=4-fluorophenyl;
$R^4$=in each case one line of Table A.

Table 661
Compounds of the formula I.1, where
$R^6$=cyclopropyl;
$R^5$=2-methylpyrid-6-yl;
$R^4$=in each case one line of Table A.

Table 662
Compounds of the formula I.2, where
$R^6$=cyclopropyl;
$R^5$=2-methylpyrid-6-yl;
$R^4$=in each case one line of Table A.

Table 663
Compounds of the formula I.3, where
$R^6$=cyclopropyl;

$R^5$=2-methylpyrid-6-yl;
$R^4$=in each case one line of Table A.

Table 664
Compounds of the formula I.4, where
$R^6$=cyclopropyl;
$R^5$=2-methylpyrid-6-yl;
$R^4$=in each case one line of Table A.

Table 665
Compounds of the formula I.1, where
$R^6$=trifluoromethyl;
$R^5$=n-propyl;
$R^4$=in each case one line of Table A.

Table 666
Compounds of the formula I.2, where
$R^6$=trifluoromethyl;
$R^5$=n-propyl;
$R^4$=in each case one line of Table A.

Table 667
Compounds of the formula I.3, where
$R^6$=trifluoromethyl;
$R^5$=n-propyl;
$R^4$=in each case one line of Table A.

Table 668
Compounds of the formula I.4, where
$R^6$=trifluoromethyl;
$R^5$=n-propyl;
$R^4$=in each case one line of Table A.

Table 669
Compounds of the formula I.1, where
$R^6$=trifluoromethyl;
$R^5$=tert-butyl;
$R^4$=in each case one line of Table A.

Table 670
Compounds of the formula I.2, where
$R^6$=trifluoromethyl;
$R^5$=tert-butyl;
$R^4$=in each case one line of Table A.

Table 671
Compounds of the formula I.3, where
$R^6$=trifluoromethyl;
$R^5$=tert-butyl;
$R^4$=in each case one line of Table A.

Table 672
Compounds of the formula I.4, where
$R^6$=trifluoromethyl;
$R^5$=tert-butyl;
$R^4$=in each case one line of Table A.

Table 673
Compounds of the formula I.1, where
$R^6$=trifluoromethyl;
$R^5$=trifluoromethyl;
$R^4$=in each case one line of Table A.

Table 674
Compounds of the formula I.2, where
$R^6$=trifluoromethyl;
$R^5$=trifluoromethyl;
$R^4$=in each case one line of Table A.

Table 675
Compounds of the formula I.3, where
$R^6$=trifluoromethyl;

$R^5$=trifluoromethyl;
$R^4$=in each case one line of Table A.

Table 676
Compounds of the formula I.4, where
$R^6$=trifluoromethyl;
$R^5$=trifluoromethyl;
$R^4$=in each case one line of Table A.

Table 677
Compounds of the formula I.1, where
$R^6$=trifluoromethyl;
$R^5$=phenoxymethyl;
$R^4$=in each case one line of Table A.

Table 678
Compounds of the formula I.2, where
$R^6$=trifluoromethyl;
$R^5$=phenoxymethyl;
$R^4$=in each case one line of Table A.

Table 679
Compounds of the formula I.3, where
$R^6$=trifluoromethyl;
$R^5$=phenoxymethyl;
$R^4$=in each case one line of Table A.

Table 680
Compounds of the formula I.4, where
$R^6$=trifluoromethyl;
$R^5$=phenoxymethyl;
$R^4$=in each case one line of Table A.

Table 681
Compounds of the formula I.1, where
$R^6$=trifluoromethyl;
$R^5$=phenyl;
$R^4$=in each case one line of Table A.

Table 682
Compounds of the formula I.2, where
$R^6$=trifluoromethyl;
$R^5$=phenyl;
$R^4$=in each case one line of Table A.

Table 683
Compounds of the formula I.3, where
$R^6$=trifluoromethyl;
$R^5$=phenyl;
$R^4$=in each case one line of Table A.

Table 684
Compounds of the formula I.4, where
$R^6$=trifluoromethyl;
$R^5$=phenyl;
$R^4$=in each case one line of Table A.

Table 685
Compounds of the formula I.1, where
$R^6$=trifluoromethyl;
$R^5$=4-fluorophenyl;
$R^4$=in each case one line of Table A.

Table 686
Compounds of the formula I.2, where
$R^6$=trifluoromethyl;
$R^5$=4-fluorophenyl;
$R^4$=in each case one line of Table A.

Table 687
Compounds of the formula I.3, where
$R^6$=trifluoromethyl;
$R^5$=4-fluorophenyl;
$R^4$=in each case one line of Table A.

Table 688
Compounds of the formula I.4, where
$R^6$=trifluoromethyl;
$R^5$=4-fluorophenyl;
$R^4$=in each case one line of Table A.

Table 689
Compounds of the formula I.1, where
$R^6$=trifluoromethyl;
$R^5$=4-chlorophenyl;
$R^4$=in each case one line of Table A.

Table 690
Compounds of the formula I.2, where
$R^6$=trifluoromethyl;
$R^5$=4-chlorophenyl;
$R^4$=in each case one line of Table A.

Table 691
Compounds of the formula I.3, where
$R^6$=trifluoromethyl;
$R^5$=4-chlorophenyl;
$R^4$=in each case one line of Table A.

Table 692
Compounds of the formula I.4, where
$R^6$=trifluoromethyl;
$R^5$=4-chlorophenyl;
$R^4$=in each case one line of Table A.

Table 693
Compounds of the formula I.1, where
$R^6$=trifluoromethyl;
$R^5$=3-methoxyphenyl;
$R^4$=in each case one line of Table A.

Table 694
Compounds of the formula I.2, where
$R^6$=trifluoromethyl;
$R^5$=3-methoxyphenyl;
$R^4$=in each case one line of Table A.

Table 695
Compounds of the formula I.3, where
$R^6$=trifluoromethyl;
$R^5$=3-methoxyphenyl;
$R^4$=in each case one line of Table A.

Table 696
Compounds of the formula I.4, where
$R^6$=trifluoromethyl;
$R^5$=3-methoxyphenyl;
$R^4$=in each case one line of Table A.

Table 697
Compounds of the formula I.1, where
$R^6$=trifluoromethyl;
$R^5$=2-chloropyrid-6-yl;
$R^4$=in each case one line of Table A.

Table 698
Compounds of the formula I.2, where
$R^6$=trifluoromethyl;
$R^5$=2-chloropyrid-6-yl;
$R^4$=in each case one line of Table A.

Table 699
Compounds of the formula I.3, where
$R^6$=trifluoromethyl;

$R^5$=2-chloropyrid-6-yl;
$R^4$=in each case one line of Table A.

Table 700
Compounds of the formula I.4, where
$R^6$=trifluoromethyl;
$R^5$=2-chloropyrid-6-yl;
$R^4$=in each case one line of Table A.

Table 701
Compounds of the formula I.1, where
$R^6$=phenyl;
$R^5$=phenyl;
$R^4$=in each case one line of Table A.

Table 702
Compounds of the formula I.2, where
$R^6$=phenyl;
$R^5$=phenyl;
$R^4$=in each case one line of Table A.

Table 703
Compounds of the formula I.3, where
$R^6$=phenyl;
$R^5$=phenyl;
$R^4$=in each case one line of Table A.

Table 704
Compounds of the formula I.4, where
$R^6$=phenyl;
$R^5$=phenyl;
$R^4$=in each case one line of Table A.

Table 705
Compounds of the formula I.1, where
$R^6$=phenyl;
$R^5$=4-fluorophenyl;
$R^4$=in each case one line of Table A.

Table 706
Compounds of the formula I.2, where
$R^6$=phenyl;
$R^5$=4-fluorophenyl;
$R^4$=in each case one line of Table A.

Table 707
Compounds of the formula I.3, where
$R^6$=phenyl;
$R^5$=4-fluorophenyl;
$R^4$=in each case one line of Table A.

Table 708
Compounds of the formula I.4, where
$R^6$=phenyl;
$R^5$=4-fluorophenyl;
$R^4$=in each case one line of Table A.

Table 709
Compounds of the formula I.1, where
$R^6$=methoxymethyl;
$R^5$=phenyl;
$R^4$=in each case one line of Table A.

Table 710
Compounds of the formula I.2, where
$R^6$=methoxymethyl;
$R^5$=phenyl;
$R^4$=in each case one line of Table A.

Table 711
Compounds of the formula I.3, where
$R^6$=methoxymethyl;
$R^5$=phenyl;
$R^4$=in each case one line of Table A.

Table 712
Compounds of the formula I.4, where
$R^6$=methoxymethyl;
$R^5$=phenyl;
$R^4$=in each case one line of Table A.

Table 713
Compounds of the formula I.1, where
$R^6$=methoxymethyl;
$R^5$=4-chlorophenyl;
$R^4$=in each case one line of Table A.

Table 714
Compounds of the formula I.2, where
$R^6$=methoxymethyl;
$R^5$=4-chlorophenyl;
$R^4$=in each case one line of Table A.

Table 715
Compounds of the formula I.3, where
$R^6$=methoxymethyl;
$R^5$=4-chlorophenyl;
$R^4$=in each case one line of Table A.

Table 716
Compounds of the formula I.4, where
$R^6$=methoxymethyl;
$R^5$=4-chlorophenyl;
$R^4$=in each case one line of Table A.

Table 717
Compounds of the formula I.1, where
$R^6$=2-pyrimidinyl;
$R^5$=phenyl;
$R^4$=in each case one line of Table A.

Table 718
Compounds of the formula I.2, where
$R^6$=2-pyrimidinyl;
$R^5$=phenyl;
$R^4$=in each case one line of Table A.

Table 719
Compounds of the formula I.3, where
$R^6$=2-pyrimidinyl;
$R^5$=phenyl;
$R^4$=in each case one line of Table A.

Table 720
Compounds of the formula I.4, where
$R^6$=2-pyrimidinyl;
$R^5$=phenyl;
$R^4$=in each case one line of Table A.

Table 721
Compounds of the formula I.1, where
$R^6$=cyanomethyl;
$R^5$=phenyl;
$R^4$=in each case one line of Table A.

Table 722
Compounds of the formula I.2, where
$R^6$=cyanomethyl;
$R^5$=phenyl;
$R^4$=in each case one line of Table A.

Table 723
Compounds of the formula I.3, where
$R^6$=cyanomethyl;

$R^5$=phenyl;
$R^4$=in each case one line of Table A.

Table 724
Compounds of the formula I.4, where
$R^6$=cyanomethyl;
$R^5$=phenyl;
$R^4$=in each case one line of Table A.

Table 725
Compounds of the formula I.1, where
$R^6$=n-propyl;
$R^5$=phenyl;
$R^4$=in each case one line of Table A.

Table 726
Compounds of the formula I.2, where
$R^6$=n-propyl;
$R^5$=phenyl;
$R^4$=in each case one line of Table A.

Table 727
Compounds of the formula I.3, where
$R^6$=n-propyl;
$R^5$=phenyl;
$R^4$=in each case one line of Table A.

Table 728
Compounds of the formula I.4, where
$R^6$=n-propyl;
$R^5$=phenyl;
$R^4$=in each case one line of Table A.

TABLE A

| No. | $R^4$ |
|---|---|
| 1 | H |
| 2 | $CH_3$ |
| 3 | $C_2H_5$ |
| 4 | n-$C_3H_7$ |
| 5 | i-$C_3H_7$ |
| 6 | cyclopropyl |
| 7 | n-$C_4H_9$ |
| 8 | s-$C_4H_9$ |
| 9 | i-$C_4H_9$ |
| 10 | t-$C_4H_9$ |
| 11 | n-$C_5H_{11}$ |
| 12 | i-$C_5H_{11}$ |
| 13 | neo-$C_5H_{11}$ |
| 14 | cyclopentyl |
| 15 | n-$C_6H_{13}$ |
| 16 | cyclohexyl |
| 17 | cyclobutyl |
| 18 | $CH_2CH_2Cl$ |
| 19 | $(CH_2)_4Cl$ |
| 20 | $CH_2CN$ |
| 21 | $CH_2CH_2CN$ |
| 22 | $(CH_2)_3CN$ |
| 23 | $(CH_2)_4CN$ |
| 24 | $(CH_2)_6CN$ |
| 25 | cyclohexylmethyl |
| 26 | 2-cyclohexyleth-1-yl |
| 27 | cyclopropylmethyl |
| 28 | 2-cyclopropyleth-1-yl |
| 29 | 2-methoxyeth-1-yl |
| 30 | 2-ethoxyeth-1-yl |
| 31 | 2-isopropoxyeth-1-yl |
| 32 | 3-methoxyprop-1-yl |
| 33 | 3-ethoxyprop-1-yl |
| 34 | 3-isopropoxyprop-1-yl |
| 35 | 4-methoxybut-1-yl |
| 36 | 4-isopropoxybut-1-yl |
| 37 | prop-2-en-1-yl |

TABLE A-continued

| No. | $R^4$ |
|---|---|
| 38 | but-2-en-1-yl |
| 39 | 3-methylbut-2-en-1-yl |
| 40 | 2-vinyloxyeth-1-yl |
| 41 | allyloxyeth-1-yl |
| 42 | 2-trifluoromethoxyeth-1-yl |
| 43 | 3-trifluoromethoxyprop-1-yl |
| 44 | 4-difluoromethoxybut-1-yl |
| 45 | hydroxycarbonylmethyl |
| 46 | methoxycarbonylmethyl |
| 47 | aminocarbonylmethyl |
| 48 | N-methylaminocarbonylmethyl |
| 49 | N,N-dimethylaminocarbonylmethyl |
| 50 | 2-hydroxycarbonyleth-1-yl |
| 51 | 2-methoxycarbonyleth-1-yl |
| 52 | 2-aminocarbonyleth-1-yl |
| 53 | 2-N-methylaminocarbonyleth-1-yl |
| 54 | 2-dimethylaminocarbonyleth-1-yl |
| 55 | 2-aminoeth-1-yl |
| 56 | 2-aminoprop-1-yl |
| 57 | 4-aminobut-1-yl |
| 58 | 3-dimethylaminoprop-1-yl |
| 59 | 4-aminothiocarbonylbut-1-yl |
| 60 | E-3-chloroprop-2-en-1-yl |
| 61 | Z-3-chloroprop-2-en-1-yl |
| 62 | prop-2-yn-1-yl |
| 63 | but-2-yn-1-yl |
| 64 | but-3-yn-1-yl |
| 65 | 3-chloroprop-2-yn-1-yl |
| 66 | 6-aminocarbonylhex-1-yl |
| 67 | 3-aminothiocarbonylprop-1-yl |
| 68 | 2-aminothiocarbonyleth-1-yl |
| 69 | aminothiocarbonylmethyl |
| 70 | 4-(N,N-dimethylamino)but-1-yl |
| 71 | 2-(methylthio)eth-1-yl |
| 72 | 2-(methylsulfonyl)eth-1-yl |
| 73 | 4-(methylthio)prop-1-yl |
| 74 | 4-(methylsulfonyl)prop-1-yl |
| 75 | benyzl |
| 76 | 2-F-$C_6H_4$—$CH_2$ |
| 77 | 3-F-$C_6H_4$—$CH_2$ |
| 78 | 4-F-$C_6H_4$—$CH_2$ |
| 79 | 2,3-$F_2$—$C_6H_3$—$CH_2$ |
| 80 | 2,4-$F_2$—$C_6H_3$—$CH_2$ |
| 81 | 2,5-$F_2$—$C_6H_3$—$CH_2$ |
| 82 | 2,6-$F_2$—$C_6H_3$—$CH_2$ |
| 83 | 3,4-$F_2$—$C_6H_3$—$CH_2$ |
| 84 | 3,5-$F_2$—$C_6H_3$—$CH_2$ |
| 85 | 2-Cl-$C_6H_4$—$CH_2$ |
| 86 | 3-Cl-$C_6H_4$—$CH_2$ |
| 87 | 4-Cl-$C_6H_4$—$CH_2$ |
| 88 | 2,3-$Cl_2$—$C_6H_3$—$CH_2$ |
| 89 | 2,4-$Cl_2$—$C_6H_3$—$CH_2$ |
| 90 | 2,5-$Cl_2$—$C_6H_3$—$CH_2$ |
| 91 | 2,6-$Cl_2$—$C_6H_3$—$CH_2$ |
| 92 | 3,4-$Cl_2$—$C_6H_3$—$CH_2$ |
| 93 | 3,5-$Cl_2$—$C_6H_3$—$CH_2$ |
| 94 | 2,3,4-$Cl_3$—$C_6H_2$—$CH_2$ |
| 95 | 2,3,5-$Cl_3$—$C_6H_2$—$CH_2$ |
| 96 | 2,3,6-$Cl_3$—$C_6H_2$—$CH_2$ |
| 97 | 2,4,5-$Cl_3$—$C_6H_2$—$CH_2$ |
| 98 | 2,4,6-$Cl_3$—$C_6H_2$—$CH_2$ |
| 99 | 3,4,5-$Cl_3$—$C_6H_2$—$CH_2$ |
| 100 | 2-Br—$C_6H_4$—$CH_2$ |
| 101 | 3-Br—$C_6H_4$—$CH_2$ |
| 102 | 4-Br—$C_6H_4$—$CH_2$ |
| 103 | 2,3-$Br_2$—$C_6H_3$—$CH_2$ |
| 104 | 2,4-$Br_2$—$C_6H_3$—$CH_2$ |
| 105 | 2,5-$Br_2$—$C_6H_3$—$CH_2$ |
| 106 | 2,6-$Br_2$—$C_6H_3$—$CH_2$ |
| 107 | 3,4-$Br_2$—$C_6H_3$—$CH_2$ |
| 108 | 3,5-$Br_2$—$C_6H_3$—$CH_2$ |
| 109 | 2-F,3-Cl—$C_6H_3$—$CH_2$ |
| 110 | 2-F,4-Cl—$C_6H_3$—$CH_2$ |
| 111 | 2-F,5-Cl—$C_6H_3$—$CH_2$ |
| 112 | 2-F,3-Br—$C_6H_3$—$CH_2$ |
| 113 | 2-F, 4-Br—$C_6H_3$—$CH_2$ |
| 114 | 2-F, 5-Br—$C_6H_3$—$CH_2$ |

TABLE A-continued

| No. | R$^4$ |
|---|---|
| 115 | 2-Cl, 3-Br—C$_6$H$_3$—CH$_2$ |
| 116 | 2-Cl, 4-Br—C$_6$H$_3$—CH$_2$ |
| 117 | 2-Cl, 5-Br—C$_6$H$_3$—CH$_2$ |
| 118 | 3-F, 4-Cl—C$_6$H$_3$—CH$_2$ |
| 119 | 3-F, 5-Cl—C$_6$H$_3$—CH$_2$ |
| 120 | 3-F, 6-Cl—C$_6$H$_3$—CH$_2$ |
| 121 | 3-F, 4-Br—C$_6$H$_3$—CH$_2$ |
| 122 | 3-F, 5-Br—C$_6$H$_3$—CH$_2$ |
| 123 | 3-F, 6-Br—C$_6$H$_3$—CH$_2$ |
| 124 | 3-Cl, 4-Br—C$_6$H$_3$—CH$_2$ |
| 125 | 3-Cl, 5-Br—C$_6$H$_3$—CH$_2$ |
| 126 | 3-Cl, 6-Br—C$_6$H$_3$—CH$_2$ |
| 127 | 4-F, 5-Cl—C$_6$H$_3$—CH$_2$ |
| 128 | 4-F, 6-Cl—C$_6$H$_3$—CH$_2$ |
| 129 | 4-F, 5-Br—C$_6$H$_3$—CH$_2$ |
| 130 | 4-F, 6-Br—C$_6$H$_3$—CH$_2$ |
| 131 | 4-Cl, 5-Br—C$_6$H$_3$—CH$_2$ |
| 132 | 5-F, 6-Cl—C$_6$H$_3$—CH$_2$ |
| 133 | 5-F, 6-Br—C$_6$H$_3$—CH$_2$ |
| 134 | 5-Cl, 6-Br—C$_6$H$_3$—CH$_2$ |
| 135 | 3-Br, 4-Cl, 5-Br—C$_6$H$_2$—CH$_2$ |
| 136 | 2-CN—C$_6$H$_4$—CH$_2$ |
| 137 | 3-CN—C$_6$H$_4$—CH$_2$ |
| 138 | 4-CN—C$_6$H$_4$—CH$_2$ |
| 139 | 2-NO$_2$—C$_6$H$_4$—CH$_2$ |
| 140 | 3-NO$_2$—C$_6$H$_4$—CH$_2$ |
| 141 | 4-NO$_2$—C$_6$H$_4$—CH$_2$ |
| 142 | 2-CH$_3$—C$_6$H$_4$—CH$_2$ |
| 143 | 3-CH$_3$—C$_6$H$_4$—CH$_2$ |
| 144 | 4-CH$_3$—C$_6$H$_4$—CH$_2$ |
| 145 | 2,3-(CH$_3$)$_2$—C$_6$H$_3$—CH$_2$ |
| 146 | 2,4-(CH$_3$)$_2$—C$_6$H$_3$—CH$_2$ |
| 147 | 2,5-(CH$_3$)$_2$—C$_6$H$_3$—CH$_2$ |
| 148 | 2,6-(CH$_3$)$_2$—C$_6$H$_3$—CH$_2$ |
| 149 | 3,4-(CH$_3$)$_2$—C$_6$H$_3$—CH$_2$ |
| 150 | 3,5-(CH$_3$)$_2$—C$_6$H$_3$—CH$_2$ |
| 151 | 2-C$_2$H$_5$—C$_6$H$_4$—CH$_2$ |
| 152 | 3-C$_2$H$_5$—C$_6$H$_4$—CH$_2$ |
| 153 | 4-C$_2$H$_5$—C$_6$H$_4$—CH$_2$ |
| 154 | 2-i-C$_3$H$_7$—C$_6$H$_4$—CH$_2$ |
| 155 | 3-i-C$_3$H$_7$—C$_6$H$_4$—CH$_2$ |
| 156 | 4-i-C$_3$H$_7$—C$_6$H$_4$—CH$_2$ |
| 157 | 2-cyclohexyl-C$_6$H$_4$—CH$_2$ |
| 158 | 3-cyclohexyl-C$_6$H$_4$—CH$_2$ |
| 159 | 4-cyclohexyl-C$_6$H$_4$—CH$_2$ |
| 160 | 2-vinyl-C$_6$H$_4$—CH$_2$ |
| 161 | 3-vinyl-C$_6$H$_4$—CH$_2$ |
| 162 | 4-vinyl-C$_6$H$_4$—CH$_2$ |
| 163 | 2-allyl-C$_6$H$_4$—CH$_2$ |
| 164 | 3-allyl-C$_6$H$_4$—CH$_2$ |
| 165 | 4-allyl-C$_6$H$_4$—CH$_2$ |
| 166 | 2-C$_6$H$_5$—C$_6$H$_4$—CH$_2$ |
| 167 | 3-C$_6$H$_5$—C$_6$H$_4$—CH$_2$ |
| 168 | 4-C$_6$H$_5$—C$_6$H$_4$—CH$_2$ |
| 169 | 3-CH$_3$, 5-t-C$_4$H$_9$—C$_6$H$_3$—CH$_2$ |
| 170 | 2-OH—C$_6$H$_4$—CH$_2$ |
| 171 | 3-OH—C$_6$H$_4$—CH$_2$ |
| 172 | 4-OH—C$_6$H$_4$—CH$_2$ |
| 173 | 2-OCH$_3$—C$_6$H$_4$—CH$_2$ |
| 174 | 3-OCH$_3$—C$_6$H$_4$—CH$_2$ |
| 175 | 4-OCH$_3$—C$_6$H$_4$—CH$_2$ |
| 176 | 2,3-(OCH$_3$)$_2$—C$_6$H$_3$—CH$_2$ |
| 177 | 2,4-(OCH$_3$)$_2$—C$_6$H$_3$—CH$_2$ |
| 178 | 2,5-(OCH$_3$)$_2$—C$_6$H$_3$—CH$_2$ |
| 179 | 3,4-(OCH$_3$)$_2$—C$_6$H$_3$—CH$_2$ |
| 180 | 3,5-(OCH$_3$)$_2$—C$_6$H$_3$—CH$_2$ |
| 181 | 3,4,5-(OCH$_3$)$_3$—C$_6$H$_2$—CH$_2$ |
| 182 | 2-OC$_2$H$_5$—C$_6$H$_4$—CH$_2$ |
| 183 | 3-OC$_2$H$_5$—C$_6$H$_4$—CH$_2$ |
| 184 | 4-OC$_2$H$_5$—C$_6$H$_4$—CH$_2$ |
| 185 | 2-O-(n-C$_3$H$_7$)—C$_6$H$_4$—CH$_2$ |
| 186 | 3-O-(n-C$_3$H$_7$)—C$_6$H$_4$—CH$_2$ |
| 187 | 4-O-(n-C$_3$H$_7$)—C$_6$H$_4$—CH$_2$ |
| 188 | 2-O-(i-C$_3$H$_7$)—C$_6$H$_4$—CH$_2$ |
| 189 | 3-O-(i-C$_3$H$_7$)—C$_6$H$_4$—CH$_2$ |
| 190 | 4-O-(i-C$_3$H$_7$)—C$_6$H$_4$—CH$_2$ |
| 191 | 4-O-(n-C$_4$H$_9$)—C$_6$H$_4$—CH$_2$ |
| 192 | 3-O-(t-C$_4$H$_9$)—C$_6$H$_4$—CH$_2$ |
| 193 | 4-O-(n-C$_6$H$_{13}$) -C$_6$H$_4$—CH$_2$ |
| 194 | 2-O-allyl-C$_6$H$_4$—CH$_2$ |
| 195 | 3-O-allyl-C$_6$H$_4$—CH$_2$ |
| 196 | 4-O-allyl-C$_6$H$_4$—CH$_2$ |
| 197 | 2-CF$_3$—C$_6$H$_4$—CH$_2$ |
| 198 | 3-CF$_3$—C$_6$H$_4$—CH$_2$ |
| 199 | 4-CF$_3$—C$_6$H$_4$—CH$_2$ |
| 200 | 2-acetyl-C$_6$H$_4$—CH$_2$ |
| 201 | 3-acetyl-C$_6$H$_4$—CH$_2$ |
| 202 | 4-acetyl-C$_6$H$_4$—CH$_2$ |
| 203 | 2-methoxycarbonyl-C$_6$H$_4$—CH$_2$ |
| 204 | 3-methoxycarbonyl-C$_6$H$_4$—CH$_2$ |
| 205 | 4-methoxycarbonyl-C$_6$H$_4$—CH$_2$ |
| 206 | 2-aminocarbonyl-C$_6$H$_4$—CH$_2$ |
| 207 | 3-aminocarbonyl-C$_6$H$_4$—CH$_2$ |
| 208 | 4-aminocarbonyl-C$_6$H$_4$—CH$_2$ |
| 209 | 2-dimethylaminocarbonyl-C$_6$H$_4$—CH$_2$ |
| 210 | 3-dimethylaminocarbonyl-C$_6$H$_4$—CH$_2$ |
| 211 | 4-dimethylaminocarbonyl-C$_6$H$_4$—CH$_2$ |
| 212 | 2-(N-methylaminocarbonyl)-C$_6$H$_4$—CH$_2$ |
| 213 | 3-(N-methylaminocarbonyl)-C$_6$H$_4$—CH$_2$ |
| 214 | 4-(N-methylaminocarbonyl)-C$_6$H$_4$—CH$_2$ |
| 215 | 2-H$_2$N—C$_6$H$_4$—CH$_2$ |
| 216 | 3-H$_2$N—C$_6$H$_4$—CH$_2$ |
| 217 | 4-H$_2$N—C$_6$H$_4$—CH$_2$ |
| 218 | 2-aminothiocarbonyl-C$_6$H$_4$—CH$_2$ |
| 219 | 3-aminothiocarbonyl-C$_6$H$_4$—CH$_2$ |
| 220 | 4-aminothiocarbonyl-C$_6$H$_4$—CH$_2$ |
| 221 | 2-methoxyiminomethyl-C$_6$H$_4$—CH$_2$ |
| 222 | 3-methoxyiminomethyl-C$_6$H$_4$—CH$_2$ |
| 223 | 4-methoxyiminomethyl-C$_6$H$_4$—CH$_2$ |
| 224 | 3,4-methylenedioxy-C$_6$H$_3$—CH$_2$ |
| 225 | 3,4-difluoromethylenedioxy-C$_6$H$_3$—CH$_2$ |
| 226 | 2,3-methylenedioxy-C$_6$H$_3$—CH$_2$ |
| 227 | 2-(1'-methoxyiminoeth-1'-yl)-C$_6$H$_4$—CH$_2$ |
| 228 | 3-(1'-methoxyiminoeth-1'-yl)-C$_6$H$_4$—CH$_2$ |
| 229 | 4-(1'-methoxyiminoeth-1'-yl)-C$_6$H$_4$—CH$_2$ |
| 230 | 2-SCH$_3$—C$_6$H$_4$—CH$_2$ |
| 231 | 3-SCH$_3$—C$_6$H$_4$—CH$_2$ |
| 232 | 4-SCH$_3$—C$_6$H$_4$—CH$_2$ |
| 233 | 2-SO$_2$CH$_3$—C$_6$H$_4$—CH$_2$ |
| 234 | 3-SO$_2$CH$_3$—C$_6$H$_4$—CH$_2$ |
| 235 | 4-SO$_2$CH$_3$—C$_6$H$_4$—CH$_2$ |
| 236 | 2-OCF$_3$—C$_6$H$_4$—CH$_2$ |
| 237 | 3-OCF$_3$—C$_6$H$_4$—CH$_2$ |
| 238 | 4-OCF$_3$—C$_6$H$_4$—CH$_2$ |
| 239 | 2-OCHF$_2$—C$_6$H$_4$—CH$_2$ |
| 240 | 3-OCHF$_2$—C$_6$H$_4$—CH$_2$ |
| 241 | 4-OCHF$_2$—C$_6$H$_4$—CH$_2$ |
| 242 | 3-CF$_3$, 4-OCF$_3$—C$_6$H$_3$—CH$_2$ |
| 243 | 1-naphthyl-CH$_2$ |
| 244 | 2-naphthyl-CH$_2$ |
| 245 | 2-phenoxyeth-1-yl |
| 246 | 2-(2'-chlorophenoxy)eth-1-yl |
| 247 | 2-(3'-chlorophenoxy)eth-1-yl |
| 248 | 2-(4'-chlorophenoxy)eth-1-yl |
| 249 | 2-(3',5'-dichlorophenoxy)eth-1-yl |
| 250 | 2-(2'-cyanophenoxy)eth-1-yl |
| 251 | 2-(3'-cyanophenoxy)eth-1-yl |
| 252 | 2-(4'-cyanophenoxy)eth-1-yl |
| 253 | 2-(2'-methylphenoxy)eth-1-yl |
| 254 | 2-(3'-methylphenoxy)eth-1-yl |
| 255 | 2-(4'-methylphenoxy)eth-1-yl |
| 256 | 2-(3'-t-butylphenoxy)eth-1-yl |
| 257 | 2-(4'-t-butylphenoxy)eth-1-yl |
| 258 | 2-(2'-nitrophenoxy)eth-1-yl |
| 259 | 2-(3'-nitrophenoxy)eth-1-yl |
| 260 | 2-(4'-nitrophenoxy)eth-1-yl |
| 261 | 2-(2'-methoxyphenoxy)eth-1-yl |
| 262 | 2-(3'-methoxyphenoxy)eth-1-yl |
| 263 | 2-(4'-methoxyphenoxy)eth-1-yl |
| 264 | 2-(2'-trifluoromethylphenoxy)eth-1-yl |
| 265 | 2-(3'-trifluoromethylphenoxy)eth-1-yl |
| 266 | 2-(4'-trifluoromethylphenoxy)eth-1-yl |
| 267 | 2-(2'-acetylphenoxy)eth-1-yl |
| 268 | 2-(3'-acetylphenoxy)eth-1-yl |

TABLE A-continued

| No. | R⁴ |
|---|---|
| 269 | 2-(4'-acetylphenoxy)eth-1-yl |
| 270 | 2-(2'-methoxycarbonyl)eth-1-yl |
| 271 | 2-(3'-methoxycarbonyl)eth-1-yl |
| 272 | 2-(4'-methoxycarbonyl)eth-1-yl |
| 273 | 2-(2'-dimethylaminocarbonyl)eth-1-yl |
| 274 | 2-(3'-dimethylaminocarbonyl)eth-1-yl |
| 275 | 2-(4'-dimethylaminocarbonyl)eth-1-yl |
| 276 | 2-(2'-aminothiocarbonyl)eth-1-yl |
| 277 | 2-(3'-aminothiocarbonyl)eth-1-yl |
| 278 | 2-(4'-aminothiocarbonyl)eth-1-yl |
| 279 | 2-(2'-methylsulfonyl)eth-1-yl |
| 280 | 2-(3'-methylsulfonyl)eth-1-yl |
| 281 | 2-(4'-methylsulfonyl)eth-1-yl |
| 282 | 3-phenoxyprop-1-yl |
| 283 | 3-(2'-chlorophenoxy)prop-1-yl |
| 284 | 3-(3'-chlorophenoxy)prop-1-yl |
| 285 | 3-(4'-chlorophenoxy)prop-1-yl |
| 286 | 3-(3',5'-dichlorophenoxy)prop-1-yl |
| 287 | 3-(2'-cyanophenoxy)prop-1-yl |
| 288 | 3-(3'-cyanophenoxy)prop-1-yl |
| 289 | 3-(4'-cyanophenoxy)prop-1-yl |
| 290 | 3-(2'-methylphenoxy)prop-1-yl |
| 291 | 3-(3'-methylphenoxy)prop-1-yl |
| 292 | 3-(4'-methylphenoxy)prop-1-yl |
| 293 | 3-(2'-methoxyphenoxy)prop-1-yl |
| 294 | 3-(3'-methoxyphenoxy)prop-1-yl |
| 295 | 3-(4'-methoxyphenoxy)prop-1-yl |
| 296 | 3-(2'-trifluoromethylphenoxy)prop-1-yl |
| 297 | 3-(3'-trifluoromethylphenoxy)prop-1-yl |
| 298 | 3-(4'-trifluoromethylphenoxy)prop-1-yl |
| 299 | 4-phenoxybut-1-yl |
| 300 | 2-phenyleth-1-yl |
| 301 | 2-(2'-chlorophenyl)eth-1-yl |
| 302 | 2-(3'-chlorophenyl)eth-1-yl |
| 303 | 2-(4'-chlorophenyl)eth-1-yl |
| 304 | 2-(3',5'-dichlorophenyl)eth-1-yl |
| 305 | 2-(2'-cyanophenyl)eth-1-yl |
| 306 | 2-(3'-cyanophenyl)eth-1-yl |
| 307 | 2-(4'-cyanophenyl)eth-1-yl |
| 308 | 2-(2'-methylphenyl)eth-1-yl |
| 309 | 2-(3'-methylphenyl)eth-1-yl |
| 310 | 2-(4'-methylphenyl)eth-1-yl |
| 311 | 2-(2'-methoxyphenyl)eth-1-yl |
| 312 | 2-(3'-methoxyphenyl)eth-1-yl |
| 313 | 2-(4'-methoxyphenyl)eth-1-yl |
| 314 | 2-(2'-trifluoromethylphenyl)eth-1-yl |
| 315 | 2-(3'-trifluoromethylphenyl)eth-1-yl |
| 316 | 2-(4'-trifluoromethylphenyl)eth-1-yl |
| 317 | 3-phenylprop-1-yl |
| 318 | 3-(2'-chlorophenyl)prop-1-yl |
| 319 | 3-(3'-chlorophenyl)prop-1-yl |
| 320 | 3-(4'-chlorophenyl)prop-1-yl |
| 321 | 3-(2'-cyanophenyl)prop-1-yl |
| 322 | 3-(3'-cyanophenyl)prop-1-yl |
| 323 | 3-(4'-cyanophenyl)prop-1-yl |
| 324 | 3-(2'-trifluoromethylphenyl)prop-1-yl |
| 325 | 4-phenylbut-1-yl |
| 326 | 4-(4'-chlorophenyl)but-1-yl |
| 327 | 6-(4'-chlorophenyl)hex-1-yl |
| 328 | 2-pyridylmethyl |
| 329 | 3-pyridylmethyl |
| 330 | 4-pyridylmethyl |
| 331 | 4-chloropyridin-2-ylmethyl |
| 332 | 5-chloropyridin-2-ylmethyl |
| 333 | 6-chloropyridin-2-ylmethyl |
| 334 | 5-chloropyridin-3-ylmethyl |
| 335 | 6-chloropyridin-3-ylmethyl |
| 336 | 2-chloropyridin-4-ylmethyl |
| 337 | 2-pyrimidinylmethyl |
| 338 | 4-chloropyrimidin-2-ylmethyl |
| 339 | 5-chloropyrimidin-2-ylmethyl |
| 340 | 2-chloropyrimidin-4-ylmethyl |
| 341 | 6-chloropyrimidin-4-ylmethyl |
| 342 | 2-chloropyrimidin-5-ylmethyl |
| 343 | 4-pyridazinylmethyl |
| 344 | 2-pyrazinylmethyl |
| 345 | 5-chloropyrazin-2-ylmethyl |
| 346 | 6-chloropyrazin-2-ylmethyl |
| 347 | 3-pyridazinylmethyl |
| 348 | 6-chloropyridazin-3-ylmethyl |
| 349 | 1,3,5-triazinylmethyl |
| 350 | 2-furylmethyl |
| 351 | 3-furylmethyl |
| 352 | 4-bromofur-2-ylmethyl |
| 353 | 5-chlorofur-2-ylmethyl |
| 354 | 2-thienylmethyl |
| 355 | 3-thienylmethyl |
| 356 | 5-methylthien-3-ylmethyl |
| 357 | 5-chlorothien-2-ylmethyl |
| 358 | 2-chlorothien-4-ylmethyl |
| 359 | 2-pyrrolylmethyl |
| 360 | 3-pyrrolylmethyl |
| 361 | 2-oxazolylmethyl |
| 362 | 4-methyloxazol-2-ylmethyl |
| 363 | 5-methyloxazol-2-ylmethyl |
| 364 | 4-chlorooxazol-2-ylmethyl |
| 365 | 5-chlorooxazol-2-ylmethyl |
| 366 | 4-oxazolylmethyl |
| 367 | 2-methyloxazol-4-ylmethyl |
| 368 | 5-methyloxazol-4-ylmethyl |
| 369 | 2-chlorooxazol-4-ylmethyl |
| 370 | 5-chlorooxazol-4-ylmethyl |
| 371 | 5-oxazolylmethyl |
| 372 | 2-methyloxazol-5-ylmethyl |
| 373 | 4-methyloxazol-5-ylmethyl |
| 374 | 2-chlorooxazol-5-ylmethyl |
| 375 | 4-chlorooxazol-5-ylmethyl |
| 376 | 2-thiazolylmethyl |
| 377 | 4-methylthiazol-2-ylmethyl |
| 378 | 5-methylthiazol-2-ylmethyl |
| 379 | 4-chlorothiazol-2-ylmethyl |
| 380 | 5-chlorothiazol-2-ylmethyl |
| 381 | 4-thiazolylmethyl |
| 382 | 2-methylthiazol-4-ylmethyl |
| 383 | 5-methylthiazol-4-ylmethyl |
| 384 | 2-chlorothiazol-4-ylmethyl |
| 385 | 5-chlorothiazol-4-ylmethyl |
| 386 | 5-thiazolylmethyl |
| 387 | 2-methylthiazol-5-ylmethyl |
| 388 | 4-methylthiazol-5-ylmethyl |
| 389 | 2-chlorothiazol-5-ylmethyl |
| 390 | 4-chlorothiazol-5-ylmethyl |
| 391 | 3-isoxazolylmethyl |
| 392 | 4-methylisoxazol-3-ylmethyl |
| 393 | 5-methylisoxazol-3-ylmethyl |
| 394 | 4-chloroisoxazol-3-ylmethyl |
| 395 | 5-chloroisoxazol-3-ylmethyl |
| 396 | 4-isoxazolylmethyl |
| 397 | 3-methylisoxazol-4-ylmethyl |
| 398 | 5-methylisoxazol-4-ylmethyl |
| 399 | 3-chloroisoxazol-4-ylmethyl |
| 400 | 5-chloroisoxazol-4-ylmethyl |
| 401 | 5-isoxazolylmethyl |
| 402 | 3-methylisoxazol-5-ylmethyl |
| 403 | 4-methylisoxazol-5-ylmethyl |
| 404 | 3-chloroisoxazol-5-ylmethyl |
| 405 | 4-chloroisoxazol-5-ylmethyl |
| 406 | 3-isothiazolylmethyl |
| 407 | 4-methylisothiazol-3-ylmethyl |
| 408 | 5-methylisothiazol-3-ylmethyl |
| 409 | 4-chloroisothiazol-3-ylmethyl |
| 410 | 5-chloroisothiazol-3-ylmethyl |
| 411 | 4-isothiazolylmethyl |
| 412 | 3-methylisothiazol-4-ylmethyl |
| 413 | 5-methylisothiazol-4-ylmethyl |
| 414 | 3-chloroisothiazol-4-ylmethyl |
| 415 | 5-chloroisothiazol-4-ylmethyl |
| 416 | 5-isothiazolylmethyl |
| 417 | 3-methylisothiazol-5-ylmethyl |
| 418 | 4-methylisothiazol-5-ylmethyl |
| 419 | 3-chloroisothiazol-5-ylmethyl |
| 420 | 4-chloroisothiazol-5-ylmethyl |
| 421 | 4-imidazolylmethyl |
| 422 | 1-phenylpyrazol-3-ylmethyl |

TABLE A-continued

| No. | R⁴ |
|---|---|
| 423 | 1-methylimidazol-4-ylmethyl |
| 424 | 1-phenyl-1,2,4-triazol-3-ylmethyl |
| 425 | 1,2,4-oxadiazol-3-ylmethyl |
| 426 | 5-chloro-1,2,4-oxadiazol-3-ylmethyl |
| 427 | 5-methyl-1,2,4-oxadiazol-3-ylmethyl |
| 428 | 5-trifluoromethyl-1,2,4-oxadiazol-3-ylmethyl |
| 429 | 1,3,4-oxadiazol-2-ylmethyl |
| 430 | 5-chloro-1,3,4-oxadiazol-2-ylmethyl |
| 431 | 5-methyl-1,3,4-oxadiazol-2-ylmethyl |
| 432 | 5-methoxy-1,3,4-oxadiazol-2-ylmethyl |
| 433 | 1,2,4-thiadiazol-3-ylmethyl |
| 434 | 5-chloro-1,2,4-thiadiazol-3-ylmethyl |
| 435 | 5-methyl-1,2,4-thiadiazol-3-ylmethyl |
| 436 | 1,3,4-thiadiazol-2-ylmethyl |
| 437 | 5-chloro-1,3,4-thiadiazol-2-ylmethyl |
| 438 | 5-methyl-1,3,4-thiadiazol-2-ylmethyl |
| 439 | 5-cyano-1,3,4-thiadiazol-2-ylmethyl |
| 440 | 2-(2'-pyridinyloxy)eth-1-yl |
| 441 | 2-(3'-pyridinyloxy)eth-1-yl |
| 442 | 2-(4'-pyridinyloxy)eth-1-yl |
| 443 | 2-(2'-pyrimidinyloxy)eth-1-yl |
| 444 | 2-(4'-pyrimidinyloxy)eth-1-yl |
| 445 | 2-(5'-pyrimidinyloxy)eth-1-yl |
| 446 | 2-(2'-pyrazinyloxy)eth-1-yl |
| 447 | 2-(2'-pyridazinyloxy)eth-1-yl |
| 448 | 2-(3'-pyridazinyloxy)eth-1-yl |
| 449 | 2-(1',3',5'-triazinyloxy)eth-1-yl |
| 450 | 2-(5'-methylisoxazol-3'-yloxy)eth-1-yl |
| 451 | 2-(5'-chloroisoxazol-3'-yloxy)eth-1-yl |
| 452 | 2-(2'-methoxythiazol-4'-yloxy)eth-1-yl |
| 453 | 2-(4'-chlorooxazol-2'-yloxy)eth-1-yl |
| 454 | 2-(1'-phenyl-1'H-1',2',4'-triazol-3'-yloxy)eth-1-yl |
| 455 | 2-(1'-phenylpyrazol-3'-yloxy)eth-1-yl |
| 456 | $C_6H_5$ |
| 457 | 2-F—$C_6H_4$ |
| 458 | 3-F—$C_6H_4$ |
| 459 | 4-F—$C_6H_4$ |
| 460 | 2,3-$F_2$—$C_6H_3$ |
| 461 | 2,4-$F_2$—$C_6H_3$ |
| 462 | 2,5-$F_2$—$C_6H_3$ |
| 463 | 2,6-$F_2$—$C_6H_3$ |
| 464 | 3,4-$F_2$—$C_6H_3$ |
| 465 | 3,5-$F_2$—$C_6H_3$ |
| 466 | 2-Cl—$C_6H_4$ |
| 467 | 3-Cl—$C_6H_4$ |
| 468 | 4-Cl—$C_6H_4$ |
| 469 | 2,3-$Cl_2$—$C_6H_3$ |
| 470 | 2,4-$Cl_2$—$C_6H_3$ |
| 471 | 2,5-$Cl_2$—$C_6H_3$ |
| 472 | 2,6-$Cl_2$—$C_6H_3$ |
| 473 | 3,4-$Cl_2$—$C_6H_3$ |
| 474 | 3,5-$Cl_2$—$C_6H_3$ |
| 475 | 2,3,4-$Cl_3$—$C_6H_2$ |
| 476 | 2,3,5-$Cl_3$—$C_6H_2$ |
| 477 | 2,3,6-$Cl_3$—$C_6H_2$ |
| 478 | 2,4,5-$Cl_3$—$C_6H_2$ |
| 479 | 2,4,6-$Cl_3$—$C_6H_2$ |
| 480 | 3,4,5-$Cl_3$—$C_6H_2$ |
| 481 | 2-Br—$C_6H_4$ |
| 482 | 3-Br—$C_6H_4$ |
| 483 | 4-Br—$C_6H_4$ |
| 484 | 2,3-$Br_2$—$C_6H_3$ |
| 485 | 2,4-$Br_2$—$C_6H_3$ |
| 486 | 2,5-$Br_2$—$C_6H_3$ |
| 487 | 2,6-$Br_2$—$C_6H_3$ |
| 488 | 3,4-$Br_2$—$C_6H_3$ |
| 489 | 3,5-$Br_2$—$C_6H_3$ |
| 490 | 2-F, 3-Cl—$C_6H_3$ |
| 491 | 2-F, 4-Cl—$C_6H_3$ |
| 492 | 2-F, 5-Cl—$C_6H_3$ |
| 493 | 2-F, 3-Br—$C_6H_3$ |
| 494 | 2-F, 4-Br—$C_6H_3$ |
| 495 | 2-F, 5-Br—$C_6H_3$ |
| 496 | 2-Cl, 3-Br—$C_6H_3$ |
| 497 | 2-Cl, 4-Br—$C_6H_3$ |
| 498 | 2-Cl, 5-Br—$C_6H_3$ |
| 499 | 3-F, 4-Cl—$C_6H_3$ |
| 500 | 3-F, 5-Cl—$C_6H_3$ |
| 501 | 3-F, 6-Cl—$C_6H_3$ |
| 502 | 3-F, 4-Br—$C_6H_3$ |
| 503 | 3-F, 5-Br—$C_6H_3$ |
| 504 | 3-F, 6-Br—$C_6H_3$ |
| 505 | 3-Cl, 4-Br—$C_6H_3$ |
| 506 | 3-Cl, 5-Br—$C_6H_3$ |
| 507 | 3-Cl, 6-Br—$C_6H_3$ |
| 508 | 4-F, 5-Cl—$C_6H_3$ |
| 509 | 4-F, 6-Cl—$C_6H_3$ |
| 510 | 4-F, 5-Br—$C_6H_3$ |
| 511 | 4-F, 6-Br—$C_6H_3$ |
| 512 | 4-Cl, 5-Br—$C_6H_3$ |
| 513 | 5-F, 6-Cl—$C_6H_3$ |
| 514 | 5-F, 6-Br—$C_6H_3$ |
| 515 | 5-Cl, 6-Br—$C_6H_3$ |
| 516 | 3-Br, 4-Cl, 5-Br—$C_6H_2$ |
| 517 | 2-CN—$C_6H_4$ |
| 518 | 3-CN—$C_6H_4$ |
| 519 | 4-CN—$C_6H_4$ |
| 520 | 2-$NO_2$—$C_6H_4$ |
| 521 | 3-$NO_2$—$C_6H_4$ |
| 522 | 4-$NO_2$—$C_6H_4$ |
| 523 | 2-$CH_3$—$C_6H_4$ |
| 524 | 3-$CH_3$—$C_6H_4$ |
| 525 | 4-$CH_3$—$C_6H_4$ |
| 526 | 2,3-$(CH_3)_2$—$C_6H_3$ |
| 527 | 2,4-$(CH_3)_2$—$C_6H_3$ |
| 528 | 2,5-$(CH_3)_2$—$C_6H_3$ |
| 529 | 2,6-$(CH_3)_2$—$C_6H_3$ |
| 530 | 3,4-$(CH_3)_2$—$C_6H_3$ |
| 531 | 3,5-$(CH_3)_2$—$C_6H_3$ |
| 532 | 2-$C_2H_5$—$C_6H_4$ |
| 533 | 3-$C_2H_5$—$C_6H_4$ |
| 534 | 4-$C_2H_5$—$C_6H_4$ |
| 535 | 2-i-$C_3H_7$—$C_6H_4$ |
| 536 | 3-i-$C_3H_7$—$C_6H_4$ |
| 537 | 4-i-$C_3H_7$—$C_6H_4$ |
| 538 | 3-tert-$C_4H_9$—$C_6H_4$ |
| 539 | 4-tert-$C_4H_9$—$C_6H_4$ |
| 540 | 2-vinyl-$C_6H_4$ |
| 541 | 3-vinyl-$C_6H_4$ |
| 542 | 4-vinyl-$C_6H_4$ |
| 543 | 2-allyl-$C_6H_4$ |
| 544 | 3-allyl-$C_6H_4$ |
| 545 | 4-allyl-$C_6H_4$ |
| 546 | 2-$C_6H_5$—$C_6H_4$ |
| 547 | 3-$C_6H_5$—$C_6H_4$ |
| 548 | 4-$C_6H_5$—$C_6H_4$ |
| 549 | 3-$CH_3$, 5-tert-$C_4H_9$—$C_6H_3$ |
| 550 | 2-OH—$C_6H_4$ |
| 551 | 3-OH—$C_6H_4$ |
| 552 | 4-OH—$C_6H_4$ |
| 553 | 2-$OCH_3$—$C_6H_4$ |
| 554 | 3-$OCH_3$—$C_6H_4$ |
| 555 | 4-$OCH_3$—$C_6H_4$ |
| 556 | 2,3-$(OCH_3)_2$—$C_6H_3$ |
| 557 | 2,4-$(OCH_3)_2$—$C_6H_3$ |
| 558 | 2,5-$(OCH_3)_2$—$C_6H_3$ |
| 559 | 3,4-$(OCH_3)_2$—$C_6H_3$ |
| 560 | 3,5-$(OCH_3)_2$—$C_6H_3$ |
| 561 | 3,4,5-$(OCH_3)3$-$C_6H_2$ |
| 562 | 2-$OC_2H_5$—$C_6H_4$ |
| 563 | 3-$OC_2H_5$—$C_6H_4$ |
| 564 | 4-$OC_2H_5$—$C_6H_4$ |
| 565 | 2-O-(n-$C_3H_7$)—$C_6H_4$ |
| 566 | 3-O-(n-$C_3H_7$)—$C_6H_4$ |
| 567 | 4-O-(n-$C_3H_7$)—$C_6H_4$ |
| 568 | 2-O-(i-$C_3H_7$)—$C_6H_4$ |
| 569 | 3-O-(i-$C_3H_7$)—$C_6H_4$ |
| 570 | 4-O-(i-$C_3H_7$)—$C_6H_4$ |
| 571 | 4-O-(n-$C_4H_9$)—$C_6H_4$ |
| 572 | 3-O-(t-$C_4H_9$)—$C_6H_4$ |
| 573 | 4-O-(t-$C_4H_9$)—$C_6H_4$ |
| 574 | 2-O-allyl-$C_6H_4$ |
| 575 | 3-O-allyl-$C_6H_4$ |
| 576 | 4-O-allyl-$C_6H_4$ |

TABLE A-continued

| No. | R$^4$ |
|---|---|
| 577 | 2-CF$_3$—C$_6$H$_4$ |
| 578 | 3-CF$_3$—C$_6$H$_4$ |
| 579 | 4-CF$_3$—C$_6$H$_4$ |
| 580 | 2-acetyl-C$_6$H$_4$ |
| 581 | 3-acetyl-C$_6$H$_4$ |
| 582 | 4-acetyl-C$_6$H$_4$ |
| 583 | 2-methoxycarbonyl-C$_6$H$_4$ |
| 584 | 3-methoxycarbonyl-C$_6$H$_4$ |
| 585 | 4-methoxycarbonyl-C$_6$H$_4$ |
| 586 | 2-aminocarbonyl-C$_6$H$_4$ |
| 587 | 3-aminocarbonyl-C$_6$H$_4$ |
| 588 | 4-aminocarbonyl-C$_6$H$_4$ |
| 589 | 2-dimethylaminocarbonyl-C$_6$H$_4$ |
| 590 | 3-dimethylaminocarbonyl-C$_6$H$_4$ |
| 591 | 4-dimethylaminocarbonyl-C$_6$H$_4$ |
| 592 | 2-(N-methylaminocarbonyl)-C$_6$H$_4$ |
| 593 | 3-(N-methylaminocarbonyl)-C$_6$H$_4$ |
| 594 | 4-(N-methylaminocarbonyl)-C$_6$H$_4$ |
| 595 | 2-H$_2$N—C$_6$H$_4$ |
| 596 | 3-H$_2$N—C$_6$H$_4$ |
| 597 | 4-H$_2$N—C$_6$H$_4$ |
| 598 | 2-aminothiocarbonyl-C$_6$H$_4$ |
| 599 | 3-aminothiocarbonyl-C$_6$H$_4$ |
| 600 | 4-aminothiocarbonyl-C$_6$H$_4$ |
| 601 | 2-methoxyiminomethyl-C$_6$H$_4$ |
| 602 | 3-methoxyiminomethyl-C$_6$H$_4$ |
| 603 | 4-methoxyiminomethyl-C$_6$H$_4$ |
| 604 | 3,4-methylenedioxy-C$_6$H$_3$ |
| 605 | 3,4-difluoromethylenedioxy-C$_6$H$_3$ |
| 606 | 2,3-methylenedioxy-C$_6$H$_3$ |
| 607 | 2-(1'-methoxyiminoeth-1'-yl)-C$_6$H$_4$ |
| 608 | 3-(1'-methoxyiminoeth-1'-yl)-C$_6$H$_4$ |
| 609 | 4-(1'-methoxyiminoeth-1'-yl)-C$_6$H$_4$ |
| 610 | 2-SCH$_3$—C$_6$H$_4$ |
| 611 | 3-SCH$_3$—C$_6$H$_4$ |
| 612 | 4-SCH$_3$—C$_6$H$_4$ |
| 613 | 2-SO$_2$CH$_3$—C$_6$H$_4$ |
| 614 | 3-SO$_2$CH$_3$—C$_6$H$_4$ |
| 615 | 4-SO$_2$CH$_3$—C$_6$H$_4$ |
| 616 | 2-OCF$_3$—C$_6$H$_4$ |
| 617 | 3-OCF$_3$—C$_6$H$_4$ |
| 618 | 4-OCF$_3$—C$_6$H$_4$ |
| 619 | 2-OCHF$_2$—C$_6$H$_4$ |
| 620 | 3-OCHF$_2$—C$_6$H$_4$ |
| 621 | 4-OCHF$_2$—C$_6$H$_4$ |
| 622 | 3-CF$_3$, 4-OCF$_3$—C$_6$H$_3$ |
| 623 | 2-NHCH$_3$—C$_6$H$_4$ |
| 624 | 3-NHCH$_3$—C$_6$H$_4$ |
| 625 | 4-NHCH$_3$—C$_6$H$_4$ |
| 626 | 2-N(CH$_3$)$_2$—C$_6$H$_4$ |
| 627 | 3-N(CH$_3$)$_2$—C$_6$H$_4$ |
| 628 | 4-N(CH$_3$)$_2$—C$_6$H$_4$ |
| 629 | 2-ethoxycarbonyl-C$_6$H$_4$ |
| 630 | 3-ethoxycarbonyl-C$_6$H$_4$ |
| 631 | 4-ethoxycarbonyl-C$_6$H$_4$ |
| 632 | 2-CH$_2$CH$_2$F—C$_6$H$_4$ |
| 633 | 3-CH$_2$CH$_2$F—C$_6$H$_4$ |
| 634 | 4-CH$_2$CH$_2$F—C$_6$H$_4$ |
| 635 | 2-CH$_2$CF$_3$—C$_6$H$_4$ |
| 636 | 3-CH$_2$CF$_3$—C$_6$H$_4$ |
| 637 | 4-CH$_2$CF$_3$—C$_6$H$_4$ |
| 638 | 2-CF$_2$CHF$_2$—C$_6$H$_4$ |
| 639 | 3-CF$_2$CHF$_2$—C$_6$H$_4$ |
| 640 | 4-CF$_2$CHF$_2$—C$_6$H$_4$ |
| 641 | 2-CHF$_2$—C$_6$H$_4$ |
| 642 | 3-CHF$_2$—C$_6$H$_4$ |
| 643 | 4-CHF$_2$—C$_6$H$_4$ |
| 644 | 2-(1'-oxo-n-prop-1-yl)-C$_6$H$_4$ |
| 645 | 3-(1'-oxo-n-prop-1-yl)-C$_6$H$_4$ |
| 646 | 4-(1'-oxo-n-prop-1-yl)-C$_6$H$_4$ |
| 647 | 2-(1'-oxoisoprop-1-yl)-C$_6$H$_4$ |
| 648 | 3-(1'-oxoisoprop-1-yl)-C$_6$H$_4$ |
| 649 | 4-(1'-oxoisoprop-1-yl)-C$_6$H$_4$ |
| 650 | 3-cyclopropyl-C$_6$H$_4$ |
| 651 | 4-cyclopropyl-C$_6$H$_4$ |
| 652 | 4-cyclohexyl-C$_6$H$_4$ |
| 653 | 1-naphthyl |
| 654 | 2-naphthyl |
| 655 | 2-pyridyl |
| 656 | 3-pyridyl |
| 657 | 4-pyridyl |
| 658 | 5-CH$_3$-pyridin-2-yl |
| 659 | 5-Cl-pyridin-2-yl |
| 660 | 6-Cl-pyridin-2-yl |
| 661 | 3,5-Cl$_2$-pyridin-2-yl |
| 662 | 6-OCH$_3$-pyridin-2-yl |
| 663 | 6-CH$_3$-pyridin-2-yl |
| 664 | 6-Cl-pyridin-3-yl |
| 665 | 6-CH$_3$-pyridin-3-yl |
| 666 | 6-OCH$_3$-pyridin-3-yl |
| 667 | 2-pyrimidinyl |
| 668 | 4-OCH$_3$-pyrimidin-2-yl |
| 669 | 4-OC$_2$H$_5$-pyrimidin-2-yl |
| 670 | 4-Cl-pyrimidin-2-yl |
| 671 | 4-CH$_3$-pyrimidin-2-yl |
| 672 | 5-CH$_3$-pyrimidin-2-yl |
| 673 | 5-Cl-pyrimidin-2-yl |
| 674 | 5-OCH$_3$-pyrimidin-2-yl |
| 675 | 5-OC$_2$H$_5$-pyrimidin-2-yl |
| 676 | 4-pyrimidinyl |
| 677 | 2-Cl-pyrimidin-4-yl |
| 678 | 2-OCH$_3$-pyrimidin-4-yl |
| 679 | 2-CH$_3$-pyrimidin-4-yl |
| 680 | 6-Cl-pyrimidin-4-yl |
| 681 | 6-CH$_3$-pyrimidin-4-yl |
| 682 | 6-OCH$_3$-pyrimidin-4-yl |
| 683 | 5-pyrimidinyl |
| 684 | 2-CH$_3$-pyrimidin-5-yl |
| 685 | 2-Cl-pyrimidin-5-yl |
| 686 | 2-OCH$_3$-pyrimidin-5-yl |
| 687 | 2-OC$_2$H$_5$-pyrimidin-5-yl |
| 688 | 2-furyl |
| 689 | 4-C$_2$H$_5$-fur-2-yl |
| 690 | 4-CH$_3$-fur-2-yl |
| 691 | 4-Cl-fur-2-yl |
| 692 | 4-CN-fur-2-yl |
| 693 | 5-CH$_3$-fur-2-yl |
| 694 | 5-Cl-fur-2-yl |
| 695 | 5-CN-fur-2-yl |
| 696 | 3-furyl |
| 697 | 5-CH$_3$-fur-3-yl |
| 698 | 5-Cl-fur-3-yl |
| 699 | 5-CN-fur-3-yl |
| 700 | 2-thienyl |
| 701 | 4-CH$_3$-thien-2-yl |
| 702 | 4-Cl-thien-2-yl |
| 703 | 4-CN-thien-2-yl |
| 704 | 5-CH$_3$-thien-2-yl |
| 705 | 5-Cl-thien-2-yl |
| 706 | 5-CN-thien-2-yl |
| 707 | 3-thienyl |
| 708 | 5-CH$_3$-thien-3-yl |
| 709 | 5-Cl-thien-3-yl |
| 710 | 5-CN-thien-3-yl |
| 711 | 4-CH$_3$-thien-3-yl |
| 712 | 5-F-thien-3-yl |
| 713 | 2-oxazolyl |
| 714 | 4-CH$_3$-oxazol-2-yl |
| 715 | 4-Cl-oxazol-2-yl |
| 716 | 4-CN-oxazol-2-yl |
| 717 | 5-CH$_3$-oxazol-2-yl |
| 718 | 5-Cl-oxazol-2-yl |
| 719 | 5-CN-oxazol-2-yl |
| 720 | 4-oxazolyl |
| 721 | 2-CH$_3$-oxazol-4-yl |
| 722 | 2-Cl-oxazol-4-yl |
| 723 | 2-CN-oxazol-4-yl |
| 724 | 5-oxazolyl |
| 725 | 2-CH$_3$-oxazol-5-yl |
| 726 | 2-Cl-oxazol-5-yl |
| 727 | 2-CN-oxazol-5-yl |
| 728 | 3-isoxazolyl |
| 729 | 5-CH$_3$-isoxazol-3-yl |
| 730 | 5-Cl-isoxazol-3-yl |

TABLE A-continued

| No. | R⁴ |
|---|---|
| 731 | 5-CN-isoxazol-3-yl |
| 732 | 5-isoxazolyl |
| 733 | 3-CH₃-isoxazol-5-yl |
| 734 | 3-Cl-isoxazol-5-yl |
| 735 | 3-CN-isoxazol-5-yl |
| 736 | 2-thiazolyl |
| 737 | 4-CH₃-thiazol-2-yl |
| 738 | 4-Cl-thiazol-2-yl |
| 739 | 4-CN-thiazol-2-yl |
| 740 | 5-CH₃-thiazol-2-yl |
| 741 | 5-Cl-thiazol-2-yl |
| 742 | 5-CN-thiazol-2-yl |
| 743 | 4-thiazolyl |
| 744 | 2-CH₃-thiazol-4-yl |
| 745 | 2-Cl-thiazol-4-yl |
| 746 | 2-CN-thiazol-4-yl |
| 747 | 2-SCH₃-thiazol-4-yl |
| 748 | 5-thiazolyl |
| 749 | 2-CH₃-thiazol-5-yl |
| 750 | 2-Cl-thiazol-5-yl |
| 751 | 2-CN-thiazol-5-yl |
| 752 | 3-isothiazolyl |
| 753 | 5-CH₃-isothiazol-3-yl |
| 754 | 5-Cl-isothiazol-3-yl |
| 755 | 5-CN-isothiazol-3-yl |
| 756 | 5-isothiazolyl |
| 757 | 3-CH₃-isothiazol-5-yl |
| 758 | 3-Cl-isothiazol-5-yl |
| 759 | 3-CN-isothiazol-5-yl |
| 760 | 2-imidazolyl |
| 761 | 4-CH₃-imidazol-2-yl |
| 762 | 4-Cl-imidazol-2-yl |
| 763 | 4-CN-imidazol-2-yl |
| 764 | 1-CH₃-imidazol-2-yl |
| 765 | 1-CH₃, 4-Cl-imidazol-2-yl |
| 766 | 1,4-(CH₃)₂-imidazol-2-yl |
| 767 | 1-CH₃, 5-Cl-imidazol-2-yl |
| 768 | 1,5-(CH₃)₂-imidazol-2-yl |
| 769 | 4-imidazolyl |
| 770 | 2-CH₃-imidazol-4-yl |
| 771 | 2-Cl-imidazol-4-yl |
| 772 | 1-CH₃-imidazol-4-yl |
| 773 | 1,2-(CH₃)₂-imidazol-4-yl |
| 774 | 1-CH₃, 2-Cl-imidazol-4-yl |
| 775 | 1-CH₃-imidazol-5-yl |
| 776 | 1-CH₃, 3-Cl-imidazol-5-yl |
| 777 | 1,2-(CH₃)₂-imidazol-5-yl |
| 778 | 3-pyrazolyl |
| 779 | 5-CH₃-pyrazol-3-yl |
| 780 | 5-Cl-pyrazol-3-yl |
| 781 | 5-CN-pyrazol-3-yl |
| 782 | 1-CH₃-pyrazol-3-yl |
| 783 | 1-CH₃, 4-Cl-pyrazol-3-yl |
| 784 | 1-CH₃, 5-Cl-pyrazol-3-yl |
| 785 | 1,5-(CH₃)₂-pyrazol-3-yl |
| 786 | 1-CH₃-pyrazol-5-yl |
| 787 | 1-CH₃, 3-Cl-pyrazol-5-yl |
| 788 | 1,3-(CH₃)₂-pyrazol-5-yl |
| 789 | 4-pyrazolyl |
| 790 | 3-Cl-pyrazol-4-yl |
| 791 | 3-CH₃-pyrazol-4-yl |
| 792 | 1-CH₃-pyrazol-4-yl |
| 793 | 1-CH₃, 3-Cl-pyrazol-4-yl |
| 794 | 1,3-(CH₃)₂-pyrazol-4-yl |
| 795 | 1,3,4-oxadiazol-5-yl |
| 796 | 2-CH₃-1,3,4-oxadiazol-5-yl |
| 797 | 2-Cl-1,3,4-oxadiazol-5-yl |
| 798 | 2-CF₃-1,3,4-oxadiazol-5-yl |
| 799 | 2-i-C₃H₇-1,3,4-oxadiazol-5-yl |
| 800 | 2-OCH₃-1,3,4-oxadiazol-5-yl |
| 801 | 1,2,4-oxadiazol-3-yl |
| 802 | 5-CH₃-1,2,4-oxadiazol-3-yl |
| 803 | 5-i-C₃H₇-1,2,4-oxadiazol-3-yl |
| 804 | 5-Cl-1,2,4-oxadiazol-3-yl |
| 805 | 5-CF₃-1,2,4-oxadiazol-3-yl |
| 806 | 1,2,4-triazol-3-yl |
| 807 | 1-CH₃-1,2,4-triazol-3-yl |
| 808 | 3-fluoropyridin-2-yl |
| 809 | 3-chloropyridin-2-yl |
| 810 | 3-bromopyridin-2-yl |
| 811 | 3-methylpyridin-2-yl |
| 812 | 3-trifluoromethylpyridin-2-yl |
| 813 | 3-methoxypyridin-2-yl |
| 814 | 4-fluoropyridin-2-yl |
| 815 | 4-chloropyridin-2-yl |
| 816 | 4-bromopyridin-2-yl |
| 817 | 4-methylpyridin-2-yl |
| 818 | 4-trifluoromethylpyridin-2-yl |
| 819 | 4-methoxypyridin-2-yl |
| 820 | 5-fluoropyridin-2-yl |
| 821 | 5-bromopyridin-2-yl |
| 822 | 6-trifluoromethylpyridin-2-yl |
| 823 | 2-fluoropyridin-3-yl |
| 824 | 2-chloropyridin-3-yl |
| 825 | 2-bromopyridin-3-yl |
| 826 | 2-methylpyridin-3-yl |
| 827 | 2-trifluoromethylpyridin-3-yl |
| 828 | 3-methoxypyridin-3-yl |
| 829 | 4-fluoropyridin-3-yl |
| 830 | 4-chloropyridin-3-yl |
| 831 | 4-bromopyridin-3-yl |
| 832 | 4-methylpyridin-3-yl |
| 833 | 4-trifluoromethylpyridin-3-yl |
| 834 | 4-methoxypyridin-3-yl |
| 835 | 5-fluoropyridin-3-yl |
| 836 | 5-chloropyridin-3-yl |
| 837 | 5-bromopyridin-3-yl |
| 838 | 5-methylpyridin-3-yl |
| 839 | 5-trifluoromethylpyridin-3-yl |
| 840 | 5-methoxypyridin-3-yl |
| 841 | 6-fluoropyridin-3-yl |
| 842 | 6-bromopyridin-3-yl |
| 843 | 6-trifluoromethylpyridin-3-yl |
| 844 | 2-fluoropyridin-4-yl |
| 845 | 2-chloropyridin-4-yl |
| 846 | 2-bromopyridin-4-yl |
| 847 | 2-methylpyridin-4-yl |
| 848 | 2-trifluoromethylpyridin-4-yl |
| 849 | 2-methoxypyridin-4-yl |
| 850 | 3-fluoropyridin-4-yl |
| 851 | 3-chloropyridin-4-yl |
| 852 | 3-bromopyridin-4-yl |
| 853 | 3-methylpyridin-4-yl |
| 854 | 3-trifluoromethylpyridin-4-yl |
| 855 | 3-methoxypyridin-4-yl |
| 856 | 4-fluoropyrimidin-2-yl |
| 857 | 4-bromopyrimidin-2-yl |
| 858 | 4-trifluoromethylpyrimidin-2-yl |
| 859 | 5-fluoropyrimidin-2-yl |
| 860 | 5-bromopyrimidin-2-yl |
| 861 | 5-trifluoromethylpyrimidin-2-yl |
| 862 | 2-fluoropyrimidin-4-yl |
| 863 | 2-bromopyrimidin-4-yl |
| 864 | 2-trifluoromethylpyrimidin-4-yl |
| 865 | 2-trifluoromethoxypyrimidin-4-yl |
| 866 | 5-fluoropyrimidin-4-yl |
| 867 | 5-chloropyrimidin-4-yl |
| 868 | 5-bromopyrimidin-4-yl |
| 869 | 5-methoxypyrimidin-4-yl |
| 870 | 5-trifluoromethylpyrimidin-4-yl |
| 871 | 5-methoxypyrimidin-4-yl |
| 872 | 6-fluoropyrimidin-4-yl |
| 873 | 6-bromopyrimidin-4-yl |
| 874 | 6-trifluoromethylpyrimidin-4-yl |
| 875 | 2-fluoropyrimidin-5-yl |
| 876 | 2-bromopyrimidin-5-yl |
| 877 | 2-trifluoromethylpyrimidin-5-yl |
| 878 | 4-fluoropyrimidin-5-yl |
| 879 | 4-chloropyrimidin-5-yl |
| 880 | 4-bromopyrimidin-5-yl |
| 881 | 4-methylpyrimidin-5-yl |
| 882 | 4-trifluoromethylpyrimidin-5-yl |
| 883 | 3-fluoro-5-trifluoromethylpyridin-2-yl |
| 884 | 3,6-dichloro-5-trifluoromethylpyridin-2-yl |

TABLE A-continued

| No. | R⁴ |
|---|---|
| 885 | 5,6-dichloro-3-trifluoromethylpyridin-2-yl |
| 886 | 5-chloro-3-trifluoromethylpyridin-2-yl |
| 887 | 3-chloro-5-trifluoromethylpyridin-2-yl |
| 888 | 6-chloro-4-cyanopyridin-2-yl |
| 889 | 3-cyano-5-nitropyridin-2-yl |
| 890 | 2-chloro-6-fluoropyridin-4-yl |
| 891 | 6-chloro-4-fluoropyridin-2-yl |
| 892 | 4,6-difluoropyridin-2-yl |
| 893 | 3,5-dichloro-6-fluoropyridin-2-yl |
| 894 | 6-methoxy-3-nitropyridin-2-yl |
| 895 | 4-cyano-6-fluoropyridin-2-yl |
| 896 | 6-chloro-5-cyanopyridin-2-yl |
| 897 | 6-chloro-3-cyanopyridin-2-yl |
| 898 | 4-cyano-3,5,6-trifluoropyridin-2-yl |
| 899 | 6-chloro-5-nitropyridin-2-yl |
| 900 | 6-chloro-3-nitropyridin-2-yl |
| 901 | 5-cyano-6-fluoropyridin-2-yl |
| 902 | 3-cyano-6-fluoropyridin-2-yl |
| 903 | 4,6-dicyanopyridin-2-yl |
| 904 | 5-trichloromethylpyridin-2-yl |
| 905 | 5-cyanopyridin-2-yl |
| 906 | 5-bromo-4-trifluoromethylpyridin-2-yl |
| 907 | 3-nitro-5-trifluoromethylpyridin-2-yl |
| 908 | 5-aminopyridin-2-yl |
| 909 | 2,3,5,6-tetrafluoropyridin-4-yl |
| 910 | 5-nitropyridin-2-yl |
| 911 | 4-methyl-5-nitroypridin-2-yl |
| 912 | 5-difluoromethylpyridin-2-yl |
| 913 | 5-fluoromethylpyridin-2-yl |
| 914 | 4,6-difluoropyrimidin-2-yl |
| 915 | 2,6-difluoropyrimidin-4-yl |
| 916 | 2-chloro-6-trichloromethylpyrimidin-4-yl |
| 917 | 2,6-dichloropyrimidin-4-yl |
| 918 | 5-methoxycarbonylpyridin-2-yl |
| 919 | 5-chloro-6-fluoropyridin-2-yl |
| 920 | 5-chloro-6-hydroxypyridin-2-yl |
| 921 | 5-chloro-6-methoxypyridin-2-yl |
| 922 | 5-chloro-cyanopyridin-2-yl |
| 923 | 5,6-dichloropyridin-2-yl |
| 924 | 6-bromo-5-chloropyridin-2-yl |
| 925 | 5-bromo-6-fluoropyridin-2-yl |
| 926 | 5-bromo-6-chloropyridin-2-yl |
| 927 | 5-bromo-6-cyanopyridin-2-yl |
| 928 | 5-bromo-6-hydroxypyridin-2-yl |
| 929 | 5-bromo-6-methoxypyridin-2-yl |
| 930 | 5,6-dibromopyridin-2-yl |
| 931 | 4-cyanopyridin-2-yl |
| 932 | 6-cyanopyridin-2-yl |
| 933 | 4-chloro-6-methylpyrimidin-2-yl |
| 934 | 2-chloro-fluoropyridin-4-yl |
| 935 | 5-bromo-4-trifluoromethylpyridin-2-yl |
| 936 | 4,5-dichloropyridin-2-yl |
| 937 | 4,5-dibromopyridin-2-yl |
| 938 | 5,6-dichloropyridin-2-yl |
| 939 | 4,6-dichloropyridin-2-yl |
| 940 | 4,6-dibromopyridin-2-yl |
| 941 | 5,6-dibromopyridin-2-yl |
| 942 | 4-bromo-5-chloropyridin-2-yl |
| 943 | 6-bromo-5-chloropyridin-2-yl |
| 944 | 5-bromo-4-chloropyridin-2-yl |
| 945 | 5-bromo-4-chloropyridin-2-yl |
| 946 | 6-bromo-4-chloropyridin-2-yl |
| 947 | 4-bromo-6-chloropyridin-2-yl |
| 948 | 6-chloro-4-methoxypyridin-2-yl |
| 949 | 6-bromo-4-methoxypyridin-2-yl |
| 950 | 6-chlorochinazolin-2-yl |
| 951 | quinazolin-2-yl |
| 952 | 4-cyanopyridin-2-yl |
| 953 | 6-cyanopyridin-2-yl |
| 954 | 5-hydroxymethylpyridin-2-yl |
| 955 | 6-chloro-4-trifluoromethylpyridin-2-yl |
| 956 | 6-chloro-4-trifluoromethylpyridin-2-yl |
| 957 | 6-chloro-4-methylpyridin-2-yl |
| 958 | 2,5-dichloro-6-cyanopyridin-2-yl |
| 959 | 2,5-dichloro-6-carboxypyridin-2-yl |
| 960 | 2,5-dichloro-6-methoxycarbonyl-pyridin-2-yl |
| 961 | 6-trifluoromethylpyridin-2-yl |
| 962 | 6-methoxycarbonylpyridin-2-yl |
| 963 | 6-carboxypyridin-2-yl |
| 964 | 4-phenoxypyridin-2-yl |
| 965 | 5-phenoxypyridin-2-yl |
| 966 | 6-phenoxypyridin-2-yl |
| 967 | 4-phenoxypyrimidin-4-yl |
| 968 | 4-(4-methylphenoxy)pyrimidin-4-yl |
| 969 | 4-phenoxypyrimidin-2-yl |
| 970 | 4-(2-fluorophenoxy)pyrimidin-2-yl |
| 971 | 4-phenoxypyrimidin-6-yl |
| 972 | 4-(4-chlorophenoxy)pyrimidin-6-yl |
| 973 | 4-(2-pyridyloxy)pyrimidin-6-yl |
| 974 | 4-(6-chloro-2-pyridyloxy)pyrimidin-6-yl |
| 975 | 4-(3-pyridyloxy)pyrimidin-6-yl |
| 976 | 4-(2-methyl-3-pyridyloxy)pyrimidin-6-yl |
| 977 | 4-(4-pyridyloxy)pyrimidin-6-yl |
| 978 | 5-bromo-2-thienyl |
| 979 | 5-nitro-2-thienyl |
| 980 | 2-chloro-3-thienyl |
| 981 | 2-bromo-3-thienyl |
| 982 | 1-methyl-3-pyrrolyl |
| 983 | 1-methyl-2-pyrrolyl |
| 984 | 1-benzofuran-2-yl |
| 985 | 1-benzofuran-3-yl |
| 986 | 1-benzothiophen-2-yl |
| 987 | 1-benzothiophen-3-yl |
| 988 | 3-pyrrolyl |
| 989 | 2-pyrrolyl |
| 990 | 3-indolyl |
| 991 | 2-indolyl |
| 992 | 1-methyl-3-indolyl |
| 993 | 1-methyl-2-indolyl |
| 994 | isoxazol-4-yl |
| 995 | isothiazol-4-yl |
| 996 | 1,2-benzisoxazol-3-yl |
| 997 | 1,2-benzisothiazol-3-yl |
| 998 | 1-methylindazol-3-yl |
| 999 | benzoxazol-2-yl |
| 1000 | 5-chlorobenzoxazol-2-yl |
| 1001 | 6-fluorobenzoxazol-2-yl |
| 1002 | benzthiazol-2-yl |
| 1003 | 5-fluorobenzthiazol-2-yl |
| 1004 | 6-fluorobenzthiazol-2-yl |
| 1005 | pyrido[3,2-d]thiazol-2-yl |
| 1006 | (6-chloropyrido)[3,2-d]thiazol-2-yl |
| 1007 | 1-methyl-1,2,3-triazol-5-yl |
| 1008 | 1-methyl-1,2,3-triazol-4-yl |
| 1009 | 1-methyl-1,2,4-triazol-5-yl |
| 1010 | 1-methyl-1,2,3,4-tetrazol-5-yl |
| 1011 | 2-methyl-1,2,3,4-tetrazol-5-yl |
| 1012 | 5-trifluoromethyl-1,3,4-thiadiazol-2-yl |
| 1013 | 6-chlorobenzoxazol-2-yl |
| 1014 | 5-fluorobenzoxazol-2-yl |
| 1015 | 5-nitrothiazol-2-yl |
| 1016 | 1-CH(CH$_3$)$_2$-pyrrol-3-yl |
| 1017 | 1-C(CH$_3$)$_3$-pyrrol-3-yl |
| 1018 | 1-cyclopropylpyrrol-3-yl |
| 1019 | 1-C$_6$H$_5$-pyrrol-3-yl |
| 1020 | 1-(2-CH$_3$—C$_6$H$_4$)pyrrol-3-yl |
| 1021 | 1-(3-CH$_3$—C$_6$H$_4$)pyrrol-3-yl |
| 1022 | 1-(4-CH$_3$—C$_6$H$_4$)pyrrol-3-yl |
| 1023 | 1-(3-OCH$_3$—C$_6$H$_4$)pyrrol-3-yl |
| 1024 | 1-(4-OCH$_3$—C$_6$H$_4$)pyrrol-3-yl |
| 1025 | 1-(4-NO$_2$—C$_6$H$_4$)pyrrol-3-yl |
| 1026 | 1-(3-NO$_2$—C$_6$H$_4$)pyrrol-3-yl |
| 1027 | 1-(4-CN—C$_6$H$_4$)pyrrol-3-yl |
| 1028 | 1-(3-CN—C$_6$H$_4$)pyrrol-3-yl |
| 1029 | 1-(3-CF$_3$—C$_6$H$_4$)pyrrol-3-yl |
| 1030 | 1-(4-CF$_3$—C$_6$H$_4$)pyrrol-3-yl |
| 1031 | 1-(4-C(CH$_3$)$_3$—C$_6$H$_4$)pyrrol-3-yl |
| 1032 | 1-(2-Cl—C$_6$H$_4$)pyrrol-3-yl |
| 1033 | 1-(3-Cl—C$_6$H$_4$)pyrrol-3-yl |
| 1034 | 1-(4-Cl—C$_6$H$_4$)pyrrol-3-yl |
| 1035 | 1-(2-Br—C$_6$H$_4$)pyrrol-3-yl |
| 1036 | 1-(3-Br—C$_6$H$_4$)pyrrol-3-yl |
| 1037 | 1-(4-Br—C$_6$H$_4$)pyrrol-3-yl |
| 1038 | 1-(2-F—C$_6$H$_4$)pyrrol-3-yl |

TABLE A-continued

| No. | R⁴ |
|---|---|
| 1039 | 1-(3-F—C₆H₄)pyrrol-3-yl |
| 1040 | 1-(4-F—C₆H₄)pyrrol-3-yl |
| 1041 | 1-(2,4-Cl₂—C₆H₃)pyrrol-3-yl |
| 1042 | 1-(2,5-Cl₂—C₆H₃)pyrrol-3-yl |
| 1043 | 1-(2,6-Cl₂—C₆H₃)pyrrol-3-yl |
| 1044 | 1-(3,4-Cl₂—C₆H₃)pyrrol-3-yl |
| 1045 | 1-(2,4-F₂—C₆H₃)pyrrol-3-yl |
| 1046 | 1-(2,5-F₂—C₆H₃)pyrrol-3-yl |
| 1047 | 1-(2,6-F₂—C₆H₃)pyrrol-3-yl |
| 1048 | 1-(3,4-F₂—C₆H₃)pyrrol-3-yl |
| 1049 | 1-(2-Cl, 5-OCH₃—C₆H₃)pyrrol-3-yl |
| 1050 | 1-(2-Cl, 5-CH₃—C₆H₃)pyrrol-3-yl |
| 1051 | 1-(5-Cl, 2-OCH₃—C₆H₃)pyrrol-3-yl |
| 1052 | 1-(5-Cl, 2-CH₃—C₆H₃)pyrrol-3-yl |
| 1053 | 1-[2,5-(CH₃)₂—C₆H₃]pyrrol-3-yl |
| 1054 | 1-CH(CH₃)₂-pyrrol-2-yl |
| 1055 | 1-C(CH₃)₃-pyrrol-2-yl |
| 1056 | 1-cyclopropylpyrrol-2-yl |
| 1057 | 1-C₆H₅-pyrrol-2-yl |
| 1058 | 1-(2-CH₃—C₆H₄)pyrrol-2-yl |
| 1059 | 1-(3-CH₃—C₆H₄)pyrrol-2-yl |
| 1060 | 1-(4-CH₃—C₆H₄)pyrrol-2-yl |
| 1061 | 1-(3-OCH₃—C₆H₄)pyrrol-2-yl |
| 1062 | 1-(4-OCH₃—C₆H₄)pyrrol-2-yl |
| 1063 | 1-(4-NO₂—C₆H₄)pyrrol-2-yl |
| 1064 | 1-(3-NO₂—C₆H₄)pyrrol-2-yl |
| 1065 | 1-(4-CN—C₆H₄)pyrrol-2-yl |
| 1066 | 1-(3-CN—C₆H₄)pyrrol-2-yl |
| 1067 | 1-(3-CF₃—C₆H₄)pyrrol-2-yl |
| 1068 | 1-(4-CF₃—C₆H₄)pyrrol-2-yl |
| 1069 | 1-(4-C(CH₃)₃—C₆H₄)pyrrol-2-yl |
| 1070 | 1-(2-Cl—C₆H₄)pyrrol-2-yl |
| 1071 | 1-(3-Cl—C₆H₄)pyrrol-2-yl |
| 1072 | 1-(4-Cl—C₆H₄)pyrrol-2-yl |
| 1073 | 1-(2-Br—C₆H₄)pyrrol-2-yl |
| 1074 | 1-(3-Br—C₆H₄)pyrrol-2-yl |
| 1075 | 1-(4-Br—C₆H₄)pyrrol-2-yl |
| 1076 | 1-(2-F—C₆H₄)pyrrol-2-yl |
| 1077 | 1-(3-F—C₆H₄)pyrrol-2-yl |
| 1078 | 1-(4-F—C₆H₄)pyrrol-2-yl |
| 1079 | 1-(2,4-Cl₂—C₆H₃)pyrrol-2-yl |
| 1080 | 1-(2,5-Cl₂—C₆H₃)pyrrol-2-yl |
| 1081 | 1-(2,6-Cl₂—C₆H₃)pyrrol-2-yl |
| 1082 | 1-(3,4-Cl₂—C₆H₃)pyrrol-2-yl |
| 1083 | 1-(2,4-F₂—C₆H₃)pyrrol-2-yl |
| 1084 | 1-(2,5-F₂—C₆H₃)pyrrol-2-yl |
| 1085 | 1-(2,6-F₂—C₆H₃)pyrrol-2-yl |
| 1086 | 1-(3,4-F₂—C₆H₃)pyrrol-2-yl |
| 1087 | 1-(2-Cl, 5-OCH₃—C₆H₃)pyrrol-2-yl |
| 1088 | 1-(2-Cl, 5-CH₃—C₆H₃)pyrrol-2-yl |
| 1089 | 1-(5-Cl, 2-OCH₃—C₆H₃)pyrrol-2-yl |
| 1090 | 1-(5-Cl, 2-CH₃—C₆H₃)pyrrol-2-yl |
| 1091 | 1-[2,5-(CH₃)₂—C₆H₃]pyrrol-2-yl |
| 1092 | 5-CH(CH₃)₂-furan-2-yl |
| 1093 | 5-C(CH₃)₃-furan-2-yl |
| 1094 | 5-cyclopropylfuran-2-yl |
| 1095 | 5-C₆H₅-furan-2-yl |
| 1096 | 5-(2-CH₃—C₆H₄)furan-2-yl |
| 1097 | 5-(3-CH₃—C₆H₄)furan-2-yl |
| 1098 | 5-(4-CH₃—C₆H₄)furan-2-yl |
| 1099 | 5-(3-OCH₃—C₆H₄)furan-2-yl |
| 1100 | 5-(4-OCH₃—C₆H₄)furan-2-yl |
| 1101 | 5-(4-NO₂—C₆H₄)furan-2-yl |
| 1102 | 5-(3-NO₂—C₆H₄)furan-2-yl |
| 1103 | 5-(4-CN—C₆H₄)furan-2-yl |
| 1104 | 5-(3-CN—C₆H₄)furan-2-yl |
| 1105 | 5-(3-CF₃—C₆H₄)furan-2-yl |
| 1106 | 5-(4-CF₃—C₆H₄)furan-2-yl |
| 1107 | 5-(4-C(CH₃)₃—C₆H₄)furan-2-yl |
| 1108 | 5-(4-C₆H₅—C₆H₄)furan-2-yl |
| 1109 | 5-(2-Cl—C₆H₄)furan-2-yl |
| 1110 | 5-(3-Cl—C₆H₄)furan-2-yl |
| 1111 | 5-(4-Cl—C₆H₄)furan-2-yl |
| 1112 | 5-(2-Br—C₆H₄)furan-2-yl |
| 1113 | 5-(3-Br—C₆H₄)furan-2-yl |
| 1114 | 5-(4-Br—C₆H₄)furan-2-yl |
| 1115 | 5-(2-F—C₆H₄)furan-2-yl |
| 1116 | 5-(3-F—C₆H₄)furan-2-yl |
| 1117 | 5-(4-F—C₆H₄)furan-2-yl |
| 1118 | 5-(2,4-Cl₂—C₆H₃)furan-2-yl |
| 1119 | 5-(2,5-Cl₂—C₆H₃)furan-2-yl |
| 1120 | 5-(2,6-Cl₂—C₆H₃)furan-2-yl |
| 1121 | 5-(3,4-Cl₂—C₆H₃)furan-2-yl |
| 1122 | 5-(2,4-F₂—C₆H₃)furan-2-yl |
| 1123 | 5-(2,5-F₂—C₆H₃)furan-2-yl |
| 1124 | 5-(2,6-F₂—C₆H₃)furan-2-yl |
| 1125 | 5-(3,4-F₂—C₆H₃)furan-2-yl |
| 1126 | 5-(2-Cl, 5-OCH₃—C₆H₃)furan-2-yl |
| 1127 | 5-(2-Cl, 5-CH₃—C₆H₃)furan-2-yl |
| 1128 | 5-(5-Cl, 2-OCH₃—C₆H₃)furan-2-yl |
| 1129 | 5-(5-Cl, 2-CH₃—C₆H₃)furan-2-yl |
| 1130 | 5-[2,5-(CH₃)₂—C₆H₃]furan-2-yl |
| 1131 | 4-CH(CH₃)₂-furan-2-yl |
| 1132 | 4-C(CH₃)₃-furan-2-yl |
| 1133 | 4-cyclopropylfuran-2-yl |
| 1134 | 4-C₆H₅-furan-2-yl |
| 1135 | 4-(2-CH₃—C₆H₄)furan-2-yl |
| 1136 | 4-(3-CH₃—C₆H₄)furan-2-yl |
| 1137 | 4-(4-CH₃—C₆H₄)furan-2-yl |
| 1138 | 4-(3-OCH₃—C₆H₄)furan-2-yl |
| 1139 | 4-(4-OCH₃—C₆H₄)furan-2-yl |
| 1140 | 4-(4-NO₂—C₆H₄)furan-2-yl |
| 1141 | 4-(3-NO₂—C₆H₄)furan-2-yl |
| 1142 | 4-(4-CN—C₆H₄)furan-2-yl |
| 1143 | 4-(3-CN—C₆H₄)furan-2-yl |
| 1144 | 4-(3-CF₃—C₆H₄)furan-2-yl |
| 1145 | 4-(4-CF₃—C₆H₄)furan-2-yl |
| 1146 | 4-(4-C(CH₃)₃—C₆H₄)furan-2-yl |
| 1147 | 4-(2-Cl—C₆H₄)furan-2-yl |
| 1148 | 4-(3-Cl—C₆H₄)furan-2-yl |
| 1149 | 4-(4-Cl—C₆H₄)furan-2-yl |
| 1150 | 4-(2-Br—C₆H₄)furan-2-yl |
| 1151 | 4-(3-Br—C₆H₄)furan-2-yl |
| 1152 | 4-(4-Br—C₆H₄)furan-2-yl |
| 1153 | 4-(2-F-C₆H₄)furan-2-yl |
| 1154 | 4-(3-F-C₆H₄)furan-2-yl |
| 1155 | 4-(4-F-C₆H₄)furan-2-yl |
| 1156 | 4-(2,4-Cl₂—C₆H₃)furan-2-yl |
| 1157 | 4-(2,5-Cl₂—C₆H₃)furan-2-yl |
| 1158 | 4-(2,6-Cl₂—C₆H₃)furan-2-yl |
| 1159 | 4-(3,4-Cl₂—C₆H₃)furan-2-yl |
| 1160 | 4-(2,4-F₂—C₆H₃)furan-2-yl |
| 1161 | 4-(2,5-F₂—C₆H₃)furan-2-yl |
| 1162 | 4-(2,6-F₂—C₆H₃)furan-2-yl |
| 1163 | 4-(3,4-F₂—C₆H₃)furan-2-yl |
| 1164 | 4-(2-Cl, 5-OCH₃—C₆H₃)furan-2-yl |
| 1165 | 4-(2-Cl, 5-CH₃—C₆H₃)furan-2-yl |
| 1166 | 4-(5-Cl, 2-OCH₃—C₆H₃)furan-2-yl |
| 1167 | 4-(5-Cl, 2-CH₃—C₆H₃)furan-2-yl |
| 1168 | 4-[2,5-(CH₃)₂—C₆H₃]furan-2-yl |
| 1169 | 5-CH(CH₃)₂-thien-2-yl |
| 1170 | 5-C(CH₃)₃-thien-2-yl |
| 1171 | 5-cyclopropylthien-2-yl |
| 1172 | 5-C₆H₅-thien-2-yl |
| 1173 | 5-(2-CH₃—C₆H₄)thien-2-yl |
| 1174 | 5-(3-CH₃—C₆H₄)thien-2-yl |
| 1175 | 5-(4-CH₃—C₆H₄)thien-2-yl |
| 1176 | 5-(3-OCH₃—C₆H₄)thien-2-yl |
| 1177 | 5-(4-OCH₃—C₆H₄)thien-2-yl |
| 1178 | 5-(4-NO₂—C₆H₄)thien-2-yl |
| 1179 | 5-(3-NO₂—C₆H₄)thien-2-yl |
| 1180 | 5-(4-CN—C₆H₄)thien-2-yl |
| 1181 | 5-(3-CN—C₆H₄)thien-2-yl |
| 1182 | 5-(3-CF₃—C₆H₄)thien-2-yl |
| 1183 | 5-(4-CF₃—C₆H₄)thien-2-yl |
| 1184 | 5-(4-C(CH₃)₃—C₆H₄)thien-2-yl |
| 1185 | 5-(2-Cl—C₆H₄)thien-2-yl |
| 1186 | 5-(3-Cl—C₆H₄)thien-2-yl |
| 1187 | 5-(4-Cl—C₆H₄)thien-2-yl |
| 1188 | 5-(2-Br—C₆H₄)thien-2-yl |
| 1189 | 5-(3-Br—C₆H₄)thien-2-yl |
| 1190 | 5-(4-Br—C₆H₄)thien-2-yl |
| 1191 | 5-(2-F—C₆H₄)thien-2-yl |
| 1192 | 5-(3-F—C₆H₄)thien-2-yl |

TABLE A-continued

| No. | R⁴ |
|---|---|
| 1193 | 5-(4-F—C₆H₄)thien-2-yl |
| 1194 | 5-(2,4-Cl₂—C₆H₃)thien-2-yl |
| 1195 | 5-(2,5-Cl₂—C₆H₃)thien-2-yl |
| 1196 | 5-(2,6-Cl₂—C₆H₃)thien-2-yl |
| 1197 | 5-(3,4-Cl₂—C₆H₃)thien-2-yl |
| 1198 | 5-(2,4-F₂—C₆H₃)thien-2-yl |
| 1199 | 5-(2,5-F₂—C₆H₃)thien-2-yl |
| 1200 | 5-(2,6-F₂—C₆H₃)thien-2-yl |
| 1201 | 5-(3,4-F₂—C₆H₃)thien-2-yl |
| 1202 | 5-(2-Cl, 5-OCH₃—C₆H₃)thien-2-yl |
| 1203 | 5-(2-Cl, 5-CH₃—C₆H₃)thien-2-yl |
| 1204 | 5-(5-Cl, 2-OCH₃—C₆H₃)thien-2-yl |
| 1205 | 5-(5-Cl, 2-CH₃—C₆H₃)thien-2-yl |
| 1206 | 5-[2,5-(CH₃)₂—C₆H₃]thien-2-yl |
| 1207 | 4-CH(CH₃)₂-thien-2-yl |
| 1208 | 4-C(CH₃)₃-thien-2-yl |
| 1209 | 4-cyclopropylthien-2-yl |
| 1210 | 4-C₆H₅-thien-2-yl |
| 1211 | 4-(2-CH₃—C₆H₄)thien-2-yl |
| 1212 | 4-(3-CH₃—C₆H₄)thien-2-yl |
| 1213 | 4-(4-CH₃—C₆H₄)thien-2-yl |
| 1214 | 4-(3-OCH₃—C₆H₄)thien-2-yl |
| 1215 | 4-(4-OCH₃—C₆H₄)thien-2-yl |
| 1216 | 4-(4-NO₂—C₆H₄)thien-2-yl |
| 1217 | 4-(3-NO₂—C₆H₄)thien-2-yl |
| 1218 | 4-(4-CN—C₆H₄)thien-2-yl |
| 1219 | 4-(3-CN—C₆H₄)thien-2-yl |
| 1220 | 4-(3-CF₃—C₆H₄)thien-2-yl |
| 1221 | 4-(4-CF₃—C₆H₄)thien-2-yl |
| 1222 | 4-(4-C(CH₃)₃—C₆H₄)thien-2-yl |
| 1223 | 4-(2-Cl—C₆H₄)thien-2-yl |
| 1224 | 4-(3-Cl—C₆H₄)thien-2-yl |
| 1225 | 4-(4-Cl—C₆H₄)thien-2-yl |
| 1226 | 4-(2-Br—C₆H₄)thien-2-yl |
| 1227 | 4-(3-Br—C₆H₄)thien-2-yl |
| 1228 | 4-(4-Br—C₆H₄)thien-2-yl |
| 1229 | 4-(2-F—C₆H₄)thien-2-yl |
| 1230 | 4-(3-F—C₆H₄)thien-2-yl |
| 1231 | 4-(4-F—C₆H₄)thien-2-yl |
| 1232 | 4-(2,4-Cl₂—C₆H₃)thien-2-yl |
| 1233 | 4-(2,5-Cl₂—C₆H₃)thien-2-yl |
| 1234 | 4-(2,6-Cl₂—C₆H₃)thien-2-yl |
| 1235 | 4-(3,4-Cl₂—C₆H₃)thien-2-yl |
| 1236 | 4-(2,4-F₂—C₆H₃)thien-2-yl |
| 1237 | 4-(2,5-F₂—C₆H₃)thien-2-yl |
| 1238 | 4-(2,6-F₂—C₆H₃)thien-2-yl |
| 1239 | 4-(3,4-F₂—C₆H₃)thien-2-yl |
| 1240 | 4-(2-Cl, 5-OCH₃—C₆H₃)thien-2-yl |
| 1241 | 4-(2-Cl, 5-CH₃—C₆H₃)thien-2-yl |
| 1242 | 4-(5-Cl, 2-OCH₃—C₆H₃)thien-2-yl |
| 1243 | 4-(5-Cl, 2-CH₃—C₆H₃)thien-2-yl |
| 1244 | 4-[2,5-(CH₃)₂—C₆H₃]thien-2-yl |
| 1245 | 2-CH₃-thien-4-yl |
| 1246 | 2-CH(CH₃)₂-thien-4-yl |
| 1247 | 2-C(CH₃)₃-thien-4-yl |
| 1248 | 2-cyclopropylthien-4-yl |
| 1249 | 2-C₆H₅-thien-4-yl |
| 1250 | 2-(2-CH₃—C₆H₄)thien-4-yl |
| 1251 | 2-(3-CH₃—C₆H₄)thien-4-yl |
| 1252 | 2-(4-CH₃—C₆H₄)thien-4-yl |
| 1253 | 2-(3-OCH₃—C₆H₄)thien-4-yl |
| 1254 | 2-(4-OCH₃—C₆H₄)thien-4-yl |
| 1255 | 2-(4-NO₂—C₆H₄)thien-4-yl |
| 1256 | 2-(3-NO₂—C₆H₄)thien-4-yl |
| 1257 | 2-(4-CN—C₆H₄)thien-4-yl |
| 1258 | 2-(3-CN—C₆H₄)thien-4-yl |
| 1259 | 2-(3-CF₃—C₆H₄)thien-4-yl |
| 1260 | 2-(4-CF₃—C₆H₄)thien-4-yl |
| 1261 | 2-(4-C(CH₃)₃—C₆H₄)thien-4-yl |
| 1262 | 2-(2-Cl—C₆H₄)thien-4-yl |
| 1263 | 2-(3-Cl—C₆H₄)thien-4-yl |
| 1264 | 2-(4-Cl—C₆H₄)thien-4-yl |
| 1265 | 2-(2-Br—C₆H₄)thien-4-yl |
| 1266 | 2-(3-Br—C₆H₄)thien-4-yl |
| 1267 | 2-(4-Br—C₆H₄)thien-4-yl |
| 1268 | 2-(2-F—C₆H₄)thien-4-yl |
| 1269 | 2-(3-F—C₆H₄)thien-4-yl |
| 1270 | 2-(4-F—C₆H₄)thien-4-yl |
| 1271 | 2-(2,4-Cl₂—C₆H₃)thien-4-yl |
| 1272 | 2-(2,5-Cl₂—C₆H₃)thien-4-yl |
| 1273 | 2-(2,6-Cl₂—C₆H₃)thien-4-yl |
| 1274 | 2-(3,4-Cl₂—C₆H₃)thien-4-yl |
| 1275 | 2-(2,4-F₂—C₆H₃)thien-4-yl |
| 1276 | 2-(2,5-F₂—C₆H₃)thien-4-yl |
| 1277 | 2-(2,6-F₂—C₆H₃)thien-4-yl |
| 1278 | 2-(3,4-F₂—C₆H₃)thien-4-yl |
| 1279 | 2-(2-Cl, 5-OCH₃—C₆H₃)thien-4-yl |
| 1280 | 2-(2-Cl, 5-CH₃—C₆H₃)thien-4-yl |
| 1281 | 2-(5-Cl, 2-OCH₃—C₆H₃)thien-4-yl |
| 1282 | 2-(5-Cl, 2-CH₃—C₆H₃)thien-4-yl |
| 1283 | 2-[2,5-(CH₃)₂—C₆H₃]thien-4-yl |
| 1284 | 1-CH(CH₃)₂-pyrazol-4-yl |
| 1285 | 1-C(CH₃)₃-pyrazol-4-yl |
| 1286 | 1-cyclopropylpyrazol-4-yl |
| 1287 | 1-C₆H₅-pyrazol-4-yl |
| 1288 | 1-(2-CH₃—C₆H₄)pyrazol-4-yl |
| 1289 | 1-(3-CH₃—C₆H₄)pyrazol-4-yl |
| 1290 | 1-(4-CH₃—C₆H₄)pyrazol-4-yl |
| 1291 | 1-(3-OCH₃—C₆H₄)pyrazol-4-yl |
| 1292 | 1-(4-OCH₃—C₆H₄)pyrazol-4-yl |
| 1293 | 1-(4-NO₂—C₆H₄)pyrazol-4-yl |
| 1294 | 1-(3-NO₂—C₆H₄)pyrazol-4-yl |
| 1295 | 1-(4-CN—C₆H₄)pyrozol-4-yl |
| 1296 | 1-(3-CN—C₆H₄)pyrazol-4-yl |
| 1297 | 1-(3-CF₃—C₆H₄)pyrazol-4-yl |
| 1298 | 1-(4-CF₃—C₆H₄)pyrazol-4-yl |
| 1299 | 1-(4-C(CH₃)₃—C₆H₄)pyrazol-4-yl |
| 1300 | 1-(2-Cl—C₆H₄)pyrazol-4-yl |
| 1301 | 1-(3-Cl—C₆H₄)pyrazol-4-yl |
| 1302 | 1-(4-Cl—C₆H₄)pyrazol-4-yl |
| 1303 | 1-(2-Br—C₆H₄)pyrazol-4-yl |
| 1304 | 1-(3-Br—C₆H₄)pyrazol-4-yl |
| 1305 | 1-(4-Br—C₆H₄)pyrazol-4-yl |
| 1306 | 1-(2-F—C₆H₄)pyrazol-4-yl |
| 1307 | 1-(3-F—C₆H₄)pyrazol-4-yl |
| 1308 | 1-(4-F—C₆H₄)pyrazol-4-yl |
| 1309 | 1-(2,4-Cl₂—C₆H₃)pyrazol-4-yl |
| 1310 | 1-(2,5-Cl₂—C₆H₃)pyrazol-4-yl |
| 1311 | 1-(2,6-Cl₂—C₆H₃)pyrazol-4-yl |
| 1312 | 1-(3,4-Cl₂—C₆H₃)pyrazol-4-yl |
| 1313 | 1-(2,4-F₂—C₆H₃)pyrazol-4-yl |
| 1314 | 1-(2,5-F₂—C₆H₃)pyrazol-4-yl |
| 1315 | 1-(2,6-F₂—C₆H₃)pyrazol-4-yl |
| 1316 | 1-(3,4-F₂—C₆H₃)pyrazol-4-yl |
| 1317 | 1-Cl, 5-OCH₃—C₆H₃)pyrazol-4-yl |
| 1318 | 1-(2-Cl, 5-CH₃—C₆H₃)pyrazol-4-yl |
| 1319 | 1-(5-Cl, 2-OCH₃—C₆H₃)pyrazol-4-yl |
| 1320 | 1-(5-Cl, 2-CH₃—C₆H₃)pyrazol-4-yl |
| 1321 | 1-[2,5-(CH₃)₂—C₆H₃]pyrazol-4-yl |
| 1322 | 1-CH(CH₃)₂-pyrazol-3-yl |
| 1323 | 1-C(CH₃)₃-pyrazol-3-yl |
| 1324 | 1-cyclopropylpyrazol-3-yl |
| 1325 | 1-C₆H₅-pyrazol-3-yl |
| 1326 | 1-(2-CH₃—C₆H₄)pyrazol-3-yl |
| 1327 | 1-(3-CH₃—C₆H₄)pyrazol-3-yl |
| 1328 | 1-(4-CH₃—C₆H₄)pyrazol-3-yl |
| 1329 | 1-(3-OCH₃—C₆H₄)pyrazol-3-yl |
| 1330 | 1-(4-OCH₃—C₆H₄)pyrazol-3-yl |
| 1331 | 1-(4-NO₂—C₆H₄)pyrazol-3-yl |
| 1332 | 1-(3-NO₂—C₆H₄)pyrazol-3-yl |
| 1333 | 1-(4-CN—C₆H₄)pyrazol-3-yl |
| 1334 | 1-(3-CN—C₆H₄)pyrazol-3-yl |
| 1335 | 1-(3-CF₃—C₆H₄)pyrazol-3-yl |
| 1336 | 1-(4-CF₃—C₆H₄)pyrazol-3-yl |
| 1337 | 1-(4-C(CH₃)₃—C₆H₄)pyrazol-3-yl |
| 1338 | 1-(2-Cl—C₆H₄)pyrazol-3-yl |
| 1339 | 1-(3-Cl—C₆H₄)pyrazol-3-yl |
| 1340 | 1-(4-Cl—C₆H₄)pyrazol-3-yl |
| 1341 | 1-(2-Br—C₆H₄)pyrazol-3-yl |
| 1342 | 1-(3-Br—C₆H₄)pyrazol-3-yl |
| 1343 | 1-(4-Br—C₆H₄)pyrazol-3-yl |
| 1344 | 1-(2-F—C₆H₄)pyrazol-3-yl |
| 1345 | 1-(3-F—C₆H₄)pyrazol-3-yl |
| 1346 | 1-(4-F—C₆H₄)pyrazol-3-yl |

TABLE A-continued

| No. | R⁴ |
|---|---|
| 1347 | 1-(2,4-Cl₂—C₆H₃)pyrazol-3-yl |
| 1348 | 1-(2,5-Cl₂—C₆H₃)pyrazol-3-yl |
| 1349 | 1-(2,6-Cl₂—C₆H₃)pyrazol-3-yl |
| 1350 | 1-(3,4-Cl₂—C₆H₃)pyrazol-3-yl |
| 1351 | 1-(2,4-F₂—C₆H₃)pyrazol-3-yl |
| 1352 | 1-(2,5-F₂—C₆H₃)pyrazol-3-yl |
| 1353 | 1-(2,6-F₂—C₆H₃)pyrazol-3-yl |
| 1354 | 1-(3,4-F₂—C₆H₃)pyrazol-3-yl |
| 1355 | 1-(2-Cl, 5-OCH₃—C₆H₃)pyrazol-3-yl |
| 1356 | 1-(2-Cl, 5-CH₃—C₆H₃)pyrazol-3-yl |
| 1357 | 1-(5-Cl, 2-OCH₃—C₆H₃)pyrazol-3-yl |
| 1358 | 1-(5-Cl, 2-CH₃—C₆H₃)pyrazol-3-yl |
| 1359 | 1-[2,5-(CH₃)₂—C₆H₃]pyrazol-3-yl |
| 1360 | 3-CH(CH₃)₂-isoxazol-5-yl |
| 1361 | 3-C(CH₃)₃-isoxazol-5-yl |
| 1362 | 3-cyclopropylisoxazol-5-yl |
| 1363 | 3-C₆H₅-isoxazol-5-yl |
| 1364 | 3-(2-CH₃—C₆H₄)isoxazol-5-yl |
| 1365 | 3-(3-CH₃—C₆H₄)isoxazol-5-yl |
| 1366 | 3-(4-CH₃—C₆H₄)isoxazol-5-yl |
| 1367 | 3-(3-OCH₃—C₆H₄)isoxazol-5-yl |
| 1368 | 3-(4-OCH₃—C₆H₄)isoxazol-5-yl |
| 1369 | 3-(4-NO₂—C₆H₄)isoxazol-5-yl |
| 1370 | 3-(3-NO₂—C₆H₄)isoxazol-5-yl |
| 1371 | 3-(4-CN—C₆H₄)isoxazol-5-yl |
| 1372 | 3-(3-CN—C₆H₄)isoxazol-5-yl |
| 1373 | 3-(3-CF₃—C₆H₄)isoxazol-5-yl |
| 1374 | 3-(4-CF₃—C₆H₄)isoxazol-5-yl |
| 1375 | 3-(4-C(CH₃)₃—C₆H₄)isoxazol-5-yl |
| 1376 | 3-(2-Cl—C₆H₄)isoxazol-5-yl |
| 1377 | 3-(3-Cl—C₆H₄)isoxazol-5-yl |
| 1378 | 3-(4-Cl—C₆H₄)isoxazol-5-yl |
| 1379 | 3-(2-Br—C₆H₄)isoxazol-5-yl |
| 1380 | 3-(3-Br—C₆H₄)isoxazol-5-yl |
| 1381 | 3-(4-Br—C₆H₄)isoxazol-5-yl |
| 1382 | 3-(2-F—C₆H₄)isoxazol-5-yl |
| 1383 | 3-(3-F—C₆H₄)isoxazol-5-yl |
| 1384 | 3-(4-F—C₆H₄)isoxazol-5-yl |
| 1385 | 3-(2,4-Cl₂—C₆H₃)isoxazol-5-yl |
| 1386 | 3-(2,5-Cl₂—C₆H₃)isoxazol-5-yl |
| 1387 | 3-(2,6-Cl₂—C₆H₃)isoxazol-5-yl |
| 1388 | 3-(3,4-Cl₂—C₆H₃)isoxazol-5-yl |
| 1389 | 3-(2,4-F₂—C₆H₃)isoxazol-5-yl |
| 1390 | 3-(2,5-F₂—C₆H₃)isoxazol-5-yl |
| 1391 | 3-(2,6-F₂—C₆H₃)isoxazol-5-yl |
| 1392 | 3-(3,4-F₂—C₆H₃)isoxazol-5-yl |
| 1393 | 3-(2-Cl, 5-OCH₃—C₆H₃)isoxazol-5-yl |
| 1394 | 3-(2-Cl, 5-CH₃—C₆H₃)isoxazol-5-yl |
| 1395 | 3-(5-Cl, 2-OCH₃—C₆H₃)isoxazol-5-yl |
| 1396 | 3-(5-Cl, 2-CH₃—C₆H₃)isoxazol-5-yl |
| 1397 | 3-[2,5-(CH₃)₂—C₆H₃]isoxazol-5-yl |
| 1398 | 5-CH(CH₃)₂-isoxazol-3-yl |
| 1399 | 5-C(CH₃)₃-isoxazol-3-yl |
| 1400 | 5-cyclopropylisoxazol-3-yl |
| 1401 | 5-C₆H₅-isoxazol-3-yl |
| 1402 | 5-(2-CH₃—C₆H₄)isoxazol-3-yl |
| 1403 | 5-(3-CH₃—C₆H₄)isoxazol-3-yl |
| 1404 | 5-(4-CH₃—C₆H₄)isoxazol-3-yl |
| 1405 | 5-(3-OCH₃—C₆H₄)isoxazol-3-yl |
| 1406 | 5-(4-OCH₃—C₆H₄)isoxazol-3-yl |
| 1407 | 5-(4-NO₂—C₆H₄)isoxazol-3-yl |
| 1408 | 5-(3-NO₂—C₆H₄)isoxazol-3-yl |
| 1409 | 5-(4-CN—C₆H₄)isoxazol-3-yl |
| 1410 | 5-(3-CN—C₆H₄)isoxazol-3-yl |
| 1411 | 5-(3-CF₃—C₆H₄)isoxazol-3-yl |
| 1412 | 5-(4-CF₃—C₆H₄)isoxazol-3-yl |
| 1413 | 5-(4-C(CH₃)₃—C₆H₄)isoxazol-3-yl |
| 1414 | 5-(2-Cl—C₆H₄)isoxazol-3-yl |
| 1415 | 5-(3-Cl—C₆H₄)isoxazol-3-yl |
| 1416 | 5-(4-Cl—C₆H₄)isoxazol-3-yl |
| 1417 | 5-(2-Br—C₆H₄)isoxazol-3-yl |
| 1418 | 5-(3-Br—C₆H₄)isoxazol-3-yl |
| 1419 | 5-(4-Br—C₆H₄)isoxazol-3-yl |
| 1420 | 5-(2-F—C₆H₄)isoxazol-3-yl |
| 1421 | 5-(3-F—C₆H₄)isoxazol-3-yl |
| 1422 | 5-(4-F—C₆H₄)isoxazol-3-yl |
| 1423 | 5-(2,4-Cl₂—C₆H₃)isoxazol-3-yl |
| 1424 | 5-(2,5-Cl₂—C₆H₃)isoxazol-3-yl |
| 1425 | 5-(2,6-Cl₂—C₆H₃)isoxazol-3-yl |
| 1426 | 5-(3,4-Cl₂—C₆H₃)isoxazol-3-yl |
| 1427 | 5-(2,4-F₂—C₆H₃)isoxazol-3-yl |
| 1428 | 5-(2,5-F₂—C₆H₃)isoxazol-3-yl |
| 1429 | 5-(2,6-F₂—C₆H₃)isoxazol-3-yl |
| 1430 | 5-(3,4-F₂—C₆H₃)isoxazol-3-yl |
| 1431 | 5-(2-Cl, 5-OCH₃—C₆H₃)isoxazol-3-yl |
| 1432 | 5-(2-Cl, 5-CH₃—C₆H₃)isoxazol-3-yl |
| 1433 | 5-(5-Cl, 2-OCH₃—C₆H₃)isoxazol-3-yl |
| 1434 | 5-(5-Cl, 2-CH₃—C₆H₃)isoxazol-3-yl |
| 1435 | 5-[2,5-(CH₃)₂—C₆H₃]isoxazol-3-yl |
| 1436 | 3-CH(CH₃)₂-isothiazol-5-yl |
| 1437 | 3-C(CH₃)₃-isothiazol-5-yl |
| 1438 | 3-cyclopropylisothiazol-5-yl |
| 1439 | 3-C₆H₅-isothiazol-5-yl |
| 1440 | 3-(2-CH₃—C₆H₄)isothiazol-5-yl |
| 1441 | 3-(3-CH₃—C₆H₄)isothiazol-5-yl |
| 1442 | 3-(4-CH₃—C₆H₄)isothiazol-5-yl |
| 1443 | 3-(3-OCH₃—C₆H₄)isothiazol-5-yl |
| 1444 | 3-(4-OCH₃—C₆H₄)isothiazol-5-yl |
| 1445 | 3-(4-NO₂—C₆H₄)isothiazol-5-yl |
| 1446 | 3-(3-NO₂—C₆H₄)isothiazol-5-yl |
| 1447 | 3-(4-CN—C₆H₄)isothiazol-5-yl |
| 1448 | 3-(3-CN—C₆H₄)isothiazol-5-yl |
| 1449 | 3-(3-CF₃—C₆H₄)isothiazol-5-yl |
| 1450 | 3-(4-CF₃—C₆H₄)isothiazol-5-yl |
| 1451 | 3-(4-C(CH₃)₃—C₆H₄)isothiazol-5-yl |
| 1452 | 3-(2-Cl—C₆H₄)isothiazol-5-yl |
| 1453 | 3-(3-Cl—C₆H₄)isothiazol-5-yl |
| 1454 | 3-(4-Cl—C₆H₄)isothiazol-5-yl |
| 1455 | 3-(2-Br—C₆H₄)isothiazol-5-yl |
| 1456 | 3-(3-Br—C₆H₄)isothiazol-5-yl |
| 1457 | 3-(4-Br—C₆H₄)isothiazol-5-yl |
| 1458 | 3-(2-F—C₆H₄)isothiazol-5-yl |
| 1459 | 3-(3-F—C₆H₄)isothiazol-5-yl |
| 1460 | 3-(4-F—C₆H₄)isothiazol-5-yl |
| 1461 | 3-(2,4-Cl₂—C₆H₃)isothiazol-5-yl |
| 1462 | 3-(2,5-Cl₂—C₆H₃)isothiazol-5-yl |
| 1463 | 3-(2,6-Cl₂—C₆H₃)isothiazol-5-yl |
| 1464 | 3-(3,4-Cl₂—C₆H₃)isothiazol-5-yl |
| 1465 | 3-(2,4-F₂—C₆H₃)isothiazol-5-yl |
| 1466 | 3-(2,5-F₂—C₆H₃)isothiazol-5-yl |
| 1467 | 3-(2,6-F₂—C₆H₃)isothiazol-5-yl |
| 1468 | 3-(3,4-F₂—C₆H₃)isothiazol-5-yl |
| 1469 | 3-(2-Cl, 5-OCH₃—C₆H₃)isothiazol-5-yl |
| 1470 | 3-(2-Cl, 5-CH₃—C₆H₃)isothiazol-5-yl |
| 1471 | 3-(5-Cl, 2-OCH₃—C₆H₃)isothiazol-5-yl |
| 1472 | 3-(5-Cl, 2-CH₃—C₆H₃)isothiazol-5-yl |
| 1473 | 3-[2,5-(CH₃)₂—C₆H₃]isothiazol-5-yl |
| 1474 | 2-CH(CH₃)₂-oxazol-4-yl |
| 1475 | 2-C(CH₃)₃-oxazol-4-yl |
| 1476 | 2-cyclopropyloxazol-4-yl |
| 1477 | 2-C₆H₅-oxazol-4-yl |
| 1478 | 2-(2-CH₃—C₆H₄)oxazol-4-yl |
| 1479 | 2-(3-CH₃—C₆H₄)oxazol-4-yl |
| 1480 | 2-(4-CH₃—C₆H₄)oxazol-4-yl |
| 1481 | 2-(3-OCH₃—C₆H₄)oxazol-4-yl |
| 1482 | 2-(4-OCH₃—C₆H₄)oxazol-4-yl |
| 1483 | 2-(4-NO₂—C₆H₄)oxazol-4-yl |
| 1484 | 2-(3-NO₂—C₆H₄)oxazol-4-yl |
| 1485 | 2-(4-CN—C₆H₄)oxazol-4-yl |
| 1486 | 2-(3-CN—C₆H₄)oxazol-4-yl |
| 1487 | 2-(3-CF₃—C₆H₄)oxazol-4-yl |
| 1488 | 2-(4-CF₃—C₆H₄)oxazol-4-yl |
| 1489 | 2-(4-C(CH₃)₃—C₆H₄)oxazol-4-yl |
| 1490 | 2-(2-Cl—C₆H₄)oxazol-4-yl |
| 1491 | 2-(3-Cl—C₆H₄)oxazol-4-yl |
| 1492 | 2-(4-Cl—C₆H₄)oxazol-4-yl |
| 1493 | 2-(2-Br—C₆H₄)oxazol-4-yl |
| 1494 | 2-(3-Br—C₆H₄)oxazol-4-yl |
| 1495 | 2-(4-Br—C₆H₄)oxazol-4-yl |
| 1496 | 2-(2-F—C₆H₄)oxazol-4-yl |
| 1497 | 2-(3-F—C₆H₄)oxazol-4-yl |
| 1498 | 2-(4-F—C₆H₄)oxazol-4-yl |
| 1499 | 2-(2,4-Cl₂—C₆H₃)oxazol-4-yl |
| 1500 | 2-(2,5-Cl₂—C₆H₃)oxazol-4-yl |

TABLE A-continued

| No. | R⁴ |
|---|---|
| 1501 | 2-(2,6-Cl₂—C₆H₃)oxazol-4-yl |
| 1502 | 2-(3,4-Cl₂—C₆H₃)oxazol-4-yl |
| 1503 | 2-(2,4-F₂—C₆H₃)oxazol-4-yl |
| 1504 | 2-(2,5-F₂—C₆H₃)oxazol-4-yl |
| 1505 | 2-(2,6-F₂—C₆H₃)oxazol-4-yl |
| 1506 | 2-(3,4-F₂—C₆H₃)oxazol-4-yl |
| 1507 | 2-(2-Cl, 5-OCH₃—C₆H₃)oxazol-4-yl |
| 1508 | 1-(2-Cl, 5-CH₃—C₆H₃)oxazol-4-yl |
| 1509 | 1-(5-Cl, 2-OCH₃—C₆H₃)oxazol-4-yl |
| 1510 | 2-(5-Cl, 2-CH₃₁—C₆H₃)oxazol-4-yl |
| 1511 | 2-[2,5-(CH₃)₂—C₆H₃]oxazol-4-yl |
| 1512 | 2-CH(CH₃₁)₂-thiazol-4-yl |
| 1513 | 2-C(CH₃)₃-thiazol-4-yl |
| 1514 | 2-cyclopropylthiazol-4-yl |
| 1515 | 2-C₆H₅-thiazol-4-yl |
| 1516 | 2-(2-CH₃—C₆H₄)thiazol-4-yl |
| 1517 | 2-(3-CH₃—C₆H₄)thiazol-4-yl |
| 1518 | 2-(4-CH₃—C₆H₄)thiazol-4-yl |
| 1519 | 2-(3-OCH₃—C₆H₄)thiazol-4-yl |
| 1520 | 2-(4-OCH₃—C₆H₄)thiazol-4-yl |
| 1521 | 2-(4-NO₂—C₆H₄)thiazol-4-yl |
| 1522 | 2-(3-NO₂—C₆H₄)thiazol-4-yl |
| 1523 | 2-(4-CN—C₆H₄)thiazol-4-yl |
| 1524 | 2-(3-CN—C₆H₄)thiazol-4-yl |
| 1525 | 2-(3-CF₃—C₆H₄)thiazol-4-yl |
| 1526 | 2-(4-CF₃—C₆H₄)thiazol-4-yl |
| 1527 | 2-(4-C(CH₃)₃—C₆H₄)thiazol-4-yl |
| 1528 | 2-(2-Cl—C₆H₄)thiazol-4-yl |
| 1529 | 2-(3-Cl—C₆H₄)thiazol-4-yl |
| 1530 | 2-(4-Cl—C₆H₄)thiazol-4-yl |
| 1531 | 2-(2-Br—C₆H₄)thiazol-4-yl |
| 1532 | 2-(3-Br—C₆H₄)thiazol-4-yl |
| 1533 | 2-(4-Br—C₆H₄)thiazol-4-yl |
| 1534 | 2-(2-F—C₆H₄)thiazol-4-yl |
| 1535 | 2-(3-F—C₆H₄)thiazol-4-yl |
| 1536 | 2-(4-F—C₆H₄)thiazol-4-yl |
| 1537 | 2-(2,4-Cl₂—C₆H₃)thiazol-4-yl |
| 1538 | 2-(2,5-Cl₂—C₆H₃)thiazol-4-yl |
| 1539 | 2-(2,6-Cl₂—C₆H₃)thiazol-4-yl |
| 1540 | 2-(3,4-Cl₂—C₆H₃)thiazol-4-yl |
| 1541 | 2-(2,4-F₂—C₆H₃)thiazol-4-yl |
| 1542 | 2-(2,5-F₂—C₆H₃)thiazol-4-yl |
| 1543 | 2-(2,6-F₂—C₆H₃)thiazol-4-yl |
| 1544 | 2-(3,4-F₂—C₆H₃)thiazol-4-yl |
| 1545 | 2-(2-Cl, 5-OCH₃—C₆H₃)thiazol-4-yl |
| 1546 | 2-(2-Cl, 5-CH₃—C₆H₃)thiazol-4-yl |
| 1547 | 2-(5-Cl, 2-OCH₃—C₆H₃)thiazol-4-yl |
| 1548 | 2-(5-Cl, 2-CH₃—C₆H₃)thiazol-4-yl |
| 1549 | 2-[2,5-(CH₃)₂—C₆H₃]thiazol-4-yl |
| 1550 | 1,3-(CH₃)₂-1,2,4-triazol-5-yl |
| 1551 | 1-CH(CH₃)₂-1,2,4-triazol-3-yl |
| 1552 | 1-C(CH₃)₃-1,2,4-triazol-3-yl |
| 1553 | 1-cyclopropyl-1,2,4-triazol-3-yl |
| 1554 | 1-C₆H₅-1,2,4-triazol-3-yl |
| 1555 | 1-(2-CH₃—C₆H₄)-1,2,4-triazol-3-yl |
| 1556 | 1-(3-CH₃—C₆H₄)-1,2,4-triazol-3-yl |
| 1557 | 1-(4-CH₃—C₆H₄)-1,2,4-triazol-3-yl |
| 1558 | 1-(3-OCH₃—C₆H₄)-1,2,4-triazol-3-yl |
| 1559 | 1-(4-OCH₃—C₆H₄)-1,2,4-triazol-3-yl |
| 1560 | 1-(4-NO₂—C₆H₄)-1,2,4-triazol-3-yl |
| 1561 | 1-(3-NO₂—C₆H₄)-1,2,4-triazol-3-yl |
| 1562 | 1-(4-CN—C₆H₄)-1,2,4-triazol-3-yl |
| 1563 | 1-(3-CN—C₆H₄)-1,2,4-triazol-3-yl |
| 1564 | 1-(3-CF₃—C₆H₄)-1,2,4-triazol-3-yl |
| 1565 | 1-(4-CF₃—C₆H₄)-1,2,4-triazol-3-yl |
| 1566 | 1-(4-C(CH₃)₃—C₆H₄)-1,2,4-triazol-3-yl |
| 1567 | 1-(4-C₆H₅—C₆H₄)-1,2,4-triazol-3-yl |
| 1568 | 1-(2-Cl—C₆H₄)-1,2,4-triazol-3-yl |
| 1569 | 1-(3-Cl—C₆H₄)-1,2,4-triazol-3-yl |
| 1570 | 1-(4-Cl—C₆H₄)-1,2,4-triazol-3-yl |
| 1571 | 1-(2-Br—C₆H₄)-1,2,4-triazol-3-yl |
| 1572 | 1-(3-Br—C₆H₄)-1,2,4-triazol-3-yl |
| 1573 | 1-(4-Br—C₆H₄)-1,2,4-triazol-3-yl |
| 1574 | 1-(2-F—C₆H₄)-1,2,4-triazol-3-yl |
| 1575 | 1-(3-F—C₆H₄)-1,2,4-triazol-3-yl |
| 1576 | 1-(4-F—C₆H₄)-1,2,4-triazol-3-yl |
| 1577 | 1-(2,4-Cl₂—C₆H₃)-1,2,4-triazol-3-yl |
| 1578 | 1-(2,5-Cl₂—C₆H₃)-1,2,4-triazol-3-yl |
| 1579 | 1-(2,6-Cl₂—C₆H₃)-1,2,4-triazol-3-yl |
| 1580 | 1-(3,4-Cl₂—C₆H₃)-1,2,4-triazol-3-yl |
| 1581 | 1-(2,4-F₂—C₆H₃)-1,2,4-triazol-3-yl |
| 1582 | 1-(2,5-F₂—C₆H₃)-1,2,4-triazol-3-yl |
| 1583 | 1-(2,6-F₂—C₆H₃)-1,2,4-triazol-3-yl |
| 1584 | 1-(3,4-F₂—C₆H₃)-1,2,4-triazol-3-yl |
| 1585 | 1-(2-Cl, 5-OCH₃C₆H₃)-1,2,4-triazol-3-yl |
| 1586 | 1-(2-Cl, 5-CH₃—C₆H₃)-1,2,4-triazol-3-yl |
| 1587 | 1-(5-Cl, 2-OCH₃—C₆H₃)-1,2,4-triazol-3-yl |
| 1588 | 1-(5-Cl, 2-CH₃—C₆H₃)-1,2,4-triazol-3-yl |
| 1589 | 1-[2,5-(CH₃)₂—C₆H₃]-1,2,4-triazol-3-yl |
| 1590 | 5-C(CH₃)₃-1,3,4-oxadiazol-2-yl |
| 1591 | 5-cyclopropyl-1,3,4-oxadiazol-2-yl |
| 1592 | 5-C₆H₅-1,3,4-oxadiazol-2-yl |
| 1593 | 5-(2-CH₃—C₆H₄)-1,3,4-oxadiazol-2-yl |
| 1594 | 5-(3-CH₃—C₆H₄)-1,3,4-oxadiazol-2-yl |
| 1595 | 5-(4-CH₃—C₆H₄)-1,3,4-oxadiazol-2-yl |
| 1596 | 5-(3-OCH₃—C₆H₄)-1,3,4-oxadiazol-2-yl |
| 1597 | 5-(4-OCH₃—C₆H₄)-1,3,4-oxadiazol-2-yl |
| 1598 | 5-(4-NO₂—C₆H₄)-1,3,4-oxadiazol-2-yl |
| 1599 | 5-(3-NO₂—C₆H₄)-1,3,4-oxadiazol-2-yl |
| 1600 | 5-(4-CN—C₆H₄)-1,3,4-oxadiazol-2-yl |
| 1601 | 5-(3-CN—C₆H₄)-1,3,4-oxadiazol-2-yl |
| 1602 | 5-(3-CF₃—C₆H₄)-1,3,4-oxadiazol-2-yl |
| 1603 | 5-(4-CF₃—C₆H₄)-1,3,4-oxadiazol-2-yl |
| 1604 | 5-(4-C(CH₃)₃—C₆H₄)-1,3,4-oxadiazol-2-yl |
| 1605 | 5-(2-Cl—C₆H₄)-1,3,4-oxadiazol-2-yl |
| 1606 | 5-(3-Cl—C₆H₄)-1,3,4-oxadiazol-2-yl |
| 1607 | 5-(4-Cl—C₆H₄)-1,3,4-oxadiazol-2-yl |
| 1608 | 5-(2-Br—C₆H₄)-1,3,4-oxadiazol-2-yl |
| 1609 | 5-(3-Br—C₆H₄)-1,3,4-oxadiazol-2-yl |
| 1610 | 5-(4-Br—C₆H₄)-1,3,4-oxadiazol-2-yl |
| 1611 | 5-(2-F—C₆H₄)-1,3,4-oxadiazol-2-yl |
| 1612 | 5-(3-F—C₆H₄)-1,3,4-oxadiazol-2-yl |
| 1613 | 5-(4-F—C₆H₄)-1,3,4-oxadiazol-2-yl |
| 1614 | 5-(2,4-Cl₂—C₆H₃)-1,3,4-oxadiazol-2-yl |
| 1615 | 5-(2,5-Cl₂—C₆H₃)-1,3,4-oxadiazol-2-yl |
| 1616 | 5-(2,6-Cl₂—C₆H₃)-1,3,4-oxadiazol-2-yl |
| 1617 | 5-(3,4-Cl₂—C₆H₃)-1,3,4-oxadiazol-2-yl |
| 1618 | 5-(2,4-F₂—C₆H₃)-1,3,4-oxadiazol-2-yl |
| 1619 | 5-(2,5-F₂—C₆H₃)-1,3,4-oxadiazol-2-yl |
| 1620 | 5-(2,6-F₂—C₆H₃)-1,3,4-oxadiazol-2-yl |
| 1621 | 5-(3,4-F₂—C₆H₃)-1,3,4-oxadiazol-2-yl |
| 1622 | 5-(2-Cl, 5-OCH₃—C₆H₃)-1,3,4-oxadiazol-2-yl |
| 1623 | 5-(2-Cl, 5-CH₃—C₆H₃)-1,3,4-oxadiazol-2-yl |
| 1624 | 5-(5-Cl, 2-OCH₃—C₆H₃)-1,3,4-oxadiazol-2-yl |
| 1625 | 5-(5-Cl, 2-CH₃—C₆H₃)-1,3,4-oxadiazol-2-yl |
| 1626 | 5-[2,5-(CH₃)₂—C₆H₃]-1,3,4-oxadiazol-2-yl |
| 1627 | 5-C(CH₃)₃-1,2,4-oxadiazol-3-yl |
| 1628 | 5-cyclopropyl-1,2,4-oxadiazol-3-yl |
| 1629 | 5-C₆H₅-1,2,4-oxadiazol-3-yl |
| 1630 | 5-(2-CH₃—C₆H₄)-1,2,4-oxadiazol-3-yl |
| 1631 | 5-(3-CH₃—C₆H₄)-1,2,4-oxadiazol-3-yl |
| 1632 | 5-(4-CH₃—C₆H₄)-1,2,4-oxadiazol-3-yl |
| 1633 | 5-(3-OCH₃—C₆H₄)-1,2,4-oxadiazol-3-yl |
| 1634 | 5-(4-OCH₃—C₆H₄)-1,2,4-oxadiazol-3-yl |
| 1635 | 5-(4-NO₂—C₆H₄)-1,2,4-oxadiazol-3-yl |
| 1636 | 5-(3-NO₂—C₆H₄)-1,2,4-oxadiazol-3-yl |
| 1637 | 5-(4-CN—C₆H₄)-1,2,4-oxadiazol-3-yl |
| 1638 | 5-(3-CN—C₆H₄)-1,2,4-oxadiazol-3-yl |
| 1639 | 5-(3-CF₃—C₆H₄)-1,2,4-oxadiazol-3-yl |
| 1640 | 5-(4-CF₃—C₆H₄)-1,2,4-oxadiazol-3-yl |
| 1641 | 5-(4-C(CH₃)₃—C₆H₄)-1,2,4-oxadiazol-3-yl |
| 1642 | 5-(2-Cl—C₆H₄)-1,2,4-oxadiazol-3-yl |
| 1643 | 5-(3-Cl—C₆H₄)-1,2,4-oxadiazol-3-yl |
| 1644 | 5-(4-Cl—C₆H₄)-1,2,4-oxadiazol-3-yl |
| 1645 | 5-(2-Br—C₆H₄)-1,2,4-oxadiazol-3-yl |
| 1646 | 5-(3-Br—C₆H₄)-1,2,4-oxadiazol-3-yl |
| 1647 | 5-(4-Br—C₆H₄)-1,2,4-oxadiazol-3-yl |
| 1648 | 5-(2-F—C₆H₄)-1,2,4-oxadiazol-3-yl |
| 1649 | 5-(3-F—C₆H₄)-1,2,4-oxadiazol-3-yl |
| 1650 | 5-(4-F—C₆H₄)-1,2,4-oxadiazol-3-yl |
| 1651 | 5-(2,4-Cl₂—C₆H₃)-1,2,4-oxadiazol-3-yl |
| 1652 | 5-(2,5-Cl₂—C₆H₃)-1,2,4-oxadiazol-3-yl |
| 1653 | 5-(2,6-Cl₂—C₆H₃)-1,2,4-oxadiazol-3-yl |
| 1654 | 5-(3,4-Cl₂—C₆H₃)-1,2,4-oxadiazol-3-yl |

TABLE A-continued

| No. | R⁴ |
|---|---|
| 1655 | 5-(2,4-F₂—C₆H₃)-1,2,4-oxadiazol-3-yl |
| 1656 | 5-(2,5-F₂—C₆H₃)-1,2,4-oxadiazol-3-yl |
| 1657 | 5-(2,6-F₂—C₆H₃)-1,2,4-oxadiazol-3-yl |
| 1658 | 5-(3,4-F₂—C₆H₃)-1,2,4-oxadiazol-3-yl |
| 1659 | 5-(2-Cl, 5-OCH₃—C₆H₃)-1,2,4-oxadiazol-3-yl |
| 1660 | 5-(2-Cl, 5-CH₃—C₆H₃)-1,2,4-oxadiazol-3-yl |
| 1661 | 5-(5-Cl, 2-OCH₃—C₆H₃)-1,2,4-oxadiazol-3-yl |
| 1662 | 5-(5-Cl, 2-CH₃—C₆H₃)-1,2,4-oxadiazol-3-yl |
| 1663 | 5-[2,5-(CH₃)₂—C₆H₃]-1,2,4-oxadiazol-3-yl |
| 1664 | 3-CH₃-1,2,4-oxadiazol-5-yl |
| 1665 | 3-CH(CH₃)₂-1,2,4-oxadiazol-5-yl |
| 1666 | 3-C(CH₃)₃-1,2,4-oxadiazol-5-yl |
| 1667 | 3-cyclopropyl-1,2,4-oxadiazol-5-yl |
| 1668 | 3-C₆H₅-1,2,4-oxadiazol-5-yl |
| 1669 | 3-(2-CH₃—C₆H₄)-1,2,4-oxadiazol-5-yl |
| 1670 | 3-(3-CH₃—C₆H₄)-1,2,4-oxadiazol-5-yl |
| 1671 | 3-(4-CH₃—C₆H₄)-1,2,4-oxadiazol-5-yl |
| 1672 | 3-(3-OCH₃C₆H₄)-1,2,4-oxadiazol-5-yl |
| 1673 | 3-(4-OCH₃—C₆H₄)-1,2,4-oxadiazol-5-yl |
| 1674 | 3-(4-NO₂—C₆H₄)-1,2,4-oxadiazol-5-yl |
| 1675 | 3-(3-NO₂—C₆H₄)-1,2,4-oxadiazol-5-yl |
| 1676 | 3-(4-CN—C₆H₄)-1,2,4-oxadiazol-5-yl |
| 1677 | 3-(3-CN—C₆H₄)-1,2,4-oxadiazol-5-yl |
| 1678 | 3-(3-CF₃—C₆H₄)-1,2,4-oxadiazol-5-yl |
| 1679 | 3-(4-CF₃—C₆H₄)-1,2,4-oxadiazol-5-yl |
| 1680 | 3-(4-C(CH₃)₃—C₆H₄)-1,2,4-oxadiazol-5-yl |
| 1681 | 3-(2-Cl—C₆H₄)-1,2,4-oxadiazol-5-yl |
| 1682 | 3-(3-Cl—C₆H₄)-1,2,4-oxadiazol-5-yl |
| 1683 | 3-(4-Cl—C₆H₄)-1,2,4-oxadiazol-5-yl |
| 1684 | 3-(2-Br—C₆H₄)-1,2,4-oxadiazol-5-yl |
| 1685 | 3-(3-Br—C₆H₄)-1,2,4-oxadiazol-6-yl |
| 1686 | 3-(4-Br—C₆H₄)-1,2,4-oxadiazol-5-yl |
| 1687 | 3-(2-F—C₆H₄)-1,2,4-oxadiazol-5-yl |
| 1688 | 3-(3-F—C₆H₄)-1,2,4-oxadiazol-5-yl |
| 1689 | 3-(4-F—C₆H₄)-1,2,4-oxadiazol-5-yl |
| 1690 | 3-(2,4-Cl₂—C₆H₃)-1,2,4-oxadiazol-5-yl |
| 1691 | 3-(2,5-Cl₂—C₆H₃)-1,2,4-oxadiazol-5-yl |
| 1692 | 3-(2,6-Cl₂—C₆H₃)-1,2,4-oxadiazol-5-yl |
| 1693 | 3-(3,4-Cl₂—C₆H₃)-1,2,4-oxadiazol-5-yl |
| 1694 | 3-(2,4-F₂—C₆H₃)-1,2,4-oxadiazol-5-yl |
| 1695 | 3-(2,5-F₂—C₆H₃)-1,2,4-oxadiazol-5-yl |
| 1696 | 3-(2,6-F₂—C₆H₃)-1,2,4-oxadiazol-5-yl |
| 1697 | 3-(3,4-F₂—C₆H₃)-1,2,4-oxadiazol-5-yl |
| 1698 | 3-(2-Cl, 5-OCH₃—C₆H₃)-1,2,4-oxadiazol-5-yl |
| 1699 | 3-(2-Cl, 5-CH₃—C₆H₃)-1,2,4-oxadiazol-5-yl |
| 1700 | 3-(5-Cl, 2-OCH₃—C₆H₃)-1,2,4-oxadiazol-5-yl |
| 1701 | 3-(5-Cl, 2-CH₃—C₆H₃)-1,2,4-oxadiazol-5-yl |
| 1702 | 3-[2,5-(CH₃)₂—C₆H₃]-1,2,4-oxadiazol-5-yl |
| 1703 | 5-CH₃-1,2,4-thiadiazol-3-yl |
| 1704 | 5-CH(CH₃)₂-1,2,4-thiadiazol-3-yl |
| 1705 | 5-C(CH₃)₃-1,2,4-thiadiazol-3-yl |
| 1706 | 5-cyclopropyl-1,2,4-thiadiazol-3-yl |
| 1707 | 5-C₆H₅-1,2,4-thiadiazol-3-yl |
| 1708 | 5-(2-CH₃—C₆H₄)-1,2,4-thiadiazol-3-yl |
| 1709 | 5-(3-CH₃—C₆H₄)-1,2,4-thiadiazol-3-yl |
| 1710 | 5-(4-CH₃—C₆H₄)-1,2,4-thiadiazol-3-yl |
| 1711 | 5-(3-OCH₃—C₆H₄)-1,2,4-thiadiazol-3-yl |
| 1712 | 5-(4-OCH₃—C₆H₄)-1,2,4-thiadiazol-3-yl |
| 1713 | 5-(4-NO₂—C₆H₄)-1,2,4-thiadiazol-3-yl |
| 1714 | 5-(3-NO₂—C₆H₄)-1,2,4-thiadiazol-3-yl |
| 1715 | 5-(4-CN—C₆H₄)-1,2,4-thiadiazol-3-yl |
| 1716 | 5-(3-CN—C₆H₄)-1,2,4-thiadiazol-3-yl |
| 1717 | 5-(3-CF₃—C₆H₄)-1,2,4-thiadiazol-3-yl |
| 1718 | 5-(4-CF₃—C₆H₄)-1,2,4-thiadiazol-3-yl |
| 1719 | 5-(4-C(CH₃)₃—C₆H₄)-1,2,4-thiadiazol-3-yl |
| 1720 | 5-(2-Cl—C₆H₄)-1,2,4-thiadiazol-3-yl |
| 1721 | 5-(3-Cl—C₆H₄)-1,2,4-thiadiazol-3-yl |
| 1722 | 5-(4-Cl—C₆H₄)-1,2,4-thiadiazol-3-yl |
| 1723 | 5-(2-Br—C₆H₄)-1,2,4-thiadiazol-3-yl |
| 1724 | 5-(3-Br—C₆H₄)-1,2,4-thiadiazol-3-yl |
| 1725 | 5-(4-Br—C₆H₄)-1,2,4-thiadiazol-3-yl |
| 1726 | 5-(2-F—C₆H₄)-1,2,4-thiadiazol-3-yl |
| 1727 | 5-(3-F—C₆H₄)-1,2,4-thiadiazol-3-yl |
| 1728 | 5-(4-F—C₆H₄)-1,2,4-thiadiazol-3-yl |
| 1729 | 5-(2,4-Cl₂—C₆H₃)-1,2,4-thiadiazol-3-yl |
| 1730 | 5-(2,5-Cl₂—C₆H₃)-1,2,4-thiadiazol-3-yl |
| 1731 | 5-(2,6-Cl₂—C₆H₃)-1,2,4-thiadiazol-3-yl |
| 1732 | 5-(3,4-Cl₂—C₆H₃)-1,2,4-thiadiazol-3-yl |
| 1733 | 5-(2,4-F₂—C₆H₃)-1,2,4-thiadiazol-3-yl |
| 1734 | 5-(2,5-F₂—C₆H₃)-1,2,4-thiadiazol-3-yl |
| 1735 | 5-(2,6-F₂—C₆H₃)-1,2,4-thiadiazol-3-yl |
| 1736 | 5-(3,4-F₂—C₆H₃)-1,2,4-thiadiazol-3-yl |
| 1737 | 5-(2-Cl, 5-OCH₃—C₆H₃)-1,2,4-thiadiazol-3-yl |
| 1738 | 5-(2-Cl, 5-CH₃—C₆H₃)-1,2,4-thiadiazol-3-yl |
| 1739 | 5-(5-Cl, 2-OCH₃—C₆H₃)-1,2,4-thiadiazol-3-yl |
| 1740 | 5-(5-Cl, 2-CH₃—C₆H₃)-1,2,4-thiadiazol-3-yl |
| 1741 | 5-[2,5-(CH₃)₂—C₆H₃]-1,2,4-thiadiazol-3-yl |
| 1742 | 5-CH₃-1,3,4-thiadiazol-2-yl |
| 1743 | 5-CH(CH₃)₂-1,3,4-thiadiazol-2-yl |
| 1744 | 5-C(CH₃)₃-1,3,4-thiadiazol-2-yl |
| 1745 | 5-cyclopropyl-1,3,4-thiadiazol-2-yl |
| 1746 | 5-C₆H₅1,3,4-thiadiazol-2-yl |
| 1747 | 5-(2-CH₃—C₆H₄)-1,3,4-thiadiazol-2-yl |
| 1748 | 5-(3-CH₃—C₆H₄)-1,3,4-thiadiazol-2-yl |
| 1749 | 5-(4-CH₃—C₆H₄)-1,3,4-thiadiazol-2-yl |
| 1750 | 5-(3-OCH₃—C₆H₄)-1,3,4-thiadiazol-2-yl |
| 1751 | 5-(4-OCH₃—C₆H₄)-1,3,4-thiadiazol-2-yl |
| 1752 | 5-(4-NO₂—C₆H₄)-1,3,4-thiadiazol-2-yl |
| 1753 | 5-(3-NO₂—C₆H₄)-1,3,4-thiadiazol-2-yl |
| 1754 | 5-(4-CN—C₆H₄)-1,3,4-thiadiazol-2-yl |
| 1755 | 5-(3-CN—C₆H₄)-1,3,4-thiadiazol-2-yl |
| 1756 | 5-(3-CF₃—C₆H₄)-1,3,4-thiadiazol-2-yl |
| 1757 | 5-(4-CF₃—C₆H₄)-1,3,4-thiadiazol-2-yl |
| 1758 | 5-(4-C(CH₃)₃—C₆H₄)-1,3,4-thiadiazol-2-yl |
| 1759 | 5-(2-Cl—C₆H₄)-1,3,4-thiadiazol-2-yl |
| 1760 | 5-(3-Cl—C₆H₄)-1,3,4-thiadiazol-2-yl |
| 1761 | 5-(4-Cl—C₆H₄)-1,3,4-thiadiazol-2-yl |
| 1762 | 5-(2-Br—C₆H₄)-1,3,4-thiadiazol-2-yl |
| 1763 | 5-(3-Br—C₆H₄)-1,3,4-thiadiazol-2-yl |
| 1764 | 5-(4-Br—C₆H₄)-1,3,4-thiadiazol-2-yl |
| 1765 | 5-(2-F—C₆H₄)-1,3,4-thiadiazol-2-yl |
| 1766 | 5-(3-F—C₆H₄)-1,3,4-thiadiazol-2-yl |
| 1767 | 5-(4-F—C₆H₄)-1,3,4-thiadiazol-2-yl |
| 1768 | 5-(2,4-Cl₂—C₆H₃)-1,3,4-thiadiazol-2-yl |
| 1769 | 5-(2,5-Cl₂—C₆H₃)-1,3,4-thiadiazol-2-yl |
| 1770 | 5-(2,6-Cl₂—C₆H₃)-1,3,4-thiadiazol-2-yl |
| 1771 | 5-(3,4-Cl₂—C₆H₃)-1,3,4-thiadiazol-2-yl |
| 1772 | 5-(2,4-F₂—C₆H₃)-1,3,4-thiadiazol-2-yl |
| 1773 | 5-(2,5-F₂—C₆H₃)-1,3,4-thiadiazol-2-yl |
| 1774 | 5-(2,6-F₂—C₆H₃)-1,3,4-thiadiazol-2-yl |
| 1775 | 5-(3,4-F₂—C₆H₃)-1,3,4-thiadiazol-2-yl |
| 1776 | 5-(2-Cl, 5-OCH₃—C₆H₃)-1,3,4-thiadiazol-2-yl |
| 1777 | 5-(2-Cl, 5-CH₃—C₆H₃)-1,3,4-thiadiazol-2-yl |
| 1778 | 5-(5-Cl, 2-OCH₃—C₆H₃)-1,3,4-thiadiazol-2-yl |
| 1779 | 5-(5-Cl, 2-CH₃—C₆H₃)-1,3,4-thiadiazol-2-yl |
| 1780 | 5-[2,5-(CH₃)₂—C₆H₃]-1,3,4-thiadiazol-2-yl |
| 1781 | 1-CH(CH₃)₂-imidazol-4-yl |
| 1782 | 1-C(CH₃)₃-imidazol-4-yl |
| 1783 | 1-cyclopropylimidazol-4-yl |
| 1784 | 1-C₆H₅-imidazol-4-yl |
| 1785 | 1-(2-CH₃—C₆H₄)imidazol-4-yl |
| 1786 | 1-(3-CH₃—C₆H₄)imidazol-4-yl |
| 1787 | 1-(4-CH₃—C₆H₄)imidazol-4-yl |
| 1788 | 1-(3-OCH₃—C₆H₄)imidazol-4-yl |
| 1789 | 1-(4-OCH₃—C₆H₄)imidazol-4-yl |
| 1790 | 1-(4-NO₂—C₆H₄)imidazol-4-yl |
| 1791 | 1-(3-NO₂—C₆H₄)imidazol-4-yl |
| 1792 | 1-(4-CN—C₆H₄)imidazol-4-yl |
| 1793 | 1-(3-CN—C₆H₄)imidazol-4-yl |
| 1794 | 1-(3-CF₃—C₆H₄)imidazol-4-yl |
| 1795 | 1-(4-CF₃—C₆H₄)imidazol-4-yl |
| 1796 | 1-(4-C(CH₃)₃—C₆H₄)imidazol-4-yl |
| 1797 | 1-(2-Cl—C₆H₄)imidazol-4-yl |
| 1798 | 1-(3-Cl—C₆H₄)imidazol-4-yl |
| 1799 | 1-(4-Cl—C₆H₄)imidazol-4-yl |
| 1800 | 1-(2-Br—C₆H₄)imidazol-4-yl |
| 1801 | 1-(3-Br—C₆H₄)imidazol-4-yl |
| 1802 | 1-(4-Br—C₆H₄)imidazol-4-yl |
| 1803 | 1-(2-F—C₆H₄)imidazol-4-yl |
| 1804 | 1-(3-F—C₆H₄)imidazol-4-yl |
| 1805 | 1-(4-F—C₆H₄)imidazol-4-yl |
| 1806 | 1-(2,4-Cl₂—C₆H₃)imidazol-4-yl |
| 1807 | 1-(2,5-Cl₂—C₆H₃)imidazol-4-yl |
| 1808 | 1-(2,6-Cl₂—C₆H₃)imidazol-4-yl |

TABLE A-continued

| No. | R⁴ |
|---|---|
| 1809 | 1-(3,4-Cl$_2$—C$_6$H$_3$)imidazol-4-yl |
| 1810 | 1-(2,4-F$_2$—C$_6$H$_3$)imidazol-4-yl |
| 1811 | 1-(2,5-F$_2$—C$_6$H$_3$)imidazol-4-yl |
| 1812 | 1-(2,6-F$_2$—C$_6$H$_3$)imidazol-4-yl |
| 1813 | 1-(3,4-F$_2$—C$_6$H$_3$)imidazol-4-yl |
| 1814 | 1-(2-Cl, 5-OCH$_3$—C$_6$H$_3$)imidazol-4-yl |
| 1815 | 1-(2-Cl, 5-CH$_3$—C$_6$H$_3$)imidazol-4-yl |
| 1816 | 1-(5-Cl, 2-OCH$_3$—C$_6$H$_3$)imidazol-4-yl |
| 1817 | 1-(5-Cl, 2-CH$_3$—C$_6$H$_3$)imidazol-4-yl |
| 1818 | 1-[2,5-(CH$_3$)$_2$—C$_6$H$_3$]imidazol-4-yl |

The compounds I are suitable as fungicides.

The compounds I are distinguished by an outstanding activity against a broad spectrum of phytopathogenic fungi, in particular from the class of Ascomycetes, Deuteromycetes, Phycomycetes and Basidiomycetes. They are systemically active in some cases and can be employed as foliar and soil fungicides. They are of particular importance for the control of a multiplicity of fungi on various crop plants such as wheat, rye, barley, oats, bananas, rice, corn, grass, cotton, soybeans, coffee, sugar cane, grapes, fruit and decorative plants and vegetable plants such as cucumbers, beans, tomatoes, potatoes and cucurbits, and on the seeds of these plants.

They are specifically suitable for the control of the following plant diseases: Erysiphe graminis (powdery mildew) in cereals, Erysiphe cichoracearum and Sphaerotheca fuliginea on cucurbits, Podosphaera leucotricha on apples, Uncinula necator on vines, Puccinia species on cereals, Rhizoctonia species on cotton, rice and grass, Ustilago species on cereals and sugar cane, Venturia inaequalis (scab) on apples, Helminthosporium species on cereals, Septoria nodorum on wheat, Botrytis cinerea (gray mold) on strawberries, vines, vegetables and decorative plants, Cercospora arachidicola on groundnuts, Pseudocercosporella herpotrichoides on wheat, barley, Pyricularia oryzae on rice, Phytophthora infestans on potatoes and tomatoes, Fusarium and Verticillium species on various plants, Plasmopara viticola on vines, Pseudoperonospora species in hops and cucumbers, Alternaria species on vegetables and fruit and Mycosphaerella species in bananas.

The compounds I are applied by treating the fungi or the plants, seeds, materials or the soil to be protected from fungal attack with a fungicidally effective amount of the active compounds. They are applied before or after the infection of the materials, plants or seeds by the fungi.

Using formulation auxiliaries known per se, they can be converted into the customary formulations (compositions), such as solutions, emulsions, suspensions, dusts, powders, pastes and granules. The application form depends on the particular intended use; in each case it should guarantee a fine and uniform distribution of the compounds I. The formulations are prepared in a known manner, eg. by extending the active compound with solvents and/or carriers, if desired using emulsifiers and dispersants, it being possible in the case of water as a diluent also to use other organic solvents as auxiliary solvents. Suitable auxiliaries for this purpose are essentially: solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water; carriers such as ground natural minerals (eg. kaolins, argillaceous earths, talc, chalk) and ground synthetic minerals (eg. highly disperse silica, silicates); emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

The fungicidal compositions in general contain from 0.1 to 95, preferably from 0.5 to 90, % by weight of active compound.

Depending on the type of effect desired, the application rates are from 0.01 to 2.0 kg of active compound per ha.

In seed treatment, amounts of active compound of from 0.001 to 0.1 g, preferably 0.01 to 0.05 g, per kilogram of seed are in general needed.

The compositions according to the invention can also be present in the application form as fungicides together with other active compounds, eg. with herbicides, insecticides, growth regulators, fungicides or alternatively with fertilizers.

On mixing with fungicides, in many cases an increase in the fungicidal spectrum of action is obtained here.

The following list of fungicides with which the compounds according to the invention can be applied together is intended to illustrate the combination possibilities, but not restrict them:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N-propylenebisdithiocarbamate), N,N'-polypropylenebis (thiocarbamoyl) disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropyl carbonate, diisopropyl 5-nitroisophthalate;

heterocyclic substances, such as 2-heptadecyl-2-imidazoline acetate, 2,4-dichloro-6-(o-chloroanilino) triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-ethoxycarbonylaminobenzimidazole, 2-(fur-2-yl) benzimidazole, 2-(thiazol-4-yl)benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, 2-thiopyridine-1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(1-(2,2,2-trichloroethyl))formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and various fungicides, such as dodecylguanidine acetate, 3-[3-(3,5-dimethyl-2-oxycyclohexyl)-2-hydroxyethyl] glutarimide, hexachlorobenzene, DL-methyl-N-(2,6-dimethylphenyl)-N-2-furoyl alaninate, DL-N-(2,6-dimethylphenyl)-N-(2'-methoxyacetyl)alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-(3,5-dichlorophenyl)-5-methyl-5-methoxymethyl-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-ethylaminocarbonyl-2-methoximino]acetamide, 1-[2-(2,4-dichlorophenyl)pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl)methylsilyl)methyl)-1H-1,2,4-triazole;

strobilurins such as methyl E-methoximino[α-(o-tolyloxy)-o-tolyl]acetate, methyl E-2-{2-[6-(2-cyanophenoxy)pyrimidin-4-yloxy]phenyl}-3-methoxyacrylate, methyl E-methoximino-[α-(2-phenoxyphenyl)]acetamide, methyl E-methoximino-[α-(2,5-dimethylphenoxy)-o-tolyl]acetamide;

anilinopyrimidines such as N-(4,6-dimethylpyrimidin-2-yl)aniline, N-[4-methyl-6-(1-propynyl)pyrimidin-2-yl] aniline, N-(4-methyl-6-cyclopropylpyrimidin-2-yl)aniline;

phenylpyrroles such as 4-(2,2-difluoro-1,3-benzodioxol-4-yl)-pyrrole-3-carbonitrile, cinnamamides such as 3-(4-chlorophenyl)-3-(3,4-dimethoxyphenyl)acrylic acid morpholide;

(2RS,3SR)-1-[3-(2-chlorophenyl)-2-[4-fluorophenyl)oxiran-2-yl-methyl]-1H-1,2,4-triazole.

The compounds of the formula I are additionally suitable for controlling pests of the insects, arachnids and nematodes classes. They can be employed as pesticides in crop protection and in the hygiene, stored material protection and veterinary sectors.

The harmful insects include: from the order of the butterflies (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyya platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci;*

From the order of the hymenopterans (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the bugs (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the plant-sucking insects (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the order of the Arachnoidea, for example, spiders (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root gall nematodes, eg. *Meloidogyne hapla, Meloidogyne incognita, Meloidogyne javanica,* cyst-forming nematodes, eg. *Globodera rostochiensis, Heterodera avenae, Heterodera glycines, Heterodera schachtii, Heterodera trifolii,* stem and leaf nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The compounds I can be applied as such, in the form of their formulations (compositions) obtained using formulation auxiliaries known per se or the application forms prepared therefrom, eg. in the form of directly sprayable solutions, powders, suspensions or dispersions, emulsions, oil dispersions, pastes, dust compositions, scattering compositions or granules, by spraying, atomizing, dusting, scattering or watering. The application forms depend entirely on the intended uses; in each case they should if possible guarantee the finest distribution of the active compounds according to the invention.

The active compound concentrations in the ready-to-use preparations can be varied within relatively wide ranges.

In general, they are from 0.0001 to 10%, preferably from 0.01 to 1%.

The active compounds can also be used with good effect in the ultra-low volume method (ULV), it being possible to apply formulations containing more than 95% by weight of active compound or even the active compound without additives.

Under outdoor conditions, the application rate of active compound for controlling pests is from 0.1 to 2.0, preferably 0.2 to 1.0 kg/ha.

For the preparation of directly sprayable solutions, emulsions, pastes or oil dispersions, mineral oil fractions of medium to high boiling point are suitable, such as kerosene or diesel oil, furthermore coal tar oils and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Aqueous application forms can be prepared from emulsion concentrates, pastes or wettable powders (wettable powders, oil dispersions) by addition of water. To prepare emulsions, pastes or oil dispersions, the substances can be homogenized in water as such or dissolved in an oil or solvent, by means of wetting agents, adherents, dispersants or emulsifiers. However, concentrates consisting of active substance, wetting agent, adherent, dispersant or emulsifier and possibly solvent or oil can also be prepared which are suitable for dilution with water.

Suitable surface-active substances are the alkali metal, alkaline earth metal and ammonium salts of lignosulfonic acid, naphthalenesulfonic acid, phenolsulfonic acid and dibutylnaphthalenesulfonic acid, alkylarylsulfonates, alkylsulfates, alkylsulfonates, fatty alcohol sulfates and fatty acids and also their alkali metal and alkaline earth metal salts, salts of sulfated fatty alcohol glycol ethers, condensation products of sulfonated naphthalene and naphthalene derivatives with formaldehyde, condensation products of naphthalene or of naphthalenesulfonic acid with phenol and formaldehyde, polyoxyethylene octylphenyl ether, ethoxylated isooctylphenol, octylphenol or nonylphenol, alkylphenyl polyglycol ether, tributylphenyl polyglycol ether, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetate, sorbitol esters, lignosulfite waste liquors or methylcellulose.

Powder, scattering and dusting compositions can be prepared by mixing or joint grinding of the active substances with a solid carrier.

The formulations in general contain from 0.01 to 95% by weight, preferably from 0.1 to 90% by weight, of the active compound. The active compounds are employed here in a purity of from 90% to 100%, preferably 95% to 100% (according to NMR spectrum).

Examples of formulations are:

I. 5 parts by weight of a compound I according to the invention are intimately mixed with 95 parts by weight of finely divided kaolin. In this way a dusting composition is obtained which contains 5% by weight of the active compound.

II. 30 parts by weight of a compound I according to the invention are intimately mixed with a mixture of 92 parts by weight of powdered silica gel and 8 parts by weight of paraffin oil which has been sprayed onto the surface of this silica gel. In this manner a preparation of the active compound having good adherence is obtained (active compound content 23% by weight).

III. 10 parts by weight of a compound I according to the invention are dissolved in a mixture which consists of 90 parts by weight of xylene, 6 parts by weight of the addition product of from 8 to 10 mol of ethylene oxide to 1 mol of oleic acid N-monoethanolamide, 2 parts by weight of calcium salt of dodecylbenzenesulfonic acid and 2 parts by weight of the addition product of 40 mol of ethylene oxide to 1 mol of castor oil (active compound content 9% by weight).

IV. 20 parts by weight of a compound I according to the invention are dissolved in a mixture which consists of 60 parts by weight of cyclohexanone, 30 parts by weight of isobutanol, 5 parts by weight of the addition product of 7 mol of ethylene oxide to 1 mol of isooctylphenol and 5 parts by weight of the addition product of 40 mol of ethylene oxide to 1 mol of castor oil (active compound content 16% by weight).

V. 80 parts by weight of a compound I according to the invention are well mixed with 3 parts by weight of sodium salt of diisobutylnaphthalene-alpha-sulfonic acid, 10 parts by weight of the sodium salt of a lignosulfonic acid from a sulfite waste liquor and 7 parts by weight of powdered silica gel and the mixture is ground in a hammer mill (active compound content 80% by weight).

VI. 90 parts by weight of a compound I according to the invention are mixed with 10 parts by weight of N-methyl-α-pyrrolidone and a solution is obtained which is suitable for application in the form of very small drops (active compound content 90% by weight).

VII. 20 parts by weight of a compound I according to the invention are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into and finely dispersing it in 100,000 parts by weight of water, an aqueous dispersion is obtained which contains 0.02% by weight of the active compound.

VIII. 20 parts by weight of a compound I according to the invention are well mixed with 3 parts by weight of sodium salt of diisobutylnaphthalene-α-sulfonic acid, 17 parts by weight of the sodium salt of a lignosulfonic acid from a sulfite waste liquor and 60 parts by weight of powdered silica gel and the mixture is ground in a hammer mill. By finely dispersing the mixture in 20,000 parts by weight of water, a spray mixture is obtained which contains 0.1% by weight of the active compound.

Granules, eg. coated, impregnated and homogeneous granules, can be prepared by binding the active compounds to solid carriers.

Solid carriers are, for example, mineral earths, such as silicic acids, silica gels, silicates, talc, kaolin, attapulgous clay, limestone, lime, chalk, bole, loess, clay, dolomite, diatomaceous earth, calcium and magnesium sulfate, magnesium oxide, ground synthetic materials, fertilizers, such as eg. ammonium sulfate, ammonium phosphate, ammonium nitrate, ureas and vegetable products, such as grain flour, tree bark, wood and nutshell meal, cellulose powder and other solid carriers.

Oils of various types, herbicides, fungicides, other pesticides and bactericides can be added to the active compounds, if desired only immediately before application (tank mix). These agents can be admixed with the agents according to the invention in a weight ratio from 1:10 to 10:1.

SYNTHESIS EXAMPLES

The chemical shifts (in ppm) of the ¹H-NMR spectra were measured against tetramethylsilane (br=broad signal, s=singlet, d=doublet, m=multiplet).

EXAMPLE 1

Preparation of the compound S1

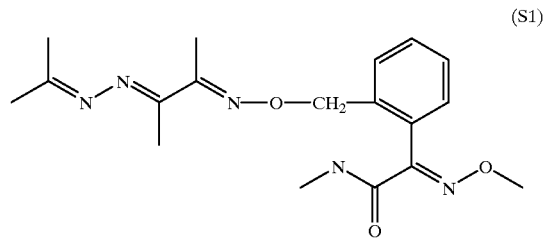

9.2 g (0.03 mol) of methyl (E,E)-2-methoxyimino-2-(2'-[{1"-methyl,1"-acetyl}iminooxymethyl]phenyl)acetate (cf. WO-A 95/21153) were dissolved in 200 ml of tetrahydrofuran, treated with 50 ml of 40% strength by weight aqueous monomethylamine solution and allowed to stand at room temperature for 2 hours. The mixture was then treated with 2N hydrochloric acid, extracted with methyl tert-butyl ether, the organic phase was washed with water and dried over sodium sulfate, and the solvent was removed. As a residue, 7.7 g of (E,E)-2-methoxyimino-2-(2'-[{1"-methyl,1"-acetyl}iminooxymethyl]phenyl)acetic acid monomethylamide remained as colorless crystals of melting point 89–92° C. A solution of 3.7 g (0.012 mol) of this compound in 50 ml of tetrahydrofuran was added to a solution of 2.4 g (0.048 mol) of hydrazine hydrate in 50 ml of tetrahydrofuran and the mixture was stirred at room temperature for 60 hours. It was then treated with water, extracted with methyl tert-butyl ether, the organic phase was washed with water and dried over sodium sulfate, and the solvent was removed. As a residue, 3.5 g of (E,E,E)-2-methoxyimino-2-(2'-[{1"-methyl,1"-{1'"-hydrazonoethyl}}iminooxymethyl]phenyl)acetic acid monomethylamide remained as a colorless oil.

1H-NMR (CDCl₃): 1.89 (s, 3H); 1.99 (s, 3H); 2.9 (d, 3H); 3.94 (s, 3H); 5.05 (s, 2H); 5.44 (s, br, 2H); 6.71 (s, br, 1H); 7.15–7.47 (m, 4H).

1.6 g (0.005 mol) of this compound were dissolved in 100 ml of acetone. After addition of 1 drop of acetic acid, the reaction mixture was allowed to stand at room temperature for 60 hours. The acetone was then stripped off, the residue was taken up in methyl tert-butyl ether and water, the mixture was extracted with methyl tert-butyl ether and the organic phase was washed with water and dried over sodium sulfate. The solvent was then removed from the organic phase. As a residue, 1.7 g of the compound "S1" remained as a colorless oil.

¹H-NMR (CDCl₃): 1.8 (s, 3H); 1.94 (s, 3H); 2.05 (s, 6H); 2.9 (d, 3H); 3.96 (s, 3H); 5.1 (s, 2H); 6.75 (s, br, 1H); 7.17–7.5 (m, 4H).

EXAMPLE 2

Preparation of the compound S2

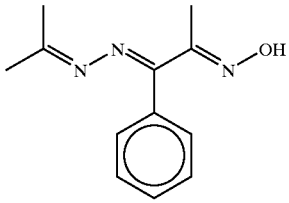
(S2)

A solution of 20 g (0.11 mol) of 1-hydrazono-1-phenylpropan-2-one oxime [J. Med. Chem. 21 (1978), 623–8] in 300 ml of acetone was stirred at room temperature for 1 hour. After stripping off the solvent in a rotary evaporator, the residue was crystallized from methanol. 9.5 g (40% yield) of the compound S2 were thus obtained as colorless crystals of melting point 127–130° C.

$^1$H-NMR (CDCl$_3$): δ=1.87 (s,6H); 2.18 (s,3H); 6.98–7.36 (m,5H); 8.56 (s,br,1H).

EXAMPLE 3

Preparation of the compound S3

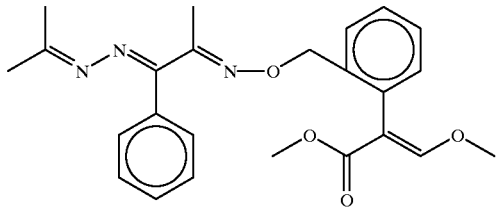
(S3)

2.5 g (11.5 mmol) of 1-(isopropylidenehydrazono)-1-phenylpropan-2-one oxime (compound S2), dissolved in 50 ml of dimethylformamide, were added to 0.29 g (12 mmol) of sodium hydride in 50 ml of dimethylformamide. The mixture was stirred for 30 min, then 3.3 g (11.5 mmol) of methyl (E)-3-methoxy-2-[(2'-bromomethyl)phenyl]acrylate were added and the reaction mixture was stirred at room temperature for 16 hours. It was poured onto water and extracted with tert-butyl methyl ether. The organic phase was washed with water, dried and concentrated. After column chromatography on silica gel (tert-butyl methyl ether/cyclohexane/2% triethylamine), 1.7 g (35% yield) of the compound S3 were obtained as a colorless oil.

IR (film): 2940, 1709, 1634, 1435, 1284, 1256, 1191, 1130, 1111, 1056, 1009 cm$^{-1}$.

EXAMPLE 4

Preparation of the compound S4

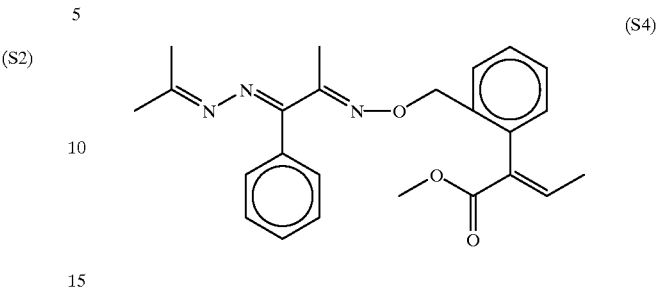
(S4)

2.5 g (11.5 mmol) of 1-(isopropylidenehydrazono)-1-phenylpropan-2-one oxime (compound S2), dissolved in 50 ml of dimethylformamide, were added to 0.29 g (12 mmol) of sodium hydride in 50 ml of dimethylformamide. The mixture was stirred for 30 min, then 3.1 g (11.5 mmol) of methyl (E)-3-methyl-2-[(2'-bromomethyl)phenyl]acrylate were added and the reaction mixture was stirred at room temperature for 16 hours. It was poured onto water and extracted with tert-butyl methyl ether. The organic phase was washed with water, dried and concentrated. After column chromatography on silica gel (tert-butyl methyl ether/cyclohexane/2% triethylamine), 2.3 g (49% yield) of the compound S4 were obtained as a colorless oil.

$^1$H-NMR (CDCl$_3$): δ=1.49 (d,3H); 1.89 (s,6H); 2.21 (s,3H); 3.64 (s,3H); 4.87–4.93 (m,2H); 6.98–7.36 (m,9H).

EXAMPLE 5

Preparation of the compound S5

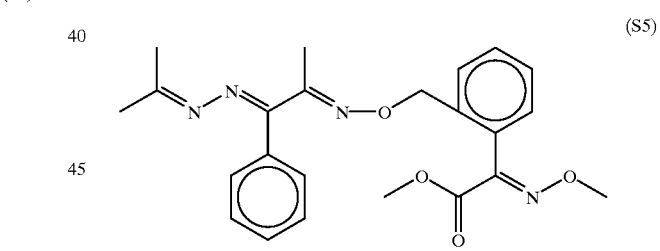
(S5)

4.3 g (20 mmol) of 1-(isopropylidenehydrazono)-1-phenylpropan-2-one oxime (compound S2), dissolved in 50 ml of dimethylformamide, were added to 0.5 g (21 mmol) of sodium hydride in 50 ml of dimethylformamide. The mixture was stirred for 30 min, then 5.7 g (20 mmol) of methyl (E)-2-methoxyimino-2-[(2'-bromomethyl)phenyl]acetate were added and the reaction mixture was stirred at room temperature for 16 hours. It was poured onto water and extracted with tert-butyl methyl ether. The organic phase was washed with water, dried and concentrated. After column chromatography on silica gel (tert-butyl methyl ether/cyclohexane/2% triethylamine), 4.2 g (50% yield) of the compound S5 were obtained as a colorless oil.

$^1$H-NMR (CDCl$_3$): δ=1.89 (s,6H); 2.17 (s,3H); 3.82 (s,3H); 3.97 (s,3H); 4.93 (s,2H); 7.00–7.40 (m,9H).

EXAMPLE 6

Preparation of the compound S6

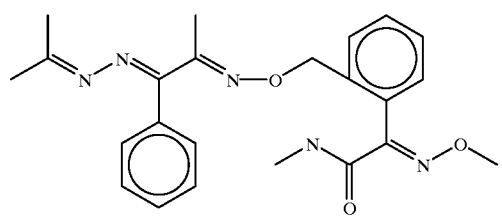
(S6)

3.0 g (7.1 mmol) of the compound S5 were dissolved in 100 ml of tetrahydrofuran, treated with 20 ml of 40% strength aqueous monomethylamine solution and stirred at room temperature for 1 hour. The mixture was then treated with water, extracted with tert-butyl methyl ether and the organic phase was washed with water, dried over sodium sulfate and concentrated in a rotary evaporator. 3.0 g of the compound S6 were thus obtained as a colorless oil.

$^1$H-NMR (CDCl$_3$): δ=1.89 (s,6H); 2.18 (s,3H); 2.85 (d,3H); 3.88 (s,3H); 4.94 (s,2H); 6.64 (s,br,1H); 6.98–7.38 (M,9H).

Compounds of the formula I can quite generally be prepared in a similar manner to that described above for the compounds S1 to S6.

Table I below shows the physical data of other prepared compounds according to the invention. The compounds S1, S3, S4, S5 and S6 are additionally included in the table.

TABLE 1

| No. | R$^1$ | Y | X | (R$^2$)$_m$ | R$^3$ | R$^4$ | R$^5$ | R$^6$ | Data |
|---|---|---|---|---|---|---|---|---|---|
| I.1 | CH$_3$ | NH | NOCH$_3$ - (E) | H | CH$_3$ | CH$_3$ | CH$_3$ | CH$_3$ | see Example S1 |
| I.2 | CH$_3$ | NH | NOCH$_3$ - (E) | H | CH$_3$ | CH$_3$ | C$_6$H$_5$ | H | IR (film): 3340, 2930, 1673, 1614, 1525, 1448, 1362, 1038, 999, 979, 760, 695 cm$^{-1}$ |
| I.3 | CH$_3$ | O | NOCH$_3$ - (E) | H | CH$_3$ | C$_6$H$_5$ | C$_2$H$_5$ | CH$_3$ | IR (film): 2940, 1727, 1443, 1437, 1218, 1199, 1069, 1048, 1018, 958, 698 cm$^{-1}$ |
| I.4 | CH$_3$ | O | CHOCH$_3$ - (E) | H | CH$_3$ | C$_6$H$_5$ | C$_2$H$_5$ | CH$_3$ | $^1$H-NMR (CDCl$_3$): δ = 0.93 ((t, 3H); 1.82 (s, 3H); 2.16 (q, 2H); 2.21 (s, 3H); 3.64 (s, 3H); 3.74 (s, 3H); 4.97 (s, 2H); 7.05–7.51 (m, 10H) ppm |
| I.5 | CH$_3$ | O | NOCH$_3$ - (E) | H | CH$_3$ | C$_6$H$_5$ | CH$_3$ | H | $^1$H-NMR (CDCl$_3$): δ = 1.94 and 1.85 (d, 3H); 2.15 and 2.18 (s, 3H); 3.82 and 3.79 (s, 3H); 3.97 and 4.0 (s, 3H); 4.85–5.12 (m, 2H); 7.0–7.83 (m, 10H) ppm |
| I.6 | CH$_3$ | NH | NOCH$_3$ - (E) | H | CH$_3$ | C$_6$H$_5$ | C$_2$H$_5$ | CH$_3$ | m.p. 75–78° C. |
| I.7 | CH$_3$ | O | CHCH$_3$ - (E) | H | CH$_3$ | C$_6$H$_5$ | C$_2$H$_5$ | CH$_3$ | IR (film): 2960, 1717, 1143, 1435, 1364, 1252, 1208, 1036, 1010, 764, 696 cm$^{-1}$ |
| I.8 | CH$_3$ | O | NOCH$_3$ - (E) | H | CH$_3$ | C$_6$H$_5$ | CH$_3$ | CH$_3$ | see Example S5 |
| I.9 | CH$_3$ | O | CHOCH$_3$ - (E) | H | CH$_3$ | C$_6$H$_5$ | CH$_3$ | CH$_3$ | see Example S3 |
| I.10 | CH$_3$ | O | CHCH$_3$ - (E) | H | CH$_3$ | C$_6$H$_5$ | CH$_3$ | CH$_3$ | see Example S4 |
| I.11 | CH$_3$ | NH | NOCH$_3$ - (E) | H | CH$_3$ | C$_6$H$_5$ | CH$_3$ | H | $^1$H-NMR (CDCl$_3$): δ = 1.95 and 1.86 (d, 3H); 2.16 and 2.19 (s, 3H); 2.87 and 2.78 (d, 3H); 3.89 and 3.92 (s, 3H); 4.86–5.09 (m, 2H); 6.62 and 6.83 (s, br, 1H); 7.0–7.88 (m, 10H) ppm |
| I.12 | CH$_3$ | NH | NOCH$_3$ - (E) | H | CH$_3$ | C$_6$H$_5$ | CH$_3$ | CH$_3$ | see Example S6 |

USE EXAMPLES

1. Examples of action against harmful fungi: wheat mildew

Leaves of wheat seedlings of the variety "Frühgold" grown in pots were sprayed until dripping wet using an aqueous spray mixture which was prepared using a stock solution of 10% active compound, 63% cyclohexanone and 27% emulsifier and dusted 24 hours after the spray coating had dried on with spores of wheat mildew (Erysiphe graminis var. tritici). The test plants ere then placed in a greenhouse at from 20 to 22° C. and 75 to 80% relative atmospheric humidity. After 7 days, the extent of mildew development was assessed visually in % attack of the total leaf area.

| Active compound | % attack on the leaves after application of aqueous active compound preparation comprising 63 ppm of active compound |
|---|---|
| I.1 | 5 |
| I.2 | 5 |
| I.3 | 15 |
| I.5 | 15 |
| I.7 | 15 |
| I.8 | 15 |
| I.9 | 15 |
| I.10 | 15 |
| Comparison substance A Compound 3.81 from Table 3 of WO 95/18 789 | 60 |
| Untreated | 75 |

2. Examples of action against animal pests

It was possible to show the action of the compounds of the general formula I against animal pests by the following tests:

The active compounds were prepared
a) as a 0.1% strength solution in acetone or
b) as a 10% strength emulsion in a mixture of 70% by weight of cyclohexanone, 20% by weight of Nekanil® LN (Lutensol® AP6, wetting agent having emulsifier and dispersant action based on ethoxylated alkylphenols) and 10% by weight of Emulphor® EL (Emulan® EL, emulsifier based on ethoxylated fatty alcohols)
and diluted with acetone in the case of a) or with water in the case of b) according to the concentration desired.

After conclusion of the tests, the lowest concentration in each case was determined at which the compounds still produced an 80–100% inhibition or mortality in comparison with the untreated control tests (activity threshold or minimum concentration).

We claim:

1. An azinooxime ether of the formula I

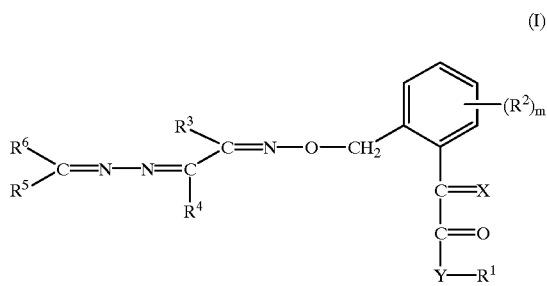

where the variables have the following meanings:
X is $NOCE_3$, $CHOCH_3$ or $CHCH_3$;
Y is O or NZ, Z being hydrogen or $C_1$–$C_4$-alkyl;
$R^1$ is hydrogen or $C_1$–$C_4$-alkyl;
$R^2$ is cyano, nitro, halogen, $C_1$–$C_4$-alkyl, trifluoromethyl or $C_1$–$C_4$-alkoxy;
m is 0, 1 or 2, it being possible for the radicals $R^2$ to be different if m is 2;
$R^3$ is hydrogen, cyano, alkyl, haloalkyl, alkoxy or cycloalkyl;
$R^4$, $R^5$, $R^6$ independently of one another are: hydrogen or unsubstituted or substituted alkyl, alkenyl, alkynyl, cycloalkyl, cycloalkenyl, heterocyclyl, aryl or heteroaryl,
or its salts.

2. A process for preparing compounds of the formula I as claimed in claim 1, which comprises reacting a benzyl derivative of the formula II

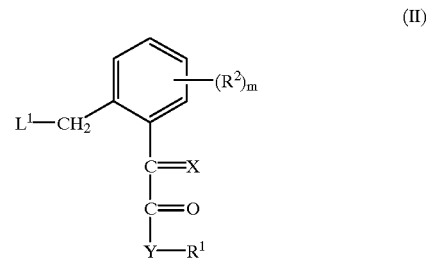

where $L^1$ is a nucleophilically replaceable leaving group with a hydroxyimine of the formula III

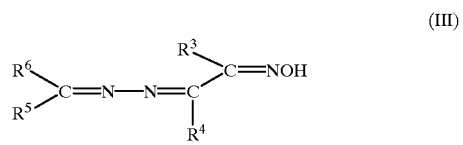

3. A process for preparing compounds of the formula I as claimed in claim 1, which comprises reacting a benzyl derivative of the formula II as set forth in claim 2 with a hydroxyimine of the formula V

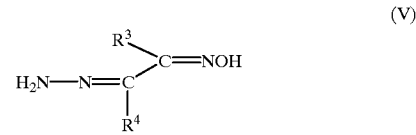

to give a compound of the formula IX

and then reacting IX with a carbonyl compound of the formula VI

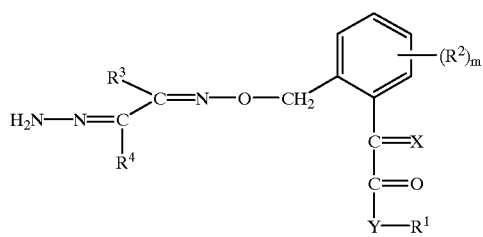

(IX)

4. A process for preparing compounds of the formula I as claimed in claim 1, which comprises reacting a carbonyl compound of the formula VIII

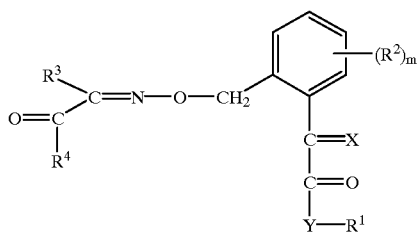

(VIII)

with hydrazine hydrate to give a compound of the formula IX

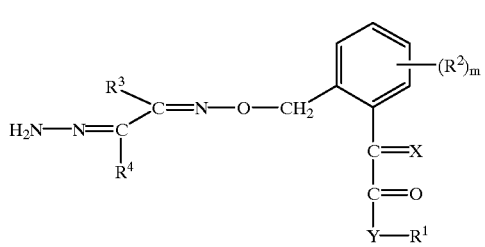

(IX)

and then reacting IX with a carbonyl compound of the formula VI

(VI)

5. A process for preparing compounds of the formula I as claimed in claim 1, which comprises reacting a carbonyl compound of the formula VIII

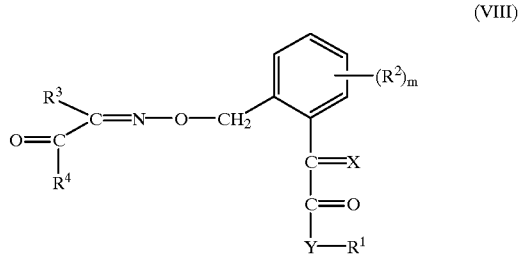

(VIII)

with a hydrazone of the formula VII

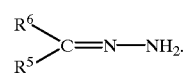

(VIII)

6. A composition suitable for controlling animal pests or harmful fungi, comprising a compound of the formula I or one of its salts as claimed in claim 1 and at least one formulation auxiliary.

7. A composition as claimed in claim 6 for controlling animal pests of the insects, arachnids or nematodes classes.

8. A method of controlling animal pests or harmful fungi, which comprises treating the pests or harmful fungi, their habitat or the plants, surfaces, materials or spaces to be kept free from them with an effective amount of a compound of the formula I or one of its salts as claimed in claim 1.

* * * * *

UNITED STATES PATENT AND TRADEMARK OFFICE
CERTIFICATE OF CORRECTION

PATENT NO. : 6,043,282
DATED : March 28, 2000
INVENTOR(S) : BAYER et al.

It is certified that error appears in the above-indentified patent and that said Letters Patent is hereby corrected as shown below:

Column 121, claim 1, line 66, change "$NOCE_3$" to --$NOCH_3$--

Column 122, claim 3, line 59, change the formula in "VI" to appear in --IX--.
Column 123, claim 3, line 2, change the formula in "IX" to appear in --VI--.

Column 124, claim 5, line 26, change the formula designation "VIII" to --VII--.

Signed and Sealed this

Twentieth Day of March, 2001

Attest:

NICHOLAS P. GODICI

Attesting Officer     Acting Director of the United States Patent and Trademark Office